United States Patent
Armstrong et al.

(10) Patent No.: US 10,017,581 B2
(45) Date of Patent: Jul. 10, 2018

(54) METHODS AND COMPOSITIONS FOR TREATMENT OF POMPE DISEASE

(71) Applicants: VALERION THERAPEUTICS, LLC, Concord, MA (US); Dustin D. Armstrong, Quincy, MA (US); Jeffrey C. Way, Cambridge, MA (US)

(72) Inventors: Dustin D. Armstrong, Quincy, MA (US); Jeffrey C. Way, Cambridge, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 0 days.

(21) Appl. No.: 14/769,270

(22) PCT Filed: Feb. 20, 2014

(86) PCT No.: PCT/US2014/017483
§ 371 (c)(1),
(2) Date: Aug. 20, 2015

(87) PCT Pub. No.: WO2014/130723
PCT Pub. Date: Aug. 28, 2014

(65) Prior Publication Data
US 2016/0108133 A1  Apr. 21, 2016

Related U.S. Application Data

(60) Provisional application No. 61/926,874, filed on Jan. 13, 2014, provisional application No. 61/767,016, filed on Feb. 20, 2013.

(51) Int. Cl.
| | |
|---|---|
| *A61K 38/00* | (2006.01) |
| *C07K 16/40* | (2006.01) |
| *C07K 16/44* | (2006.01) |
| *C12N 9/26* | (2006.01) |
| *A61K 9/00* | (2006.01) |
| *A61K 38/47* | (2006.01) |
| *A61K 47/68* | (2017.01) |
| *A61K 39/00* | (2006.01) |

(52) U.S. Cl.
CPC ............ *C07K 16/40* (2013.01); *A61K 9/0019* (2013.01); *A61K 38/47* (2013.01); *A61K 47/6871* (2017.08); *C07K 16/44* (2013.01); *C12N 9/2408* (2013.01); *A61K 38/00* (2013.01); *A61K 2039/505* (2013.01); *C07K 2317/14* (2013.01); *C07K 2317/24* (2013.01); *C07K 2317/55* (2013.01); *C07K 2317/56* (2013.01); *C07K 2317/565* (2013.01); *C07K 2317/622* (2013.01); *C07K 2317/77* (2013.01); *C07K 2317/92* (2013.01); *C07K 2317/94* (2013.01); *C07K 2319/10* (2013.01); *C07K 2319/30* (2013.01); *C07K 2319/33* (2013.01); *C07K 2319/70* (2013.01); *C12Y 302/0102* (2013.01)

(58) Field of Classification Search
CPC ... C12N 9/2408; A61K 38/00; C07K 2317/24
See application file for complete search history.

(56) References Cited

U.S. PATENT DOCUMENTS

| | | |
|---|---|---|
| 5,541,087 A | 7/1996 | Lo et al. |
| 5,622,699 A | 4/1997 | Ruoslahti et al. |
| 5,726,044 A | 3/1998 | Lo et al. |
| 6,068,829 A | 5/2000 | Ruoslahti et al. |
| 6,118,045 A | 9/2000 | Reuser et al. |
| 6,174,687 B1 | 1/2001 | Rajotte et al. |
| 6,180,084 B1 | 1/2001 | Ruoslahti et al. |
| 6,232,287 B1 | 5/2001 | Ruoslahti et al. |
| 6,296,832 B1 | 10/2001 | Ruoslahti et al. |
| 6,303,573 B1 | 10/2001 | Ruoslahti et al. |
| 6,306,365 B1 | 10/2001 | Ruoslahti et al. |
| 6,328,958 B1 | 12/2001 | Amalfitano et al. |
| 6,537,785 B1 | 3/2003 | Canfield |
| 7,001,994 B2 | 2/2006 | Zhu |
| 7,056,712 B2 | 6/2006 | Chen |
| 7,351,410 B2 | 4/2008 | van Bree et al. |
| 7,371,366 B2 | 5/2008 | Canfield |
| 7,442,372 B2 | 10/2008 | Kakkis |
| 7,655,226 B2 | 2/2010 | Van Bree et al. |
| 7,666,405 B2 | 2/2010 | Amalfitano et al. |
| 7,723,296 B2 | 5/2010 | Zhu |
| 7,786,277 B2 | 8/2010 | Zhu |
| 8,124,073 B2 | 2/2012 | Stefano |
| 8,399,657 B2 | 3/2013 | Zhu |
| 8,609,615 B2 | 12/2013 | Armstrong |

(Continued)

FOREIGN PATENT DOCUMENTS

| | | |
|---|---|---|
| WO | WO-88/03559 A1 | 5/1988 |
| WO | WO-90/02338 A1 | 3/1990 |

(Continued)

OTHER PUBLICATIONS

Abhinandan and Martin, "Analyzing the "Degree of Humanness" of Antibody Sequences," Journal Molecular Biology, vol. 369:852-862 (2007).
Bijvoet et al., "Generalized Glycogen Storage and Cardiomegaly in a Knockout Mouse Model of Pompe Disease," Human Moleular Genetics, vol. 7(1):53-62 (1998).
Bijvoet, et al., "Recombinant Human Acid α-Glucosidase: High Level Production in Mouse Milk, Biochemical Characteristics, Correction of Enzyme Deficiency in GSDII KO Mice," Human Molecular Genetics, vol. 7(11):1815-1824 (1998).
Case et al., "Physical Therapy Management of Pompe Disease," Genetics in Medicine, vol. 8(5):318-327 (2006).
Fukuda et al., "Autophagy and Mistargting of Therapeutic Enzyme in Skeletal Muscle in Pompe Disease," Molecular Therapy, vol. 14(6):831-839 (2006).

(Continued)

*Primary Examiner* — Karen Cochrane Carlson
(74) *Attorney, Agent, or Firm* — Lisa M. Warren, Esq.; Morse, Barnes-Brown & Pendleton, P.C.

(57) ABSTRACT

In certain embodiments, the present disclosure provides compositions and methods for treating Pompe disease.

32 Claims, 1 Drawing Sheet
(1 of 1 Drawing Sheet(s) Filed in Color)

(56) References Cited

U.S. PATENT DOCUMENTS

| | | | |
|---|---|---|---|
| 8,679,478 | B2 | 3/2014 | Koeberl |
| 8,759,501 | B2 | 6/2014 | Zhu et al. |
| 8,785,168 | B2 | 7/2014 | LeBowitz et al. |
| 8,809,282 | B2 | 8/2014 | Kishnani et al. |
| 8,834,866 | B2 | 9/2014 | Armstrong |
| 8,900,552 | B2 | 12/2014 | Chen |
| 8,906,379 | B2 | 12/2014 | Stefano |
| 8,926,967 | B2 | 1/2015 | Dodge et al. |
| 9,114,178 | B2 | 8/2015 | Armstrong |
| 2003/0166877 | A1 | 9/2003 | Gillies et al. |
| 2008/0292618 | A1 | 11/2008 | Weisbart |
| 2009/0117091 | A1* | 5/2009 | LeBowitz ........ A61K 47/48238 424/94.61 |
| 2010/0119502 | A1 | 5/2010 | Do et al. |
| 2010/0143358 | A1 | 6/2010 | Weisbart |
| 2011/0104187 | A1 | 5/2011 | Chen et al. |
| 2012/0003202 | A1 | 1/2012 | Calias et al. |
| 2012/0276072 | A1 | 11/2012 | Koeberl et al. |
| 2014/0186326 | A1 | 7/2014 | Canfield et al. |
| 2014/0377246 | A1 | 12/2014 | Tomatsu et al. |
| 2015/0044194 | A1 | 2/2015 | Valenzano et al. |
| 2015/0064181 | A1 | 3/2015 | Armstrong |
| 2015/0152170 | A1 | 6/2015 | Armstrong et al. |

FOREIGN PATENT DOCUMENTS

| | | |
|---|---|---|
| WO | WO-91/09953 A1 | 7/1991 |
| WO | WO-91/16024 A1 | 10/1991 |
| WO | WO-91/17424 A1 | 11/1991 |
| WO | WO-97/32602 A1 | 9/1997 |
| WO | WO-98/53804 | 12/1998 |
| WO | WO-2005/002515 | 1/2005 |
| WO | WO-2008/091911 A2 | 7/2008 |
| WO | WO-2008/148063 A1 | 12/2008 |
| WO | WO-2010/044894 | 4/2010 |
| WO | WO-2010/148010 A1 | 12/2010 |
| WO | WO-2013/138662 A1 | 9/2013 |
| WO | WO-2013/177428 | 11/2013 |
| WO | WO-2014/130722 A1 | 8/2014 |
| WO | WO-2014/130723 A1 | 8/2014 |
| WO | WO-2015/106290 A1 | 7/2015 |
| WO | WO-2015/192092 A1 | 12/2015 |

OTHER PUBLICATIONS

Geel et al., "Pompe disease: Current State of Treatment Modalities and Animal Models," Molecular Genetics and Metabolism, vol. 92:299-307 (2007).

Hacker et al., "Polyethyleneimine-Based Transient Gene Expression Processes for Suspension-Adapted HEK-293E and CHO-DG44 Cells," Protein Expression and Purification, vol. 92:67-76 (2013).

Hansen et al., Antibody-mediated Hsp70 Protein Therapy, Brain Research, 1088(1):187-196 (2006).

Hansen et al., Intranuclear Protein Transduction Through a Nucleoside Salvage Pathway, The Journal of Biological Chemistry, vol. 282(29):20790-20793 (2007).

Kikuchi et al., "Clinical and Metabolic Correction of Pompe Disease by Enzyme Therapy in Acid Maltase-deficient Quail," J. Clin. Invest., vol. 101(4):827-833 (1998).

Kunik et al., "Structural Consensus Among Antibodies Defines the Antigen Binding Site," PLoS Computational Biology, vol. 8(2):e1002388 (2012).

Malicdan et al., Lysosomal Myopathies: An Excessive Build-Up in Autophagosomes is too Much to Handle, Neuromuscular Disorders, vol. 18:521-529 (2008).

Martin-Touaux et al., "Muscle as a Putative Producer of Acid α-Glucosidase for Glycogenosis Type II Gene Therapy," Human Molecular Genetics, vol. 11(14):1637-1645 (2002).

Masiero et al, "Autophagy Is Required to Maintain Muscle Mass," Cell Metabolism, vol. 10(6):507-515 (2009).

McVie-Wylie et al., "Biochemical and Pharmacological Charactrization of Different Recombinant Acid Alpha-Glucosidase Preparations Evaluated for the Treatment of Pompe Disease," Molecular Genetics and Metabolism, vol. 94:448-455 (2008).

Moreland et al., "Lysosomal Acid α-Glucosidase Consists of Four Different Peptides Processsed from a Single Chain Precursor," Journal of Biological Chemistry, vol. 280(8):6780-6791 (2005).

Naydenova et al., "Inosine and Equilibrative Nucleoside Transporter 2 Contribute to Hypoxic Preconditioning in the Murine Cardiomyocyte HL-1 cell line," Am. J. Physiol. Heart Circ. Physiol., vol. 294(6):H2687-2692 (2008).

Pasqualini et al., "Organ Targeting in Vivo Using Phage Display Peptide Libraries," Letters to Nature, vol. 380:364-366 (1996).

Pasqualini et al., "Searching for a Molecular Address in the Brain," Molecular Psychiatry, vol. 1:421-423 (1996).

Pennycooke et al., "Differential Expression of Human Nucleoside Transporters in Normal and Tumor Tissue," Biochemical and Biophysical Research Communications, vol. 280(3):951-959 (2001).

Raben et al., "Conditional Tissue-Specific Expression of the Acid Alpha-Glucosidase (GAA) Gene in the GAA Knockout Mice: Implications for Therapy," Human Molecular Genetics, vol. 10(19):2039-2047 (2001).

Raben et al., "Enzyme Replacement Therapy in the Mouse Model of Pompe Disease," Molecular Genetics and Metabolism, vol. 80:159-169 (2003).

Raben et al., "Induction of Tolerance to a Recombinant Human Enzyme, Acid Alpha-Glucosidase, in Enzyme Deficient Knockout Mice," Transgenic Research, vol. 12:171-178 (2003).

Raben et al., "Modulation of Disease Severity in Mice with Targeted Disruption of the Acid Alpha-Glucosidase Gene," Neuromuscular Disorders, vol. 10:283-291 (2000).

Raben et al., "Suppression of Autophagy in Skeletal Muscle Uncovers the Accumulation of Ubiquitinated Proteins and Their Potential Role in Muscle Damage in Pompe disease," Human Molecular Genetics, vol. 17(24):3897-3908 (2008).

Raben et al., "Targeted Disruption of the Acid Alpha-Glucosidase Gene in Mice Causes an Illness with Critical Features of Both Infantile and Adult Human Glycogen Storage Disease Type II," The Journal of Biological Chemistry, vol. 273(3):19086-19092 (1998).

Rajotte et al., "Membrane Dipeptidase Is the Receptor for a Lung-Targeting Peptide Identified by in Vivo Phage Display," The Journal of Biological Chemistry, vol. 274(17):11593-11598 (1999).

Rajotte et al., "Molecular Heterogeneity of the Vascular Endothelium Revealed by In Vivo Phase Display," Journal Clinical Investment., vol. 102(2):430-437 (1998).

Samoylova et al., "Elucidation of Muscle-Binding Peptides by Phage Display Screening," Muscle & Nerve, vol. 22:460-466 (1999).

Schoser et al., "Therapeutic Approaches in Glycogen Storage Disease Type II/ Pompe Disease," Neurotherapeutics, vol. 5(4):569-578 (2008).

Sidman et al., "Temporal Neuropathological and Behavioral Phenotype of $6^{neo}/6^{neo}$ Pompe Disease Mice," Journal Neuropathology Exp Neurology, vol. 67(8):803-818 (2008).

Sun et al., "Enhanced Efficacy of an AAV Vector Encoding Chimeric, Highly-Secreted Acid α-Glucosidase in Glycogen Storage Disease Type II," Molecular Therapy, vol. 14(6):822-830 (2006).

Takikita et al., "The Values and Limits of an In Vitro Model of Pompe Disease: The Best Laid Schemes O' Mice an' Men . . . " Autophagy, vol. 5(5):729-314 (2009).

Weisbart RH et al., "An Autoantibody is Modified for Use as a Delivery System to Target the Cell Nucleus: Therapeutic Implications," Journal of Autoimmunity, vol. 11(5):539-546 (1998).

Weisbart RH et al., "An intracellular Delivery Vehicle for Pprotein Tansduction of Micro-Dystrophin," Journal of Drug Targeting, vol. 13(2):81-87 (2005).

Weisbart RH et al., "Novel Protein Transfection of Primary Rat Cortical Neurons Using an Antibody that Penetrates Living Cells," The Journal of Immunology, vol. 164:6020-6026 (2000).

Weisbart RH et al., "Nuclear Delivery of p53 C-Terminal Peptides into Cancer Calls Using scFv Fragments of a Monoclonal Antibody that Penetrates Living Cells," Cancer Letters, vol. 195(2):211-219 (2003).

(56) References Cited

OTHER PUBLICATIONS

Weisbart RH, et al., "Cell type Specific Targeted Intracellular Delivery into Muscle of a Monoclonal Antibody that Binds Myosin IIb," Molecular Immunology, vol. 39(13):783-789 (2003).
Wylie et al., "Tissue-Specific Inactivation of Murine M6P/IGF2R," American Journal of Pathology, 162(1):321-28 (2003).
Xu et al., "Impaired Organization and Function of Myofilaments in Single Muscle Fibers from a Mouse Model of Pompe Disease," Journal Appl Physiology, vol. 108:1383-1388 (2010).
Xu et al., "Improved Efficacy of Gene Therapy Approaches for Pompe Disease Using a New, Immune-Deficient GSD-II Mouse Model," Gene Therapy, vol. 11:15890-1598 (2004).
Zack DJ et al., "Mechanisms of Cellular Penetration and Nuclear Localization of an Anti-Double Strand DNA Autoantibody," Journal of Immunology, vol. 157(5):2082-2088 (1996).
Prince William S et al: "Lipoprotein receptor binding, cellular uptake, and lysosomal delivery of fusions between the receptor-associated protein (RAP) and alpha-L-iduronidase or acid alpha-glucosidase", Journal of Biological Chemistry, American Society for Biochemistry and Molecular Biology, US, vol. 279, No. 33, Aug. 13, 2004 (Aug. 13, 2004), pp. 35037-35046.
J. A. Maga et al: "Glycosylation-independent Lysosomal Targeting of Acid alpha-Glucosidase Enhances Muscle Glycogen Clearance in Pompe Mice", Journal of Biological Chemistry, vol. 288, No. 3, Nov. 27, 2012 (Nov. 27, 2012), pp. 1428-1438.
Extended European Search Report, Application No. EP 14 753 494.5, dated Nov. 10, 2016 (13 pages).
International Search Report, Application No. PCT/US2014017483, dated Jun. 18, 2014 (7 pages).

\* cited by examiner

METHODS AND COMPOSITIONS FOR TREATMENT OF POMPE DISEASE

RELATED APPLICATIONS

This application is a national stage filing under 35 U.S.C. § 371 of International Application No. PCT/US2014/017483, filed Feb. 20, 2014, which claims the benefit of the filing date under 35 U.S.C. 119(e) to U.S. provisional application Ser. No. 61/767,016, filed Feb. 20, 2013 and U.S. provisional application Ser. No. 61/926,874, filed Jan. 13, 2014, the entire contents of which is hereby incorporated by reference. International Application No. PCT/US2014/017483 was published under PCT Article 21(2) in English.

SEQUENCE LISTING

The instant application contains a Sequence Listing which has been submitted electronically in ASCII format and is hereby incorporated by reference in its entirety. Said ASCII copy, created on Aug. 20, 2015, is named 1061990007301_Seq.txt and is 80,840 bytes in size.

BACKGROUND OF THE DISCLOSURE

Glycogen storage disease type II (GSDII or Pompe disease) is an autosomal recessive metabolic disorder characterized by a deficiency in the lysosomal enzyme acid α-glucosidase (GAA). Patients suffering from the disorder are unable to convert lysosomal stores of glycogen into glucose, which leads initially to accumulation of glycogen in the lysosome, and later to accumulation of glycogen in the cytoplasm and autophagic vesicles of cells. Eventually, the buildup of toxic levels of glycogen damages the cells and impairs proper function. In particular, muscle cell dysfunction is a hallmark of Pompe disease, with symptoms ranging from hypertrophic cardiomyopathy, weakness, skeletal muscle dysfunction and early infant death in infantile onset forms of the disease, to progressive degeneration of skeletal muscle function and respiratory muscle dysfunction in juvenile and adult onset forms of the disease.

Treatment of Pompe disease with enzyme replacement therapy (ERT) has provided partial restoration of muscle function and prolonged survival in some patients. However, prior therapies based on delivery of the 110 kDa precursor GAA protein have achieved delivery of protein only to the lysosome. Delivery of protein exclusively to the lysosome has proven ineffective to clear glycogen build-up in the cytoplasm or other extra-lysosomal spaces. Additionally, approaches based on delivering protein to the lysosome have relied on uptake through mannose-6-phosphate receptors in the lysosome, and high dosages appear to be required.

SUMMARY OF THE DISCLOSURE

There is a need in the art for methods and compositions for clearing cytoplasmic glycogen build-up in patients with Pompe disease, as well as a need for alternative therapies for treating Pompe disease. Such methods and compositions would improve treatment of Pompe disease, particularly in patients whose disease is severe enough and/or advanced enough to have significant cytoplasmic glycogen accumulation. The present disclosure provides such methods and compositions. In certain embodiments, the methods and compositions provided herein decrease glycogen build-up in, at least, the cytoplasm. In certain embodiments, the methods and compositions also decrease glycogen build-up in lysosomes and autophagic vesicles. Similarly, the methods and compositions provided herein can be used to improve deleterious symptoms of Pompe Disease, for example, to decrease levels of one or more of alanine transaminase, aspartate transaminase, alkaline phosphatase, and creatine phosphokinase (e.g., to decrease abnormally elevated levels of one or more such enzymes, such as in serum).

In a first aspect, the disclosure provides a chimeric polypeptide comprising: (i) a mature acid alpha-glucosidase (GAA) polypeptide and (ii) an internalizing moiety that promotes delivery into cells. In other words, the disclosure provides chimeric polypeptides having two portions: a portion comprising a mature GAA polypeptide (a GAA polypeptide comprising mature GAA; a GAA portion comprising a GAA polypeptide comprising a mature GAA) and a portion comprising an internalizing moiety that promotes delivery into cells. In certain embodiments, the internalizing moiety promotes transport into cytoplasm of cells. In certain embodiments, the chimeric polypeptide has acid alpha-glucosidase activity, and does not comprise a GAA precursor polypeptide of approximately 110 kilodaltons, particularly does not comprise the precursor polypeptide of 110 kilodaltons generated endogenously by the cleavage of amino acids 1-56 of SEQ ID NO: 1 by signal peptidase and protease 1. In certain embodiments, the chimeric polypeptide does not comprise the signal sequence of a GAA precursor polypeptide (e.g., see the signal sequence depicted for SEQ ID NO: 1 or 2). In other words, the chimeric polypeptide comprises a mature GAA portion and an internalizing moiety portion but does not include amino acids 1-56 of SEQ ID NO: 1 (e.g., the GAA portion comprises a GAA polypeptide but does not include amino acids 1-56 of SEQ ID NO: 1). The chimeric polypeptide may further comprise additional portions, such as linker moieties and/or tags but, in certain embodiments, does not include the GAA precursor polypeptide of approximately 110 kilodaltons (e.g., the GAA precursor as defined in Moreland et al, 2005, J. Biol. Chem. 280: 6780) and/or the full length GAA polypeptide set forth in SEQ ID NO: 1 or 2.

In certain embodiments, the mature GAA polypeptide has a molecular weight of approximately 70-76 kilodaltons. In certain embodiments, the mature GAA polypeptide has a molecular weight of about 70 kDa or about 76 kDa. In certain embodiments, the mature GAA polypeptide comprises an amino acid sequence selected from about: residues 122-782 of SEQ ID NOs: 1 or 2; residues 123-782 of SEQ ID NOs: 1 or 2; residues 204-782 of SEQ ID NOs: 1 or 2; residues 206-782 of SEQ ID NOs: 1 or 2; or residues 288-782 of SEQ ID NOs: 1 or 2. In certain embodiments, the mature GAA polypeptide consists of an amino acid sequence selected from about residues: residues 122-782 of SEQ ID NOs: 1 or 2; residues 123-782 of SEQ ID NOs: 1 or 2; residues 204-782 of SEQ ID NOs: 1 or 2; residues 206-782 of SEQ ID NOs: 1 or 2; or residues 288-782 of SEQ ID NOs: 1 or 2. In other embodiments, the C-terminal amino acid residues of the mature GAA polypeptide varies, such that the C-terminal amino acid residues is any of residues 816-881, as set forth in SEQ ID NOs: 1 or 2. In certain embodiments, the mature GAA polypeptide comprises or consists of the amino acid sequence of SEQ ID NO: 3 or SEQ ID NO: 4. In certain embodiments, the chimeric polypeptide comprises any of the foregoing. In certain embodiments, the GAA polypeptide portion of the chimeric polypeptide consists of any of the foregoing examples of mature GAA. Although the chimeric polypeptide comprises additional amino acid sequence, in certain embodiments, the chimeric polypeptide does include additional GAA amino acid sequence contiguous with the mature GAA polypeptide portion. In other embodiments, the chimeric polypeptide comprises mature GAA and also comprises additional N- and or C-terminal contiguous GAA polypeptide sequence, such as the longer active GAA polypeptides described herein (e.g., the GAA portion comprises a GAA polypeptide comprising mature GAA). As used herein, "GAA polypeptide" refers to a polypeptide that comprises a portion corresponding to mature GAA but may also include additional N- and/or C-terminal portions naturally present in a GAA polypeptide (e.g., a native GAA polypeptide). In certain embodiments, a GAA polypeptide for use in the chimeric polypeptides and methods of the disclosure does not include residues 1-56 of SEQ ID NO: 1. In certain embodiments, the GAA polypeptide does not correspond to the 110 kilodalton, GAA precursor polypeptide.

In some embodiments, the chimeric polypeptide has acid alpha-glucosidase activity.

In some embodiments, the chimeric polypeptide does not comprise the full length, GAA translation product set forth in SEQ ID NO: 1 (e.g., the GAA polypeptide portion does not include the full length, GAA translation product set forth in SEQ ID NO: 1). In some embodiments, neither the GAA polypeptide nor the chimeric polypeptide comprise a contiguous amino acid sequence corresponding to the amino acids 1-56 of SEQ ID NO: 1 or 2 (e.g., the GAA polypeptide lacks the portion corresponding to amino acids 1-56, preferably 1-57 of SEQ ID NO: 1 or 2, and this region is not present in the chimeric polypeptide). In some embodiments, the chimeric polypeptide comprises a GAA polypeptide that lacks at least a portion of the GAA full linker region, wherein the full linker region (SEQ ID NO: 31) corresponds to the amino acids 57-78 of SEQ ID NOs: 1 or 2 (e.g., the chimeric polypeptide may include some of the full linker region but does not include all of the full linker region). In some embodiments, neither the GAA polypeptide nor the chimeric polypeptide comprise a contiguous amino acid sequence corresponding to the amino acids 1-60 of SEQ ID NO: 1 or 2 (e.g., the GAA polypeptide lacks the portion corresponding to amino acids 1-60 of SEQ ID NO: 1 or 2, and this region is not present in the chimeric polypeptide). In some embodiments, the chimeric polypeptide or GAA polypeptide comprises the amino acid sequence of SEQ ID NO: 21. In some embodiments, the GAA polypeptide comprises amino acids 61-952 of SEQ ID NO: 1. In some embodiments, neither the GAA polypeptide nor the chimeric polypeptide comprise a contiguous amino acid sequence corresponding to the amino acids 1-66 of SEQ ID NO: 1 or 2 (e.g., the GAA polypeptide lacks the portion corresponding to amino acids 1-66 of SEQ ID NO: 1 or 2, and this region is not present in the chimeric polypeptide). In some embodiments, the chimeric polypeptide or GAA polypeptide comprises the amino acid sequence of SEQ ID NO: 22. In some embodiments, the GAA polypeptide comprises amino acids 67-952 of SEQ ID NO: 1. In some embodiments, neither the GAA polypeptide nor the chimeric polypeptide comprise a contiguous amino acid sequence corresponding to the amino acids 1-69 of SEQ ID NO: 1 or 2 (e.g., the GAA polypeptide lacks the portion corresponding to amino acids 1-69 of SEQ ID NO: 1 or 2, and this region is not present in the chimeric polypeptide). In some embodiments, the chimeric polypeptide or GAA polypeptide comprises the sequence of SEQ ID NO: 23. In some embodiments, the GAA polypeptide comprises amino acids 70-952 of SEQ ID NO: 1. The disclosure contemplates combinations of any one or more of these features.

In certain embodiments, the chimeric polypeptide comprises or consists of the amino acid sequence set forth in SEQ ID NO: 11 or 12, or set forth in either of these sequence identifiers but in the absence of one or more epitope tags (e.g., in the absence of, for example, a His and/or Myc epitope tag).

In certain embodiments, the chimeric polypeptide and/or the mature GAA is glycosylated. In certain embodiments, the chimeric polypeptide and/or mature GAA is not glycosylated. In certain embodiments, the mature GAA has a glycosylation pattern that differs from that of naturally occurring human GAA.

In certain embodiments, the internalizing moiety promotes delivery of the chimeric polypeptide into cytoplasm of cells. In certain embodiments, the internalizing moiety promotes delivery of said chimeric polypeptide into muscle cells, such as skeletal or cardiac muscle cells (e.g., promotes delivery into cytoplasm of such cells). In certain embodiments, the internalizing moiety promotes delivery of said chimeric polypeptide into neurons or hepatocytes (e.g., promotes delivery into cytoplasm of such cells).

In certain embodiments, the chimeric polypeptide comprises N-linked oligosaccharide chains modified with M6P residues. In certain embodiments, the chimeric polypeptide comprises a KFERQ-like sequence (SEQ ID NO: 33).

In certain embodiments, the chimeric polypeptide further comprises one or more polypeptide portions that enhance one or more of in vivo stability, in vivo half life, uptake/administration, production, or purification. Exemplary polypeptide portions include epitope tags, such as HA and myc tags, as well as the Fc region of an immunoglobulin or all or a portion of HSA.

In certain embodiments, the internalizing moiety comprises an antibody or antigen binding fragment. In certain embodiments, the antibody or antigen binding fragment is a monoclonal antibody or fragment. In certain embodiments, the antibody or antigen binding fragment is human or humanized. In other embodiments, the antibody or antigen binding fragment is murine. Exemplary antigen binding fragments include, scFv, Fv, Fab, and the like. Further exemplary antigen binding fragments comprise a heavy chain variable region (VH) comprising CDR1, CDR2, and CDR3, and a light chain variable region (VL) comprising CDR1, CDR2, and CDR3. When referring to suitable internalizing moieties, they preferably retain the antigen/target binding characteristics and cell penetrating characteristics when present in the context of the chimeric polypeptide.

In certain embodiments, the chimeric polypeptides comprise as an internalizing moiety, an antibody or antigen binding fragment thereof select from: monoclonal antibody 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing. In certain embodiments, the antibody or antigen binding fragment thereof is a monoclonal antibody 3E10, or a variant thereof that retains cell penetrating activity, or an antigen binding fragment of 3E10 or said 3E10 variant. In some embodiments, the antibody or antigen binding fragment is a chimeric, humanized, or fully human antibody or antigen binding fragment. In some embodiments, the antibody or antigen binding fragment comprises a heavy chain variable domain comprising an amino acid sequence at least 95% identical to SEQ ID NO: 9, or a humanized variant thereof. In some embodiments, the antibody or antigen binding fragment comprises a light chain variable domain comprising an amino acid sequence at least 95% identical to SEQ ID NO: 10, or a humanized variant thereof. In some embodiments, the antibody or antigen binding fragment comprises a heavy chain variable domain comprising the amino acid sequence of SEQ ID NO: 9 and a light chain variable domain comprising the amino acid sequence of SEQ ID NO: 10, or a humanized variant thereof. For any description of an antibody or antigen binding fragment, the disclosure contemplates that the antibody or antigen binding fragment may comprise a heavy chain and a light chain, such as a heavy chain comprising a heavy chain variable domain and a light chain comprising a light chain variable domain. In some embodiments, the antibody or antigen binding fragment comprises:

a VH CDR1 having the amino acid sequence of SEQ ID NO 13;
a VH CDR2 having the amino acid sequence of SEQ ID NO: 14;
a VH CDR3 having the amino acid sequence of SEQ ID NO: 15;
a VL CDR1 having the amino acid sequence of SEQ ID NO: 16;
a VL CDR2 having the amino acid sequence of SEQ ID NO: 17; and
a VL CDR3 having the amino acid sequence of SEQ ID NO: 18, which CDRs are according to the Kabat system.

In some embodiments, the antibody or antigen binding fragment comprises:

a VH CDR1 having the amino acid sequence of SEQ ID NO 24;
a VH CDR2 having the amino acid sequence of SEQ ID NO: 25;
a VH CDR3 having the amino acid sequence of SEQ ID NO: 26;
a VL CDR1 having the amino acid sequence of SEQ ID NO: 27;
a VL CDR2 having the amino acid sequence of SEQ ID NO: 28; and
a VL CDR3 having the amino acid sequence of SEQ ID NO: 29, which CDRs are according to the IMGT system.

In other words, in certain embodiments, the antibody comprises a heavy chain comprising VH CDR1, VH CDR2, and VH CDR3 of the 3E10 antibody, as determined by Kabat and set forth above, and a light chain comprising a VL CDR1, a VL CD2, and a VL CD3 of the 3E10 antibody, as determined by Kabat and set forth above; or is an antigen binding fragment thereof. In certain other embodiments, the antibody comprises a heavy chain comprising VH CDR1, VH CDR2, and VH CDR3 of the 3E10 antibody, as determined by the IGMT system and set forth above, and a light chain comprising a VL CDR1, a VL CD2, and a VL CD3 of the 3E10 antibody, as determined by the IGMT system and set forth above; or is an antigen binding fragment thereof.

In certain embodiments, the 3E10 antibody, fragment, or variant comprises a heavy chain comprising an amino acid sequence at least 80%, 85%, 90%, 92%, 95%, 96%, 97%, 98%, 99%, or even 100% identical to SEQ ID NO: 9. In certain embodiments, the 3E10 antibody, fragment, or variant comprises a light chain comprising an amino acid sequence at least 80%, 85%, 90%, 92%, 95%, 96%, 97%, 98%, 99%, or even 100% identical to SEQ ID NO: 10. In certain embodiments, the 3E10 antibody, fragment, or variant comprises a heavy chain comprising an amino acid sequence at least 80%, 85%, 90%, 92%, 95%, 96%, 97%, 98%, 99%, or even 100% identical to SEQ ID NO: 9 and a light chain comprising an amino acid sequence at least 80%, 85%, 90%, 92%, 95%, 96%, 97%, 98%, 99%, or even 100% identical to SEQ ID NO: 10. It is understood, that these heavy and light chain regions may, in certain embodiments, be connected by a linker (e.g., such as in the context of an scFv—see SEQ ID NO: 11 and 12). Chimeric polypeptides having any combination of the foregoing or following internalizing moieties and mature GAA portions are contemplated. Moreover, chimeric polypeptides having any combination of the foregoing or following internalizing moieties and GAA portions (e.g., GAA polypeptides) described herein are contemplated. Any such chimeric polypeptides are suitable for use in any of the methods of the disclosure described herein.

In some embodiments, the internalizing moiety is an antibody or antigen-binding fragment (e.g., an antibody fragment). In some embodiments, the internalizing moiety is an antibody fragment, particularly an scFv. In other embodiments, the antibody fragment is a Fab. In some embodiments, the N-terminus of the GAA polypeptide portion is fused to the C-terminus of the heavy chain constant region portion of the Fab. In some embodiments, the N-terminus of the GAA polypeptide portion is fused to the C-terminus of the heavy chain constant region portion of the Fab by means of a linker. In some embodiments, the linker comprises the amino acid sequence of SEQ ID NO: 30. In some embodiments, the antibody or antigen binding fragment is an antibody. In some embodiments, the N-terminus of the GAA polypeptide portion is fused to the C-terminus of the heavy chain Fc portion of the antibody. In some embodiments, the N-terminus of the GAA polypeptide portion is fused to the C-terminus of the heavy chain Fc portion of the antibody by means of a linker. In some embodiments, the linker comprises the amino acid sequence of SEQ ID NO: 30.

In certain embodiments, the internalizing moiety comprises a homing peptide. In certain embodiments, the internalizing moiety transits cellular membranes via an equilibrative nucleoside transporter 1 (ENT1), ENT2, ENT3 or ENT4 transporter. In certain embodiments, the internalizing moiety transits cellular membranes via an ENT2 transporter. By way of example, 3E10 antibody or antigen binding fragment thereof transits cellular membranes via ENT2.

In certain embodiments, the internalizing moiety is capable of binding polynucleotides. In certain embodiments, the internalizing moiety is capable of binding DNA. For example, 3E10 and the particular 3E10 variant described herein are known to bind DNA (e.g., their target—or antigen is DNA). Although these and other DNA binding antibodies are typically not specifically reactive with a single antigen, they do bind DNA with relatively strong affinity. In certain embodiments, the internalizing moiety is capable of binding DNA with a $K_D$ of less than 1 µM. In certain embodiments, the internalizing moiety is capable of binding DNA with a $K_D$ of less than 100 nM, less than 75 nM, less than 50 nM, or even less than 30 nM. For the foregoing, $K_D$ may be determined using, for example, SPR or QCM according to standard protocols.

In certain embodiments, the chimeric polypeptide is a chemical conjugate of mature GAA polypeptide to the internalizing moiety, such as a chemical conjugate comprising a GAA polypeptide portion and an internalizing moiety portion. In other words, the mature GAA portion and the internalizing moiety portion are interconnected, directly or indirectly, via chemical conjugation. In certain embodiments, the chimeric polypeptide is a recombinant, co-translational fusion protein comprising the mature GAA polypeptide and the internalizing moiety. When the chimeric polypeptide is a fusion protein, the mature GAA portion and the internalizing moiety portion may be interconnected directly or indirectly. In certain embodiments, the chimeric polypeptide is produced recombinantly to recombinantly conjugate the mature GAA polypeptide to the internalizing moiety. In certain embodiments, the chimeric polypeptide is produced in a prokaryotic or eukaryotic cell, such as a yeast cell, an avian cell, an insect cell, or a mammalian cell. In certain embodiments, the chimeric polypeptide is produced in a prokaryotic cell, such as a bacterial cell. In certain embodiments, the internalizing moiety is an antibody or an antibody fragment. When the internalizing moiety is an antibody or antibody fragment, the GAA polypeptide may be produced as a fusion to any portion of the antibody or antibody fragment. For example, if the internalizing moiety is a full length antibody or an Fab, the GAA polypeptide may be fused recombinantly to (or chemically conjugated to), for example, the C-terminus of the heavy chain of the antibody or Fab.

Whether chemically or genetically conjugated, in certain embodiments, the conjugate comprises a linker that conjugates or joins, directly or indirectly, the mature GAA polypeptide to the internalizing moiety. In certain embodiments, the conjugate does not include a linker, and the mature GAA polypeptide is conjugated or joined directly to the internalizing moiety. Regardless of whether a linker joins the mature GAA and the internalizing moiety, portions of the internalizing moiety may be joined via a linker (e.g., an scFv has a linker joining VH and VL domains). In certain embodiments, the chimeric polypeptide has a total of 0, 1, or 2 linkers. In other embodiments, the chimeric polypeptide has more than two linkers. Any linkers may be cleavable. Chimeric polypeptides of the disclosure comprise a GAA portion (e.g., a GAA polypeptide) and an internalizing moiety portion. The disclosure contemplates that any of the GAA portions (e.g., a GAA polypeptide comprising mature GAA) and internalizing moiety portions can be joined, as described above, In certain embodiments, the internalizing moiety is conjugated or joined, directly or indirectly, to the N-terminal or C-terminal amino acid of the mature GAA polypeptide or to a longer GAA polypeptide comprising a mature GAA polypeptide. In other words, regardless of whether the mature GAA portion and the internalizing portion are contiguous or separated by one or more amino acid residues, the disclosure contemplates embodiments in which the mature GAA portion is located N-terminal to the internalizing moiety portion and embodiments in which the mature GAA portion is located C-terminal to the internalizing moiety portion. In certain embodiments, the internalizing moiety is conjugated or joined to an internal amino acid of the mature GAA polypeptide.

In a related aspect, the disclosure provides compositions comprising one or more chimeric polypeptides of the disclosure. Chimeric polypeptides for use in such compositions may have any combination of features, as set forth above. In one embodiment, the disclosure provides a composition comprising (a) a first chimeric polypeptide comprising: (i) a mature acid alpha-glucosidase (GAA) polypeptide having a molecular weight of approximately 76 kDa and (ii) an internalizing moiety; and (b) a second chimeric polypeptide comprising: (i) a mature acid alpha-glucosidase (GAA) polypeptide having a molecular weight of approximately 70 kDa and (ii) an internalizing moiety; wherein the first chimeric polypeptide and the second chimeric polypeptide each have acid alpha-glucosidase activity, and wherein neither the first chimeric polypeptide nor the second chimeric polypeptide comprise a GAA precursor polypeptide of approximately 110 kilodaltons. The foregoing is merely exemplary of suitable compositions. The internalizing moities for the first and second chimeric polypeptide may be the same or different.

In certain embodiments, the composition of two or more chimeric polypeptides further comprises a polypeptide comprising a precursor GAA polypeptide having a molecular weight of about 110 kDa. Also contemplated are compositions in which one or more chimeric polypeptides of the disclosure that do not include a GAA precursor polypeptide of approximately 110 kDa is combined with a polypeptide comprising a precursor GAA polypeptide having a molecular weight of about 110 kDa.

In a related embodiment, the disclosure provides a composition comprising (a) a chimeric polypeptide comprising: (i) a mature acid alpha-glucosidase (GAA) polypeptide and (ii) a internalizing moiety that promotes transport into cytoplasm of cells; wherein the chimeric polypeptide has acid alpha-glucosidase activity, and wherein the chimeric polypeptide does not comprise a GAA precursor polypeptide of approximately 110 kilodaltons; and (b) a polypeptide comprising a precursor GAA polypeptide having a molecular weight of about 110 kDa. The foregoing is merely exemplary of suitable compositions.

In another aspect, the disclosure provides a nucleic acid construct comprising a nucleotide sequence that encodes any of the chimeric polypeptides of the disclosure. For example, the disclosure provides a nucleic acid construct, comprising a nucleotide sequence that encodes a mature GAA polypeptide (or a GAA polypeptide portion), operably linked to a nucleotide sequence that encodes an internalizing moiety, wherein the nucleic acid construct encodes a chimeric polypeptide having acid alpha-glucosidase enzymatic activity and having the internalizing activity of the internalizing moiety, and wherein the nucleic acid construct does not encode a chimeric polypeptide comprising a GAA precursor polypeptide of approximately 110 kilodaltons or does not encode a polypeptide comprising a portion corresponding to residues 1-56 of SEQ ID NO: 1.

In some embodiments, the disclosure provides a vector comprising any of the nucleic acid constructs of the disclosure. In some embodiments, the disclosure provides a host cell comprising any of the vectors of the disclosure. In some embodiments, the host cell comprises and is capable of expressing the vector. In some embodiments, the disclosure provides method of producing a chimeric polypeptide comprising culturing any of the host cells of the disclosure under appropriate conditions to allow expression of the polypeptide to occur. The disclosure contemplates embodiments in which a chimeric polypeptide comprises a single polypeptide chain, as well as embodiments in which a chimeric polypeptide comprises more than one polypeptide chain. When a chimeric polypeptide comprises more than one polypeptide chain that associates in the active polypeptide, the disclosure contemplates methods and compositions in which both polypeptide chains are present in and expressed from the same vector, as well as methods and compositions in which each chain is present in and expressed from a different vector which may be co-expressed in the same host cell.

In another aspect, the disclosure provides a composition comprising any of the chimeric polypeptides of the disclosure, including any chimeric polypeptide having any combination of the foregoing aspects and embodiments, and a pharmaceutically acceptable carrier. In certain embodiments, the composition is a sterile composition. In certain embodiments, the composition is substantially pyrogen-free.

In another aspect, the disclosure provides a variety of in vitro and in vivo methods. In one aspect, the disclosure provides a method of treating Pompe disease in a subject in need thereof, comprising administering to the subject an effective amount of any one or more of the chimeric polypeptides or compositions of the disclosure.

In another aspect, the disclosure provides a method of treating Pompe disease in a subject in need thereof, comprising administering to the subject an effective amount of a chimeric polypeptide comprising: (i) a mature acid alpha-glucosidase (GAA) polypeptide and (ii) an internalizing moiety; wherein the chimeric polypeptide has acid alpha-glucosidase activity, and wherein the chimeric polypeptide does not comprise a GAA precursor polypeptide of approximately 110 kilodaltons.

In another aspect, the disclosure provides a method of increasing acid alpha-glucosidase enzyme activity in a cell, comprising contacting the cell with a chimeric polypeptide comprising: (i) a mature acid alpha-glucosidase (GAA) polypeptide and (ii) an internalizing moiety; wherein the chimeric polypeptide has acid alpha-glucosidase activity, and wherein the chimeric polypeptide does not comprise a GAA precursor polypeptide of approximately 110 kilodaltons.

In another aspect, the disclosure provides a method of decreasing glycogen accumulation in cytoplasm of muscle cells, comprising contacting muscle cells with a chimeric polypeptide, which chimeric polypeptide comprises (i) a mature acid alpha-glucosidase (GAA) polypeptide and (ii) a internalizing moiety that promotes delivery into cytoplasm of cells; wherein the chimeric polypeptide has acid alpha-glucosidase activity, and wherein the chimeric polypeptide does not comprise a GAA precursor polypeptide of approximately 110 kilodaltons.

In another aspect, the disclosure provides a method of decreasing glycogen accumulation in cytoplasm and lysosomes of muscle cells, comprising contacting muscle cells with a chimeric polypeptide, which chimeric polypeptide comprises (i) a mature acid alpha-glucosidase (GAA) polypeptide and (ii) a internalizing moiety; wherein the chimeric polypeptide has acid alpha-glucosidase activity, and wherein the chimeric polypeptide does not comprise a GAA precursor polypeptide of approximately 110 kilodaltons.

In another aspect, the disclosure provides a method of decreasing glycogen accumulation in cytoplasm, lysosomes, and autophagic vacuoles of muscle cells, comprising contacting muscle cells with a chimeric polypeptide, which chimeric polypeptide comprises (i) a mature acid alpha-glucosidase (GAA) polypeptide and (ii) a internalizing moiety; wherein the chimeric polypeptide has acid alpha-glucosidase activity, and wherein the chimeric polypeptide does not comprise a GAA precursor polypeptide of approximately 110 kilodaltons.

The following exemplary embodiments are applicable to any of the foregoing methods of the disclosure. Moreover, the disclosure contemplates combinations of these features with each other, as well as with the aspects and embodiments of the disclosure detailed above and throughout the specification. For example, any of the chimeric polypeptides described herein, such as a chimeric polypeptide comprising a GAA polypeptide portion comprising a mature GAA polypeptide (e.g., a GAA polypeptide), as described herein, and an internalizing moiety portion, as described herein may be used in any of the in vivo or in vitro methods of the disclosure.

In certain embodiments, the method comprises use of a chimeric polypeptide, wherein the mature GAA polypeptide has a molecular weight of approximately 70-76 kilodaltons. In certain embodiments, the method comprises the use of a chimeric polypeptide, wherein the mature GAA polypeptide has a molecular weight of approximately 70 kilodaltons or approximately 76 kDa. In certain embodiments, the mature GAA polypeptide has a molecular weight of approximately 70-76 kilodaltons. In certain embodiments, the mature GAA polypeptide has a molecular weight of about 70 kDa or about 76 kDa. In certain embodiments, the mature GAA polypeptide comprises an amino acid sequence selected from: residues 122-782 of SEQ ID NOs: 1 or 2; residues 123-782 of SEQ ID NOs: 1 or 2; residues 204-782 of SEQ ID NOs: 1 or 2; residues 206-782 of SEQ ID NOs: 1 or 2; or residues 288-782 of SEQ ID NOs: 1 or 2. In certain embodiments, the mature GAA polypeptide consists of an amino acid sequence selected from residues: residues 122-782 of SEQ ID NOs: 1 or 2; residues 123-782 of SEQ ID NOs: 1 or 2; residues 204-782 of SEQ ID NOs: 1 or 2; residues 206-782 of SEQ ID NOs: 1 or 2; or residues 288-782 of SEQ ID NOs: 1 or 2. In other embodiments, the C-terminal amino acid residues of the mature GAA polypeptide varies, such that the C-terminal amino acid residues is any of residues 816-881, as set forth in SEQ ID NOs: 1 or 2. In certain embodiments, the mature GAA polypeptide comprises or consists of the amino acid sequence of SEQ ID NO: 3 or SEQ ID NO: 4.

In some embodiments, the method comprises use of a chimeric polypeptide that has acid alpha-glucosidase activity. The disclosure contemplates chimeric polypeptides comprising a GAA polypeptide and an internalizing moiety, as described herein, and methods of using any such chimeric polypeptides. In some embodiments, the method comprises use of a chimeric polypeptide that does not comprise the full length, GAA polypeptide set forth in SEQ ID NO: 1. In some embodiments, neither the GAA polypeptide nor the chimeric polypeptide comprise a contiguous amino acid sequence corresponding to the amino acids 1-56 of SEQ ID NO: 1 or 2 (e.g., the GAA polypeptide portion lacks the portion corresponding to amino acids 1-56, preferably 1-57 of SEQ ID NO: 1 or 2, and this region is not present in the chimeric polypeptide). In some embodiments, the chimeric polypeptide comprises a GAA polypeptide that lacks at least a portion of the GAA full linker region, wherein the full linker region corresponds to the amino acids 57-78 of SEQ ID NOs: 1 or 2 (i.e., SEQ ID NO: 31). In some embodiments, neither the GAA polypeptide nor the chimeric polypeptide comprise a contiguous amino acid sequence corresponding to the amino acids 1-60 of SEQ ID NO: 1 or 2 (e.g., the GAA polypeptide portion lacks the portion corresponding to amino acids 1-60 of SEQ ID NO: 1 or 2, and this region is not present in the chimeric polypeptide). In some embodiments, the chimeric polypeptide or GAA polypeptide comprises the amino acid sequence of SEQ ID NO: 21. In some embodiments, the GAA polypeptide, for use in a chimeric polypeptide of the disclosure, comprises amino acids 61-952 of SEQ ID NO:1. In some embodiments, neither the GAA polypeptide nor the chimeric polypeptide comprise a contiguous amino acid sequence corresponding to the amino acids 1-66 of SEQ ID NO: 1 or 2 (e.g., the GAA polypeptide portion lacks the portion corresponding to amino acids 1-66, of SEQ ID NO: 1 or 2, and this region is not present in the chimeric polypeptide). In some embodiments, the chimeric polypeptide or GAA polypeptide comprises the amino acid sequence of SEQ ID NO: 22. In some embodiments, the GAA polypeptide, for use in a chimeric polypeptide of the disclosure, comprises amino acids 67-952 of SEQ ID NO: 1. In some embodiments, neither the GAA polypeptide nor the chimeric polypeptide comprise a contiguous amino acid sequence corresponding to the amino acids 1-69 of SEQ ID NO: 1 or 2 (e.g., the GAA polypeptide portion lacks the portion corresponding to amino acids 1-69 of SEQ ID NO: 1 or 2, and this region is not present in the chimeric polypeptide). In some embodiments, the chimeric polypeptide or GAA polypeptide comprises the sequence of SEQ ID NO: 23. In some embodiments, the GAA polypeptide, for use in a chimeric polypeptide of the disclosure, comprises amino acids 70-952 of SEQ ID NO: 1.

In certain embodiments, the disclosure contemplates chimeric polypeptides comprising the amino acid sequence set forth in SEQ ID NO: 21, 22, or 23, and methods of using such chimeric polypeptides. In other words, the GAA polypeptide portion of such chimeric polypeptides comprises (or consists of) the amino acid sequence set forth in SEQ ID NO: 21, 22, or 23. Also contemplated are variants for use in a chimeric polypeptide of the disclosure, such as variants at least 80%, 85%, 90%, 92%, 93%, 94%, 95%, 96%, 97%, 98%, or 99% identical to SEQ ID NO: 21, 22, or 23.

In certain embodiments, the method comprises use of a chimeric polypeptide comprising or consisting of the amino acid sequence set forth in SEQ ID NO: 11 or 12, or set forth in either of these sequence identifiers but in the absence of one or more epitope tags.

In certain embodiments, the chimeric polypeptide and/or the mature GAA is glycosylated. In certain embodiments, the chimeric polypeptide and/or mature GAA is not glycosylated. In certain embodiments, the mature GAA has a glycosylation pattern that differs from that of naturally occurring human GAA. In certain embodiments, the mature GAA comprises a KFERQ-like motif (SEQ ID NO: 33).

In certain embodiments of any of the foregoing, the internalizing moiety promotes delivery of the chimeric polypeptide into cytoplasm of cells. In certain embodiments, the internalizing moiety promotes delivery of said chimeric polypeptide into muscle cells, such as skeletal or cardiac muscle cells (e.g., promotes delivery into, at least, cytoplasm of muscle cells). In certain embodiments, the internalizing moiety promotes delivery of said chimeric polypeptide into hepatocytes or neurons (e.g., promotes delivery into, at least, cytoplasm of hepatocytes or neurons). It should be noted that when an internalizing moiety is described as promoting delivery into muscle cells, that does not imply that delivery is exclusive to muscle cells. All that is implied is that delivery is somewhat enriched to muscle cells versus one or more other cell types and that transit into cells is not ubiquitous across all cell types.

In certain embodiments, the chimeric polypeptide comprises N-linked oligosaccharide chains modified with M6P residues.

In certain embodiments, the method comprises use of chimeric polypeptides further comprising one or more polypeptide portions that enhance one or more of in vivo stability, in vivo half life, uptake/administration, production, or purification. Exemplary polypeptide portions include epitope tags, such as HA and myc tags, as well as the Fc region of an immunoglobulin or all or a portion of HSA.

In certain embodiments, the method comprises use of a chimeric polypeptide comprising an internalizing moiety comprising an antibody or antigen binding fragment. In certain embodiments, the antibody or antigen binding fragment is a monoclonal antibody or fragment. In certain embodiments, the antibody or antigen binding fragment is human or humanized. In other embodiments, the antibody or antigen binding fragment is murine. Exemplary antigen binding fragments include, scFv, Fv, Fab, and the like. Further exemplary antigen binding fragments comprise a heavy chain variable region (VH) comprising CDR1, CDR2, and CDR3, and a light chain variable region (VL) comprising CDR1, CDR2, and CDR3. When referring to suitable internalizing moieties, they preferably retain the antigen binding characteristics and cell penetrating characteristics when present in the context of the chimeric polypeptide. In some embodiments, the antigen or antigen-binding fragment is a scFv. In other embodiments, the antibody or antigen binding fragment is a Fab. In some embodiments, the GAA polypeptide is fused to the C-terminus of the heavy chain segment of the Fab. In some embodiments, the GAA polypeptide is fused to the C-terminus of the heavy chain segment of the Fab by means of a linker. In some embodiments, the linker comprises the amino acid sequence of SEQ ID NO: 30. In some embodiments, the antibody or antigen binding fragment is an antibody. In some embodiments, the GAA polypeptide portion is fused to the C-terminus of the heavy chain portion of the antibody. In some embodiments, the GAA polypeptide portion is fused to the C-terminus of the heavy chain portion of the antibody by means of a linker. In some embodiments, the linker comprises the amino acid sequence of SEQ ID NO: 30.

In certain embodiments, the method comprises the use of a chimeric polypeptide comprising an antibody or antigen binding fragment thereof that is a monoclonal antibody 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing. In certain embodiments, the antibody or antigen binding fragment thereof is monoclonal antibody 3E10, or a variant thereof that retains cell penetrating activity, or an antigen binding fragment of 3E10 or said 3E10 variant. In some embodiments, the antibody or antigen binding fragment is a chimeric, humanized, or fully human antibody or antigen binding fragment. In some embodiments, the antibody or antigen binding fragment comprises a heavy chain variable domain comprising an amino acid sequence at least 95% identical to SEQ ID NO: 9, or a humanized variant thereof. In some embodiment, the antibody or antigen binding fragment comprises a light chain variable domain comprising an amino acid sequence at least 95% identical to SEQ ID NO: 10, or a humanized variant thereof. In some embodiments, the antibody or antigen binding fragment comprises a heavy chain variable domain comprising the amino acid sequence of SEQ ID NO: 9 and a light chain variable domain comprising the amino acid sequence of SEQ ID NO: 10, or a humanized variant thereof. For any description of an antibody or antigen binding fragment, the disclosure contemplates that the antibody or antigen binding fragment may comprise a heavy chain and a light chain, such as a heavy chain comprising a heavy chain variable domain and a light chain comprising a light chain variable domain. In some embodiments, the antibody or antigen binding fragment comprises a VH CDR1 having the amino acid sequence of SEQ ID NO 13;

a VH CDR2 having the amino acid sequence of SEQ ID NO: 14;

a VH CDR3 having the amino acid sequence of SEQ ID NO: 15;

a VL CDR1 having the amino acid sequence of SEQ ID NO: 16;

a VL CDR2 having the amino acid sequence of SEQ ID NO: 17; and a VL CDR3 having the amino acid sequence of SEQ ID NO: 18, which CDRs are according to Kabat. In some embodiments, the antibody or antigen binding fragment comprises:

a VH CDR1 having the amino acid sequence of SEQ ID NO 24;

a VH CDR2 having the amino acid sequence of SEQ ID NO: 25;

a VH CDR3 having the amino acid sequence of SEQ ID NO: 26;

a VL CDR1 having the amino acid sequence of SEQ ID NO: 27;

a VL CDR2 having the amino acid sequence of SEQ ID NO: 28; and a VL CDR3 having the amino acid sequence of SEQ ID NO: 29, which CDRs are according to the IMGT system.

In certain embodiments, the 3E10 antibody, fragment, or variant comprises a heavy chain comprising an amino acid sequence at least 80%, 85%, 90%, 92%, 95%, 96%, 97%, 98%, 99%, or even 100% identical to SEQ ID NO: 9. In certain embodiments, the 3E10 antibody, fragment, or variant comprises a light chain comprising an amino acid sequence at least 80%, 85%, 90%, 92%, 95%, 96%, 97%, 98%, 99%, or even 100% identical to SEQ ID NO: 10. In certain embodiments, the 3E10 antibody, fragment, or variant comprises a heavy chain comprising an amino acid sequence at least 80%, 85%, 90%, 92%, 95%, 96%, 97%, 98%, 99%, or even 100% identical to SEQ ID NO: 9 and a light chain comprising an amino acid sequence at least 80%, 85%, 90%, 92%, 95%, 96%, 97%, 98%, 99%, or even 100% identical to SEQ ID NO: 10. Is in understood, that these heavy and light chain regions may, in certain embodiments, be connected by a linker (e.g., such as in the context of an scFv—see SEQ ID NO: 11 and 12). Chimeric polypeptides having any combination of the foregoing or following internalizing moieties and mature GAA portions are contemplated. In certain embodiments, the 3E10 antibody, fragment, or variant comprises:

a heavy chain CDR1 having the amino acid sequence of SEQ ID NO: 13, a heavy chain CDR2 having the amino acid sequence of SEQ ID NO: 14, a heavy chain CDR3 having the amino acid sequence of SEQ ID NO: 15, a light chain CDR1 having the amino acid sequence of SEQ ID NO: 16, a light chain CDR2 having the amino acid sequence of SEQ ID NO: 17, and/or a light chain CDR3 having the amino acid sequence of SEQ ID NO: 18, which CDRs are according to Kabat. In some embodiments, the antibody or antigen binding fragment comprises:

a VH CDR1 having the amino acid sequence of SEQ ID NO 24;

a VH CDR2 having the amino acid sequence of SEQ ID NO: 25;

a VH CDR3 having the amino acid sequence of SEQ ID NO: 26;

a VL CDR1 having the amino acid sequence of SEQ ID NO: 27;

a VL CDR2 having the amino acid sequence of SEQ ID NO: 28; and a VL CDR3 having the amino acid sequence of SEQ ID NO: 29, which CDRs are according to the IMGT system.

In certain embodiments, the internalizing moiety comprises a homing peptide. In certain embodiments, the internalizing moiety transits cellular membranes via an equilibrative nucleoside transporter 1 (ENT1), ENT2, ENT3 or ENT4 transporter. In certain embodiments, the internalizing moiety transits cellular membranes via an equilibrative nucleoside transporter 2 (ENT2) transporter.

In certain embodiments, the internalizing moiety is capable of binding polynucleotides. In certain embodiments, the internalizing moiety is capable of binding DNA. In certain embodiments, the internalizing moiety is capable of binding DNA with a $K_D$ of less than 1 µM. In certain embodiments, the internalizing moiety is capable of binding DNA with a $K_D$ of less than 100 nM.

In certain embodiments, the subject in need of treatment is a subject whose Pompe disease has been refractory to one or more previous enzyme replacement therapies.

In certain embodiments, the subject in need of treatment is a human patient with infantile Pompe disease. In certain embodiments, the subject in need of treatment is a human patient with juvenile onset or adult onset Pompe disease. In certain embodiments, the subject in need of treatment is a human patient.

In certain embodiments, an administered chimeric polypeptide is transported to one or more of cytoplasm, lysosomes, and autophagic vesicles of a cell. In certain embodiments, administering the chimeric polypeptide reduces cytoplasmic glycogen accumulation. In certain embodiments, administering the chimeric polypeptide reduces lysosomal glycogen accumulation. In certain embodiments, administering the chimeric polypeptide reduces autophagic vacuole glycogen accumulation.

In certain embodiments, the subject in need thereof is a subject diagnosed with or expected of having Pompe disease. In certain embodiments, the subject in need thereof is a subject whose disease has been refractory to one or more previous enzyme replacement therapies. In certain embodiments, the subject in need thereof is a subject having pathologic cytoplasmic glycogen accumulation prior to initiation of treatment with said chimeric polypeptide. In certain embodiments, the subject in need thereof is a subject diagnosed with Pompe disease greater than six months prior to initiation of treatment with said chimeric polypeptide. In certain embodiments, the subject in need thereof is a subject diagnosed with Pompe disease at least one year prior to initiation of treatment with said chimeric polypeptide. In certain embodiments, the subject in need thereof is a subject in whom the onset of symptoms of Pompe disease occurred greater than six months prior to initiation of treatment with said chimeric polypeptide. In certain embodiments, the subject in need thereof is a subject in whom the onset of symptoms of Pompe disease occurred at least one year prior to initiation of treatment with said chimeric polypeptide. In certain embodiments, the subject in need thereof is a subject with Pompe disease in which pathologic cytoplasmic glycogen accumulation has not yet occurred. In such cases, administration of chimeric polypeptides of the disclosure (e.g., polypeptides that can be delivered into the cytoplasm) is used to prevent pathologic cytoplasmic glycogen accumulation from occurring.

In certain embodiments, the method comprises systemically administering the chimeric polypeptide. In certain embodiments, the method comprises intravenously administering the chimeric polypeptides.

The disclosure contemplates all combinations of any of the foregoing aspects and embodiments, as well as combinations with any of the embodiments set forth in the detailed description and examples. For example, any of the chimeric polypeptides and compositions, including chimeric polypeptides and compositions having any combination of mature GAA portions and an internalizing moiety portions, can be used in any of the methods described herein. Moreover, the disclosure contemplates that, in certain embodiments, while comprising mature GAA, chimeric polypeptides of the disclosure may also include additional contiguous GAA sequence (e.g., the GAA portion comprises a GAA polypeptide that is larger than just mature GAA, but does not include the complete amino acid sequence set forth in SEQ ID NO: 1 and, preferably, does not include a portion corresponding to residues 1-56 or 1-57 of SEQ ID NO: 1 or 2).

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1 is a diagram schematically depicting two different fusion constructs generated. FIG. 1A is a diagram schematically depicting the full-length GAA protein and its different regions, as well as the murine heavy and light chains. Amino acid residues 1-28 correspond to the signal sequence ("SigSeq") region, amino acids 29-56 correspond to the prepro region, and amino acids 57-78 corresponds to the full linker region. Residues 1-56 are highlighted in SEQ ID NO: 1 because, in accordance with Moreland et al., this is the portion of the GAA translation product that is cleaved by a signal peptidase and protease to produce the precursor GAA polypeptide of approximately 110 kilodaltons. FIG. 1B is a diagram schematically depicting the murine 3E10 Fab-GAA fusion construct, while FIG. 1C is a diagram schematically depicting the murine 3E10 mAb-GAA fusion construct.

DETAILED DESCRIPTION OF THE DISCLOSURE

Figures 1A, 1B, 1C:
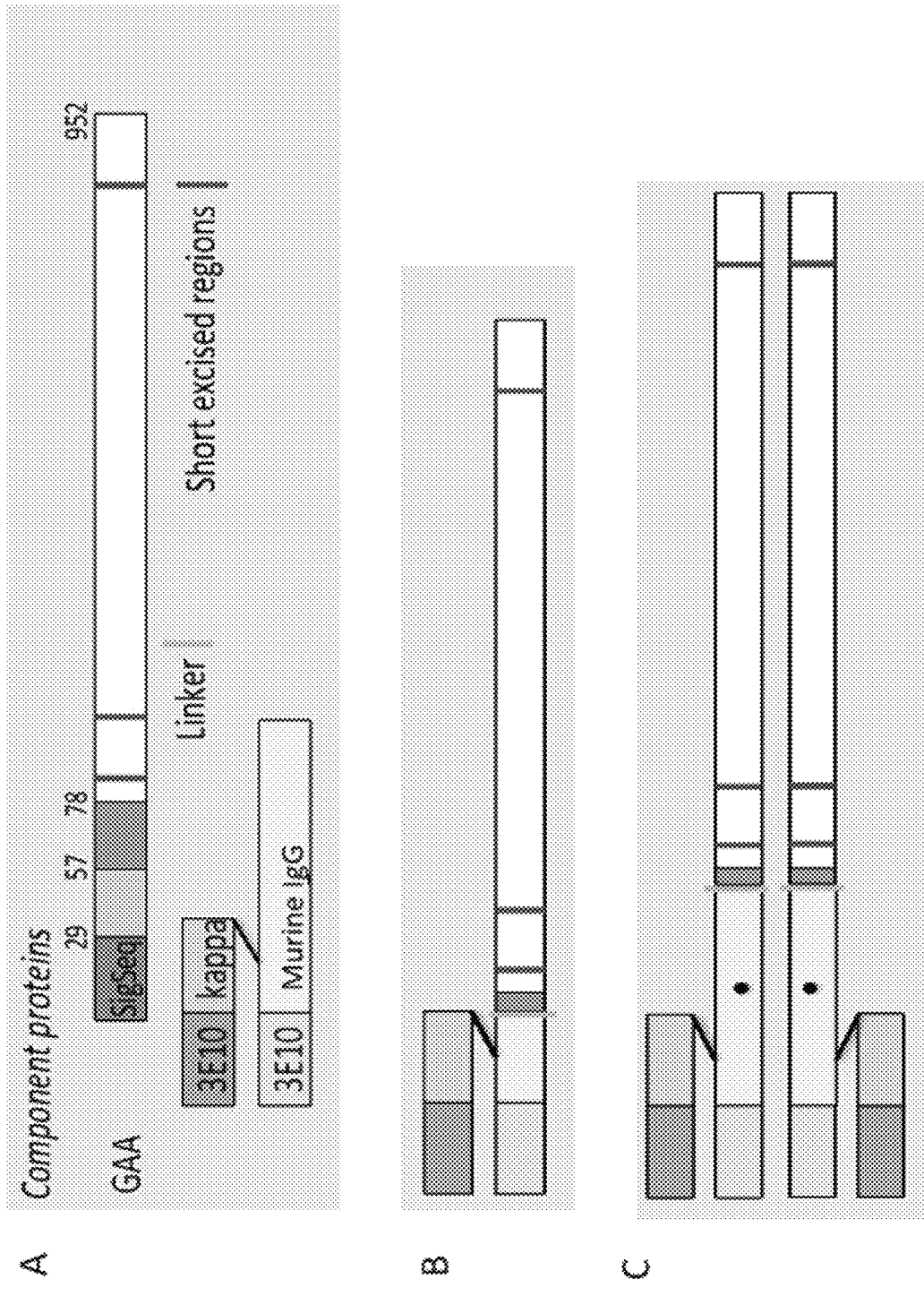

Glycogen is a complex polysaccharide that provides a ready store of glucose to cells in the human body. Glycogen is found principally in the liver, where it is hydrolyzed and released into the bloodstream to provide glucose to other cells, and in muscle, where the glucose resulting from glycogen hydrolysis provides energy for muscle cells. The lysosomal enzyme acid α-glucosidase (GAA) is one of the enzymes that mediates glycogen hydrolysis.

Disruption of glycogen hydrolysis, typically resulting from genetic mutations in genes associated with the process, can lead to glycogen storage disorders. In many cases, the severity of the disease symptoms correlates directly with the extent of the mutation. A debilitating glycogen storage disorder is Glycogen storage disease type II (GSDII or Pompe disease), an autosomal recessive metabolic disorder characterized by a deficiency in the lysosomal enzyme acid α-glucosidase (GAA). Over 300 variants in GAA are known, and disease phenotype depends largely on the amount of residual enzyme activity (Schoser et al., Therapeutic approaches in Glycogen Storage Disease type II (GSDII)/Pompe disease, Neurotherapeutics, 5(4): 569-578, 2008). The most severe form of Pompe disease is an infantile onset form, in which the initial diagnosis occurs between 0-7 months of age. Infantile onset Pompe disease is characterized by hypertrophic cardiomyopathy and profound generalized weakness, and death typically occurs by 1 year of age. Late onset Pompe disease (juvenile and adult onset) is less severe, as residual GAA activity is present. Symptoms appear after 1 year of age or in adulthood, and dysfunction occurs primarily in skeletal and respiratory muscles (Case and Kishnani, Physical therapy management of Pompe disease, Genet Med 8(5): 318-327, 2006). Although juvenile and adult onset Pompe disease are less severe, muscle dysfunction leads to increased and significant disability over time. In some cases, patients become wheelchair and/or ventilator dependent.

In all forms of Pompe disease, dysfunction of GAA impairs the hydrolysis of glycogen in the lysosomes and causes toxic levels of glycogen to accumulate (Geel et al., Pompe disease: Current state of treatment modalities and animal models, *Molecular Genetics and Metabolism*, 92:299-307, 2007). Initially, lysosomes in affected cells increase in size and number. Subsequently, the lysosomes rupture and leak glycogen into the cytoplasm. In muscle fibers, high levels of glycogen accompanied by a lack of glycogen hydrolysis may lead to local starvation and to an increased autophagic response. However, the autophagic vesicles cannot fuse properly with the lysosomes. In addition, cells uptake water to counteract the high concentrations of glycogen, which leads to cell swelling. Over a relatively brief period of time, glycogen accumulates not only in lysosomes but also in the cytoplasm.

Endogenous human GAA is a 952 amino acid protein, encoded by a gene of approximately 28 kb in length. In humans, 3 transcript variants are known (NM_000152.3 which encodes NP000143.2; NM_001079803.1 which encodes NP_001073271.1; and NM_001079804.1 which encodes NP_001073272.1). However, all three transcript variants encode a protein having substantially the same amino acid sequence. Endogenously, the GAA gene encodes a 952 or 957 amino acid polypeptide which includes a signal sequence. This polypeptide is glycosylated in the endoplasmic reticulum and the Golgi apparatus, resulting in a glycosylated precursor with an apparent molecular mass of 110 kDa. There are 7 potential glycosylation sites on the immature precursor, located at residues 140, 233, 390, 470, 652, 882, and 925 of SEQ ID NOs: 1 or 2. The immature precursor is targeted to the lysosomes through mannose-6-phophate receptors (MPRs) and a mannose-6-phosphate (M6P)-independent pathway. The 110 kDa precursor protein is cleaved to give rise to an endosomal intermediate form of GAA having a molecular weight of about 95 kDa. Subsequent N-terminal and C-terminal proteolytic cleavages generate, in the lysosome, mature, active forms of GAA having molecular weights of about 76 kDa and about 70 kDa (Moreland et al., Lysosomal Acid α-Glucosidase Consists of Four Different Peptides Processed from a Single Chain Precursor, Journal of Biological Chemistry, 280(8): 6780-6791, 2005; which is incorporated by reference in its entirety). Owing to heterogeneity in the cleavage sites, alternative starting residues and/or ending residues may define the N and C terminal boundaries of mature GAA polypeptides, such as mature GAA polypeptides for use in the claimed disclosure. For example, the N-terminal residue of a mature GAA polypeptide of about 76 kDa may, in certain embodiments, correspond to residue 122 (Met) or 123 (Gly) of SEQ ID NOs: 1 or 2, while the N-terminal residue of a mature GAA polypeptide of about 70 kDa may, in certain embodiments, correspond to any of residues 204 (Ala), 206 (Ser), or 288 (Gly) of SEQ ID NOs: 1 or 2. Polypeptides having any of the foregoing N-terminal residues may have, for example, a C-terminal residue corresponding to any of residues 816 through 881 of SEQ ID NO:1 or 2, and may be residue 782 of SEQ ID NOs: 1 or 2. Additionally, the C-terminal residue may be any of residues 782 through 816, or residues 782 through 881, inclusive. The molecular weight of the mature GAA polypeptides may be about 76 kDa or about 70 kDa, or may vary according to the foregoing alternative starting and/or ending N and C terminal residues (e.g., corresponding to portions generated due to alternative cleavage).

The FDA approved a version of GAA referred to as alglucosidase alfa (Myozyme, Genzyme Corporation), a recombinant human GAA (rhGAA) analog of the 110 kDa precursor form of GAA, produced in CHO cells. Myozyme is believed to be targeted to the endocytic/lysosomal pathway, and is thought to exert its effects in the lysosome. Myozyme does not appear to treat glycogen accumulation in cytoplasm (Schoser et al., Therapeutic approaches in Glycogen Storage Disease type II (GSDII)/Pompe disease, Neurotherapeutics, 5(4): 569-578, 2008). As noted above, this therapy is believed to target the lysosome and is based on delivery of the immature precursor form of the protein. However, the precursor form of the protein is less active than the 76 kDa mature form of the GAA (Human Molecular Genetics, 7(11): 1815-1824, 1998). Thus, in certain aspects, it may be beneficial to either (i) deliver a mature form of GAA as a chimeric polypeptide, (ii) deliver a GAA polypeptide that, although longer than the mature form is shorter than the 110 kDa precursor form as a chimeric polypeptide, and/or (iii) to deliver a GAA polypeptide with activity of any size as a chimeric polypeptide connected to an internalizing moiety to facilitate delivery of polypeptide into cells, and even into the appropriate subcellular compartment. Without being bound by theory, even if a polypeptide of the disclosure has substantially the same activity as a precursor GAA polypeptide, delivery to the proper cellular location, optionally facilitated by an internalizing moiety that promotes delivery to the cytoplasm, would increase the effective GAA activity delivered to cells. In certain embodiments, the disclosure provides a chimeric polypeptide comprising a GAA polypeptide comprising mature GAA (a GAA portion comprising mature GAA) and an internalizing moiety portion that facilitate deliver into cells. In other words, the disclosure contemplates chimeric polypeptides comprising a GAA polypeptide and an internalizing moiety.

In one aspect, the disclosure provides compositions and methods for cytoplasmic delivery of a mature GAA molecule to affected cells, for example, skeletal muscle cells. Pompe patients exhibit a buildup of glycogen not only in lysosomes but also in cytoplasm and autophagic vesicles. GAA that is targeted to the lysosomes or to endocytic vesicles may not hydrolyze cytoplasmic glycogen. For those patients who begin treatment after the disease has progressed (in some cases, this may be patients who begin treatment after 6 months with GAA dysfunction), it may be too late for lysosome-targeted forms of GAA to clear glycogen effectively from the cells. In contrast, cytoplasm-targeted mature GAA can clear glycogen from the cytoplasm. Not only is mature GAA more active than immature GAA, but mature GAA also remains active at neutral pH, showing approximately 40% activity at neutral pH relative to the acidic environment of the lysosome (Human Molecular Genetics, 11(14), 2002). In fact, although the activity of mature GAA is reduced at neutral pH relative to its activity at acidic pH, even this reduced activity is greater than that of immature GAA—even when assessed under the endogenous acidic conditions of the lysosome. In addition, not only can cytoplasmically delivered mature GAA decrease glycogen accumulation in the cytoplasm, but such GAA may also be incorporated into autophagic vesicles and lysosomes. Without being bound by theory, autophagic vesicles that ultimately fuse with lysosomes may be one of the mechanisms to help promote delivery of cytoplasmic GAA to lysosomes as well. Accordingly, chimeric polypeptides of the disclosure delivered to the cytoplasm are, at least, useful for decreasing glycogen accumulation in cytoplasm and may also help decrease glycogen accumulation in lysosomes and autophagic vesicles.

In certain embodiments, the disclosure provides a chimeric polypeptide comprising a GAA polypeptide and an internalizing moiety, as described herein. Any such chimeric polypeptide of the disclosure can comprise any of the GAA polypeptides described herein associated with any of the internalizing moiety portions described herein, and these chimeric polypeptides can be used in any of the methods of the disclosure.

In certain embodiments, chimeric polypeptides of the disclosure comprise a mature GAA polypeptide and may also contain some additional contiguous amino acid sequence from a GAA polypeptide (but not including the 110 kD precursor polypeptide or the signal sequence of the GAA precursor polypeptide). In other embodiments, the chimeric polypeptides of the disclosure comprise a mature GAA polypeptide but do not include additional contiguous amino acid sequence from a GAA polypeptide other than the mature GAA polypeptide. Thus, the disclosure contemplates chimeric polypeptides in which the GAA portion comprises or consists of a mature GAA polypeptide. Exemplary mature GAA polypeptides having a molecular weight of 70-76 kD are described herein. In certain embodiments, the chimeric polypeptide does not include the signal sequence of the precursor GAA polypeptide. In certain embodiments, the chimeric polypeptide does not include a portion corresponding to residues 1-56 of SEQ ID NO: 1 or 2.

In certain embodiments, the disclosure provides a chimeric polypeptide comprising a GAA polypeptide and an internalizing moiety, as described herein. Any such chimeric polypeptide of the disclosure can comprise any of the GAA polypeptides described herein associated with any of the internalizing moiety portions described herein, and these chimeric polypeptides can be used in any of the methods of the disclosure.

In certain embodiments, the GAA polypeptide portion comprises the amino acid sequence of SEQ ID NO: 21 (e.g., the GAA polypeptide comprises SEQ ID NO: 21), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 21. In certain embodiments, the GAA polypeptide or chimeric polypeptide does not include residues 1-56 of SEQ ID NO: 1. In certain embodiments, the GAA polypeptide or chimeric polypeptide does not include residues 1-60 of SEQ ID NO: 1. In certain embodiments, the GAA polypeptide portion comprises the amino acid sequence of SEQ ID NO: 22 (e.g., the GAA polypeptide comprises SEQ ID NO: 22), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 22. In certain embodiments, the GAA polypeptide or chimeric polypeptide does not include residues 1-66 of SEQ ID NO: 1. In certain embodiments, the GAA polypeptide portion comprises the amino acid sequence of SEQ ID NO: 23 (e.g., the GAA polypeptide comprises SEQ ID NO: 23), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 23. In certain embodiments, the GAA polypeptide or chimeric polypeptide does not include residues 1-69 of SEQ ID NO: 1.

Thus, in certain aspects, the disclosure provides chimeric polypeptides comprising a mature acid alpha-glucosidase (GAA) polypeptide that may be used to treat symptoms associated with Pompe disease.

In certain embodiments, the disclosure provides a chimeric polypeptide comprising (i) a mature GAA polypeptide; and (ii) an internalizing moiety that promotes delivery into cells, such as into cytoplasm of cells. In a particular embodiment, the internalizing moiety helps target delivery of the chimeric polypeptide to muscle cells, such as skeletal muscle cells.

I. GAA Polypeptides

It has been demonstrated that mature GAA polypeptides have enhanced glycogen clearance as compared to the full length, precursor GAA (Bijvoet, et al., 1998, Hum Mol Genet, 7(11): 1815-24), whether at low pH (i.e., the pH of the lysosome or autophagic vacuole) or neutral pH (i.e., the pH of the cytoplasm) conditions. In addition, while mature GAA is a lysosomal protein that has optimal activity at lower pHs, mature GAA retains approximately 40% activity at neutral pH (i.e., the pH of the cytoplasm) (Martin-Touaux et al., 2002, Hum Mol Genet, 11(14): 1637-45). Accordingly, a GAA polypeptide comprising mature GAA is suitable for cytoplasmic delivery, and thus, suitable to address an unaddressed issue of Pompe disease: cytoplasmic glycogen accumulation. However, regardless of whether the GAA portion of a chimeric polypeptide comprises or consists of mature HAA, providing the GAA polypeptide in association with an internalizing moiety of the disclosure facilitates delivery into cells and, in certain embodiments, delivery to cytoplasm.

As used herein, the mature GAA polypeptides include variants, and in particular the mature, active forms of the protein (the active about 76 kDa or about 70 kDa forms or similar forms having an alternative starting and/or ending residue, collectively termed "mature GAA"). The term "mature GAA" refers to a polypeptide having an amino acid sequence corresponding to that portion of the immature GAA protein that, when processed endogenously, has an apparent molecular weight by SDS-PAGE of about 70 kDa to about 76 kDa, as well as similar polypeptides having alternative starting and/or ending residues, as described above. In some embodiments, the GAA polypeptide lacks the signal sequence (amino acids 1-27 of SEQ ID NOs: 1 or 2 or the sequence designated by amino acids 1-56 of SEQ ID NO: 1-56). Exemplary mature GAA polypeptides include polypeptides having residues 122-782 of SEQ ID NOs: 1 or 2; residues 123-782 of SEQ ID NOs: 1 or 2; or residues 204-782 of SEQ ID NOs: 1 or 2. The term "mature GAA" includes polypeptides that are glycosylated in the same or substantially the same way as the endogenous, mature proteins, and thus have a molecular weight that is the same or similar to the predicted molecular weight. The term also includes polypeptides that are not glycosylated or are hyperglycosylated, such that their apparent molecular weight differ despite including the same primary amino acid sequence. Any such variants or isoforms, functional fragments or variants, fusion proteins, and modified forms of the mature GAA polypeptides have at least a portion of the amino acid sequence of substantial sequence identity to the native mature GAA protein, and retain enzymatic activity. In certain embodiments, a functional fragment, variant, or fusion protein of a mature GAA polypeptide comprises an amino acid sequence that is at least 80%, 85%, 90%, 95%, 97%, 98%, 99% or 100% identical to mature GAA polypeptides set forth in one or both of SEQ ID NOs: 3 and 4, or is at least 80%, 85%, 90%, 95%, 97%, 98%, 99% or 100% identical to mature GAA polypeptides corresponding to one or more of: residues 122-782 of SEQ ID NOs: 1 or 2; residues 123-782 of SEQ ID NOs: 1 or 2; or residues 204-782 of SEQ ID NOs: 1 or 2. In some embodiments, the GAA polypeptide is a GAA polypeptide from a non-human species, e.g., mouse, rat, dog, zebrafish, pig, goat, cow, horse, monkey or ape. In some embodiments, the GAA protein comprises the mature form, but not the full-length form, of a bovine GAA protein having the amino acid sequence of SEQ ID NO: 32.

Here and elsewhere in the specification, sequence identity refers to the percentage of residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology.

Methods and computer programs for the alignment of sequences and the calculation of percent identity are well known in the art and readily available. Sequence identity may be measured using sequence analysis software. For example, alignment and analysis tools available through the ExPasy bioinformatics resource portal, such as ClustalW algorithm, set to default parameters. Suitable sequence alignments and comparisons based on pair-wise or global alignment can be readily selected. One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (www.ncbi.nlm.nih.gov/). In certain embodiments, the now current default settings for a particular program are used for aligning sequences and calculating percent identity.

In certain specific embodiments, the chimeric polypeptide comprises a mature GAA polypeptide, such as a GAA polypeptide comprising mature GAA. The mature GAA has an activity that is similar to or substantially equivalent to the activity of endogenous forms of human GAA that are about 76 kDa or about 70 kDa. For example, the mature GAA may be 7-10 fold more active for glycogen hydrolysis than the 110 kDa precursor form, with the comparison being made under the same or similar conditions (e.g. the mature GAA-chimeric polypeptides disclosed herein as compared with endogenous human immature precursor GAA under acidic or neutral pH conditions) The mature GAA polypeptide may be the 76 kDa or the 70 kDa form of GAA, or similar forms that use alternative starting and/or ending residues. As noted in Moreland et al. (Lysosomal Acid α-Glucosidase Consists of Four Different Peptides Processed from a Single Chain Precursor, Journal of Biological Chemistry, 280(8): 6780-6791, 2005), the nomenclature used for the processed forms of GAA is based on an apparent molecular mass as determined by SDS-PAGE. In some embodiments, mature GAA may lack the N-terminal sites that are normally glycosylated in the endoplasmic reticulum. An exemplary mature GAA polypeptide comprises SEQ ID NO: 3 or SEQ ID NO:4. Further exemplary mature GAA polypeptide may comprise or consist of an amino acid sequence corresponding to about: residues 122-782 of SEQ ID NOs: 1 or 2; residues 123-782 of SEQ ID NOs: 1 or 2, such as shown in SEQ ID NO: 3; residues 204-782 of SEQ ID NOs: 1 or 2; residues 206-782 of SEQ ID NOs: 1 or 2; residues 288-782 of SEQ ID NOs: 1 or 2, as shown in SEQ ID NO: 4. Mature GAA polypeptides may also have the N-terminal and or C-terminal residues described above.

In certain embodiments, the chimeric polypeptide does not comprise a full-length GAA polypeptide, but comprises a mature GAA polypeptide and at least a portion of the full-length GAA polypeptide. In other words, in certain embodiments, the chimeric polypeptide comprises a GAA polypeptide and an internalizing moiety. In some embodiments, the chimeric polypeptide does not comprise a full-length GAA polypeptide comprising the amino acid sequence of SEQ ID NO: 1 or 2, but comprises a mature GAA polypeptide sequence comprising the amino acid sequences of SEQ ID NOs: 3 or 4 and at least a portion of the amino acids corresponding to amino acids 1-121 of SEQ ID NOs: 1-2 and/or at least a portion of the amino acids corresponding to amino acids 783-952 of SEQ ID NO: 1. In some embodiments, the chimeric polypeptide does not comprise a full-length GAA polypeptide comprising the amino acid sequence of SEQ ID NO: 1 or 2, but comprises a mature GAA polypeptide sequence comprising the amino acid sequences of SEQ ID NOs: 3 or 4 and at least a portion of the amino acids corresponding to amino acids 783-952 of SEQ ID NO: 1. In some embodiments, the chimeric polypeptide does not comprise a full-length GAA polypeptide comprising the amino acid sequence of SEQ ID NO: 1 or 2, but comprises a mature GAA polypeptide sequence comprising the amino acid sequences of SEQ ID NOs: 3 or 4 and at least a portion of the amino acids corresponding to amino acids 783-957 of SEQ ID NO: 2. These are exemplary of GAA polypeptides.

In certain embodiments, the GAA polypeptide portion (e.g., the portion comprising a GAA polypeptide comprising mature GAA; e.g., a GAA polypeptide) of the chimeric proteins described herein comprise a mature form of GAA but does not comprise a GAA translation product set forth in SEQ ID NO: 1. In some embodiments, neither the GAA polypeptide nor the chimeric polypeptide comprise a contiguous amino acid sequence corresponding to the amino acids 1-27 or 1-56 of SEQ ID NO: 1 or 2. In some embodiments, the GAA polypeptide lacks at least a portion of the GAA full linker region, wherein the full linker region corresponds to amino acids 57-78 of SEQ ID NOs: 1 or 2 (i.e., SEQ ID NO: 31). In some embodiments, the GAA polypeptide does not comprise a contiguous amino acid sequence corresponding to the amino acids 1-60, 1-61, 1-62, 1-63, 1-64, 1-65, 1-66, 1-67, 1-68, 1-69, 1-70, 1-71, 1-72, 1-73, 1-74, 1-75, 1-80, 1-85, 1-90, 1-95, 1-100, 1-105, 1-110, 1-115, 1-120 or 1-121 of SEQ ID NOs: 1 or 2. In particular embodiments, the GAA polypeptide does not comprise a contiguous amino acid sequence corresponding to the amino acids 1-60 of SEQ ID NOs: 1 or 2 (e.g., the chimeric polypeptide comprises a GAA polypeptide portion comprising a GAA polypeptide comprising the amino acid sequence of SEQ ID NO: 21). In other embodiments, the GAA portion does not comprise a contiguous amino acid sequence corresponding to the amino acids 1-66 of SEQ ID NO: 1 or 2 (e.g., the chimeric polypeptide comprises a GAA polypeptide comprising the amino acid sequence of SEQ ID NO: 22). In some embodiments, the GAA portion does not comprise a contiguous amino acid sequence corresponding to the amino acids 1-69 of SEQ ID NO: 1 or 2 (e.g., the chimeric polypeptide comprises a GAA polypeptide portion comprising a GAA polypeptide comprising the amino acid sequence of SEQ ID NO: 23).

In other embodiments, the mature GAA polypeptides may be glycosylated, or may be not glycosylated. For those mature GAA polypeptides that are glycosylated, the glycosylation pattern may be the same as that of naturally-occurring human GAA or may be different. One or more of the glycosylation sites on the precursor GAA protein may be removed in the final mature GAA construct.

Mature GAA has been isolated from tissues such as bovine testes, rat liver, pig liver, human liver, rabbit muscle, human heart, human urine, and human placenta. Mature GAA may also be produced using recombinant techniques, for example by transfecting Chinese hamster ovary (CHO) cells with a vector that expresses full-length human GAA or a vector that expresses mature GAA. Recombinant human GAA (rhGAA) or mature GAA is then purified from CHO-conditioned medium, using a series of ultrafiltration, diafiltration, washing, and eluting steps, as described by Moreland et al. (Lysosomal Acid α-Glucosidase Consists of Four Different Peptides Processed from a Single Chain Precursor, Journal of Biological Chemistry, 280(8): 6780-6791, 2005). Mature GAA fragments may be separated according to methods known in the art, such as affinity chromatography and SDS page.

In certain embodiments, mature GAA, or fragments or variants are human mature GAA.

In certain embodiments, fragments or variants of the mature GAA polypeptides can be obtained by screening polypeptides recombinantly produced from the corresponding fragment of the nucleic acid encoding a mature GAA polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native GAA protein, for example, by testing their ability hydrolyze glycogen and/or treat symptoms of Pompe disease.

In certain embodiments, the present disclosure contemplates modifying the structure of a mature GAA polypeptide for such purposes as enhancing therapeutic or prophylactic efficacy, or stability (e.g., ex vivo shelf life and resistance to proteolytic degradation in vivo). Such modified mature GAA polypeptides are considered functional equivalents of the naturally-occurring GAA polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the GAA biological activity of the resulting molecule. Conservative replacements are those that take place within a family of amino acids that are related in their side chains.

This disclosure further contemplates generating sets of combinatorial mutants of an mature GAA polypeptide, as well as truncation mutants, and is especially useful for identifying functional variant sequences. Combinatorially-derived variants can be generated which have a selective potency relative to a naturally occurring GAA polypeptide. Likewise, mutagenesis can give rise to variants which have intracellular half-lives dramatically different than the corresponding wild-type GAA polypeptide. For example, the altered protein can be rendered either more stable or less stable to proteolytic degradation or other cellular process which result in destruction of, or otherwise inactivation of GAA function. Such variants can be utilized to alter the mature GAA polypeptide level by modulating their half-life. There are many ways by which the library of potential mature GAA variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, mature GAA polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of mature GAA.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the mature GAA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, a mature GAA polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the mature GAA polypeptides.

In certain embodiments, a mature GAA polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified mature GAA polypeptides may contain non-amino acid elements, such as lipids, poly- or mono-saccharide, and phosphates. Effects of such non-amino acid elements on the functionality of a mature GAA polypeptide may be tested for its biological activity, for example, its ability to treat Pompe disease. In certain embodiments, the mature GAA polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In one specific embodiment of the present disclosure, a mature GAA polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the mature GAA protein to carry out the functions associated with wildtype GAA proteins, for example, the hydrolysis of α-1,4- and α-1,6-glycosidic linkages of glycogen, for example lysosomal glycogen. The terms "biological activity", "bioactivity", and "functional" are used interchangeably herein. In certain embodiments, and as described herein, a mature GAA protein or chimeric polypeptide having biological activity has the ability to hydrolyze glycogen. In other embodiments, a mature GAA protein or chimeric polypeptide having biological activity has the ability to lower the concentration of lysosomal and/or cytoplasmic glycogen. In still other embodiments, a mature GAA protein or chimeric polypeptide has the ability to treat symptoms associated with Pompe disease. As used herein, "fragments" are understood to include bioactive fragments (also referred to as functional fragments) or bioactive variants that exhibit "bioactivity" as described herein. That is, bioactive fragments or variants of mature GAA exhibit bioactivity that can be measured and tested. For example, bioactive fragments/functional fragments or variants exhibit the same or substantially the same bioactivity as native (i.e., wild-type, or normal) GAA protein, and such bioactivity can be assessed by the ability of the fragment or variant to, e.g., hydrolyze glycogen in vitro or in vivo. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured, when assessed under the same or substantially the same conditions. In certain embodiments, fragments or variants of the mature GAA polypeptide will preferably retain at least 50%, 60%, 70%, 80%, 85%, 90%, 95% or 100% of the GAA biological activity associated with the native GAA polypeptide, when assessed under the same or substantially the same conditions. In certain embodiments, fragments or variants of the mature GAA polypeptide have a half-life ($t_{1/2}$) which is enhanced relative to the half-life of the native protein. Preferably, the half-life of mature GAA fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native GAA protein, when assessed under the same or substantially the same conditions. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native GAA protein.

With respect to methods of increasing GAA bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, a mature GAA polypeptide may be a fusion protein which further comprises one or more fusion domains. Well-known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His, and c-myc tags. An exemplary His tag has the sequence HHHHHH (SEQ ID NO: 7), and an exemplary c-myc tag has the sequence EQKLISEEDL (SEQ ID NO: 8). It is recognized that any such tags or fusions may be appended to the mature GAA portion of the chimeric polypeptide or may be appended to the internalizing moiety portion of the chimeric polypeptide, or both. In certain embodiments, the chimeric polypeptides comprise a "AGIH" portion (SEQ ID NO: 19) on the N-terminus (or within 10 amino acid residues of the N-terminus) of the chimeric polypeptide, and such chimeric polypeptides may be provided in the presence or absence of one or more epitope tags. In further embodiments, the chimeric polypeptide comprises a serine at the N-terminal most position of the polypeptide. In some embodiments, the chimeric polypeptides comprise an "SAGIH" (SEQ ID NO: 20) portion at the N-terminus (or within 10 amino acid residues of the N-terminus) of the polypeptide, and such chimeric polypeptides may be provided in the presence or absence of one or more epitope tags.

In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the mature GAA polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In some embodiments, a mature GAA polypeptide may be a fusion protein with an Fc region of an immunoglobulin. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Iδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In certain embodiments of any of the foregoing, the GAA portion of the chimeric protein comprises one of the mature forms of GAA, e.g., the 76 kDa fragment, the 70 kDa fragment, similar forms that use an alternative start and/or stop site, or a functional fragment thereof. In certain embodiments, such mature GAA polypeptide or functional fragment thereof retains the ability of to hydrolyze glycogen, as evaluated in vitro or in vivo. Further, in certain embodiments, the chimeric polypeptide that comprises such a mature GAA polypeptide or functional fragment thereof can hydrolyze glycogen. Exemplary bioactive fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length mature GAA polypeptide.

In certain embodiments, the GAA polypeptide portion of the chimeric proteins described herein comprise a mature form of GAA but does not comprise a GAA polypeptide set forth in SEQ ID NO: 1. In some embodiments, the GAA polypeptide lacks at least a portion of the GAA full linker region, wherein the full linker region corresponds to amino acids 57-78 of SEQ ID NOs: 1 or 2 (i.e., SEQ ID NO: 31). In some embodiments, the GAA polypeptide does not comprise a contiguous amino acid sequence corresponding to the amino acids 1-60, 1-61, 1-62, 1-63, 1-64, 1-65, 1-66, 1-67, 1-68, 1-69, 1-70, 1-71, 1-72, 1-73, 1-74, 1-75, 1-80, 1-85, 1-90, 1-95, 1-100, 1-105, 1-110, 1-115, 1-120 or 1-121 of SEQ ID NOs: 1 or 2. In particular embodiments, the GAA polypeptide does not comprise a contiguous amino acid sequence corresponding to the amino acids 1-60 of SEQ ID NOs: 1 or 2 (e.g., the chimeric polypeptide comprises a GAA polypeptide portion comprising a GAA polypeptide comprising the amino acid sequence of SEQ ID NO: 21). In other embodiments, the GAA portion does not comprise a contiguous amino acid sequence corresponding to the amino acids 1-66 of SEQ ID NO: 1 or 2 (e.g., the chimeric polypeptide comprises a GAA polypeptide portion comprising a GAA polypeptide comprising the amino acid sequence of SEQ ID NO: 22). In some embodiments, the GAA portion does not comprise a contiguous amino acid sequence corresponding to the amino acids 1-69 of SEQ ID NO: 1 or 2 (e.g., the chimeric polypeptide comprises a GAA polypeptide portion comprising a GAA polypeptide comprising the amino acid sequence of SEQ ID NO: 23).

In certain embodiments, the disclosure contemplates chimeric proteins where the mature GAA portion is a variant of any of the foregoing mature GAA polypeptides or functional fragments. Exemplary variants have an amino acid sequence at least 90%, 92%, 95%, 96%, 97%, 98%, or at least 99% identical to the amino acid sequence of a native GAA polypeptide or bioactive fragment thereof, and such variants retain the ability of native GAA to hydrolyze glycogen, as evaluated in vitro or in vivo. The disclosure contemplates chimeric proteins and the use of such proteins wherein the GAA portion comprises any of the mature GAA polypeptides, forms, or variants described herein in combination with any internalizing moiety described herein. Exemplary mature GAA polypeptides are set forth in SEQ ID NOs: 3 and 4. Moreover, in certain embodiments, the mature GAA portion of any of the foregoing chimeric polypeptides may, in certain embodiments, by a fusion protein. Any such chimeric polypeptides comprising any combination of GAA portions and internalizing moiety portions, and optionally including one or more linkers, one or more tags, etc., may be used in any of the methods of the disclosure.

II. Internalizing Moieties

As used herein, the term "internalizing moiety" refers to a moiety capable of interacting with a target tissue or a cell type to effect delivery of the attached molecule into the cell (i.e., penetrate desired cell; transport across a cellular membrane; deliver across cellular membranes to, at least, the cytoplasm). Preferably, this disclosure relates to an internalizing moiety which promotes delivery to, for example, muscle cells and liver cells. Internalizing moieties having limited cross-reactivity are generally preferred. In certain embodiments, this disclosure relates to an internalizing moiety which selectively, although not necessarily exclusively, targets and penetrates muscle cells. In certain embodiments, the internalizing moiety has limited cross-reactivity, and thus preferentially targets a particular cell or tissue type. However, it should be understood that internalizing moieties of the subject disclosure do not exclusively target specific cell types. Rather, the internalizing moieties promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof. Other internalizing moieties include for example, homing peptides, fusion proteins, receptors, ligands, aptamers, peptidomimetics, and any member of a specific binding pair. In certain embodiments, the internalizing moiety mediates transit across cellular membranes via an ENT2 transporter. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits cellular membranes via an equilibrative nucleoside transporter 2 (ENT2) transporter. In some embodiments, the internalizing moiety promotes delivery into muscle cells (e.g., skeletal or cardiac muscle). In other embodiments, the internalizing moiety promotes delivery into cells other than muscle cells, e.g., neurons, epithelial cells, liver cells, kidney cells or Leydig cells. For any of the foregoing, in certain embodiments, the internalizing moiety promotes delivery of a chimeric polypeptide into the cytoplasm.

In certain embodiments, the internalizing moiety promotes delivery of a chimeric polypeptide into the cytoplasm. Without being bound by theory, regardless of whether the GAA polypeptide portion of the chimeric polypeptide comprises or consists of mature GAA, this facilitates delivery to the cytoplasm and, optionally, to the lysosome and/or autophagic vesicles.

In certain embodiments, the internalizing moiety is capable of binding polynucleotides. In certain embodiments, the internalizing moiety is capable of binding DNA. In certain embodiments, the internalizing moiety is capable of binding DNA with a $K_D$ of less than 1 μM. In certain embodiments, the internalizing moiety is capable of binding DNA with a $K_D$ of less than 100 nM, less than 75 nM, less than 50 nM, or even less than 30 nM. $K_D$ can be measured using Surface Plasmon Resonance (SPR) or Quartz Crystal Microbalance (QCM), in accordance with currently standard methods. By way of example, a 3E10 antibody or antibody fragment, including an antibody or antibody fragment comprising a VH having the amino acid sequence set forth in SEQ ID NO: 9 and a VL having an amino acid sequence set forth in SEQ ID NO: 10) is know to bind DNA with a $K_D$ of less than 100 nM.

In some embodiments, the internalizing moiety targets a mature GAA polypeptide to muscle cells, and mediates transit of the polypeptide across the cellular membrane into the cytoplasm of the muscle cells.

As used herein, the term "internalizing moiety" refers to a moiety capable of interacting with a target tissue or a cell type. Preferably, this disclosure relates to an internalizing moiety which promotes delivery to, for example, muscle cells and liver cells. Internalizing moieties having limited cross-reactivity are generally preferred. However, it should be understood that internalizing moieties of the subject disclosure do not exclusively target specific cell types. Rather, the internalizing moieties promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof; and other internalizing moieties include for example, homing peptides, fusion proteins, receptors, ligands, aptamers, peptidomimetics, and any member of a specific binding pair. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits cellular membranes via an equilibrative nucleoside transporter 2 (ENT2) transporter. In some embodiments, the internalizing moiety promotes delivery into muscle cells (e.g., skeletal or cardiac muscle). In other embodiments, the internalizing moiety promotes delivery into cells other than muscle cells, e.g., neurons, epithelial cells, liver cells, kidney cells or Leydig cells.

(a) Antibodies

In certain aspects, an internalizing moiety may comprise an antibody, including a monoclonal antibody, a polyclonal antibody, and a humanized antibody. Without being bound by theory, such antibody may bind to an antigen of a target tissue and thus mediate the delivery of the subject chimeric polypeptide to the target tissue (e.g., muscle). In some embodiments, internalizing moieties may comprise antibody fragments, derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In some embodiments, the antibodies or variants thereof may be chimeric, e.g., they may include variable heavy or light regions from the murine 3E10 antibody, but may include constant regions from an antibody of another species (e.g., a human). In some embodiments, the antibodies or variants thereof may comprise a constant region that is a hybrid of several different antibody subclass constant domains (e.g., any combination of IgG1, IgG2a, IgG2b, IgG3 and IgG4).

In certain embodiments, the antibodies or variants thereof, may be modified to make them less immunogenic when administered to a subject. For example, if the subject is human, the antibody may be "humanized"; where the complementarity determining region(s) of the hybridoma-derived antibody has been transplanted into a human monoclonal antibody, for example as described in Jones, P. et al. (1986), *Nature*, 321, 522-525 or Tempest et al. (1991), *Biotechnology*, 9, 266-273. The term humanization and humanized is well understood in the art when referring to antibodies. In some embodiments, the internalizing moiety is any peptide or antibody-like protein having the complementarity determining regions (CDRs) of the 3E10 antibody sequence, or of an antibody that binds the same epitope (e.g., the same target, such as DNA) as 3E10. Also, transgenic mice, or other mammals, may be used to express humanized or human antibodies. Such humanization may be partial or complete.

In certain embodiments, the internalizing moiety comprises the monoclonal antibody 3E10 or an antigen binding fragment thereof. For example, the antibody or antigen binding fragment thereof may be monoclonal antibody 3E10, or a variant thereof that retains cell penetrating activity, or an antigen binding fragment of 3E10 or said 3E10 variant. Additionally, the antibody or antigen binding fragment thereof may be an antibody that binds to the same epitope (e.g., target, such as DNA) as 3E10, or an antibody that has substantially the same cell penetrating activity as 3E10, or an antigen binding fragment thereof. These are exemplary of agents that target ENT2. In certain embodiments, the internalizing moiety is capable of binding polynucleotides. In certain embodiments, the internalizing moiety is capable of binding DNA. In certain embodiments, the internalizing moiety is capable of binding DNA with a $K_D$ of less than 1 μM. In certain embodiments, the internalizing moiety is capable of binding DNA with a $K_D$ of less than 100 nM, less than 75 nM, less than 50 nM, or even less than 30 nM. $K_D$ is determined using SPR or QCM, according to manufacturer's instructions and current practice.

In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced. At this point, 3E10 is generally not produced by the hybridoma but is produced recombinantly. Thus, in the context of the present application, 3E10 antibody will refer to an antibody having the sequence of the hybridoma or comprising a variable heavy chain domain comprising the amino acid sequence set forth in SEQ ID NO: 9 (which has a one amino acid substitution relative to that of the 3E10 antibody deposited with the ATCC, as described herein) and the variable light chain domain comprising the amino acid sequence set forth in SEQ ID NO: 10.

The internalizing moiety may also comprise variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. Such variants include humanized versions of 3E10 or a 3E10 variant. In some embodiments, the light chain or heavy chain may be modified at the N-terminus or C-terminus. Similarly, the foregoing description of variants applies to antigen binding fragments. Any of these antibodies, variants, or fragments may be made recombinantly by expression of the nucleotide sequence(s) in a host cell.

Monoclonal antibody 3E10 has been shown to penetrate cells to deliver proteins and nucleic acids into the cytoplasmic or nuclear spaces of target tissues (Weisbart R H et al., J Autoimmun. 1998 October; 11(5):539-46; Weisbart R H, et al. Mol Immunol. 2003 March; 39(13):783-9; Zack D J et al., J Immunol. 1996 Sep. 1; 157(5):2082-8.). Further, the VH and Vk sequences of 3E10 are highly homologous to human antibodies, with respective humanness z-scores of 0.943 and −0.880. Thus, Fv3E10 is expected to induce less of an anti-antibody response than many other approved humanized antibodies (Abhinandan K R et al., Mol. Biol. 2007 369, 852-862). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 Jun. 10; 195(2):211-9; Weisbart R H et al., J Drug Target. 2005 February; 13(2):81-7; Weisbart R H et al., J Immunol. 2000 Jun. 1; 164(11):6020-6; Hansen J E et al., J Biol Chem. 2007 Jul. 20; 282(29):20790-3). The 3E10 is built on the antibody scaffold present in all mammals; a mouse variable heavy chain and variable kappa light chain. 3E10 gains entry to cells via the ENT2 nucleotide transporter that is particularly enriched in skeletal muscle and cancer cells, and in vitro studies have shown that 3E10 is nontoxic. (Weisbart R H et al., Mol Immunol. 2003 March; 39(13):783-9; Pennycooke M et al., Biochem Biophys Res Commun. 2001 Jan. 26; 280(3):951-9).

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety.

In certain embodiments, the internalizing moiety comprises an antibody or antigen binding fragment comprising an VH domain comprising an amino acid sequence at least 80%, 85%, 90%, 95%, 96%, 97%, 99%, or 100% identical to SEQ ID NO: 9 and/or a VL domain comprising an amino acid sequence at least 85%, 90%, 95%, 96%, 97%, 99%, or 100% identical to SEQ ID NO: 10, or a humanized variant thereof. Of course, such internalizing moieties transit cells via ENT2 and/or bind the same epitope (e.g., target, such as DNA) as 3E10.

In certain embodiments, the internalizing moiety is capable of binding polynucleotides. In certain embodiments, the internalizing moiety is capable of binding DNA. In certain embodiments, the internalizing moiety is capable of binding DNA with a $K_D$ of less than 1 μM. In certain embodiments, the internalizing moiety is capable of binding DNA with a $K_D$ of less than 100 nM.

In certain embodiments, the internalizing moiety is an antigen binding fragment, such as a single chain Fv of 3E10 (scFv) comprising SEQ ID NOs: 9 and 10. In certain embodiments, the internalizing moiety comprises a single chain Fv of 3E10 (or another antigen binding fragment), and the amino acid sequence of the $V_H$ domain is at least 90%, 95%, 96%, 97%, 98%, 99%, or 100% identical to SEQ ID NO: 9, and amino acid sequence of the $V_L$ domain is at least 90%, 95%, 96%, 97%, 98%, 99%, or 100% identical to SEQ ID NO: 10. The variant 3E10 or fragment thereof retains the function of an internalizing moiety. When the internalizing moiety is an scFv, the VH and VL domains are typically connected via a linker, such as a gly/ser linker. The VH domain may be N-terminal to the VL domain or vice versa.

In some embodiments, the internalizing moiety comprises one or more of the CDRs of the 3E10 antibody. In certain embodiments, the internalizing moiety comprises one or more of the CDRs of a 3E10 antibody comprising the amino acid sequence of a $V_H$ domain that is identical to SEQ ID NO: 9 and the amino acid sequence of a $V_L$ domain that is identical to SEQ ID NO: 10. The CDRs of the 3E10 antibody may be determined using any of the CDR identification schemes available in the art. For example, in some embodiments, the CDRs of the 3E10 antibody are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs of the 3E10 antibody are defined according to Chothia et al., 1987, J Mol Biol. 196: 901-917 and Chothia et al., 1989, Nature. 342:877-883. In other embodiments, the CDRs of the 3E10 antibody are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs of the 3E10 antibody are defined according to any of the CDR identification schemes discussed in Kunik et al., 2012, PLoS Comput Biol. 8(2): e1002388. In order to number residues of a 3E10 antibody for the purpose of identifying CDRs according to any of the CDR identification schemes known in the art, one may align the 3E10 antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence.

In certain embodiments, the internalizing moiety comprises at least 1, 2, 3, 4, or 5 of the CDRs of 3E10 as determined using the Kabat CDR identification scheme (e.g., the CDRs set forth in SEQ ID NOs: 13-18). In other embodiments, the internalizing moiety comprises at least 1, 2, 3, 4 or 5 of the CDRs of 3E10 as determined using the IMGT identification scheme (e.g., the CDRs set forth in SEQ ID NOs: 24-29). In certain embodiments, the internalizing moiety comprises all six CDRs of 3E10 as determined using the Kabat CDR identification scheme (e.g., comprises SEQ ID NOs 13-18). In other embodiments, the internalizing moiety comprises all six CDRS of 3E10 as determined using the IMGT identification scheme (e.g., which are set forth as SEQ ID NOs: 24-29). For any of the foregoing, in certain embodiments, the internalizing moiety is an antibody that binds the same epitope (e.g., the same target, such as DNA) as 3E10 and/or the internalizing moiety competes with 3E10 for binding to antigen. Exemplary internalizing moieties target and transit cells via ENT2.

The present disclosure utilizes the cell penetrating ability of 3E10 or 3E10 fragments or variants to promote delivery of mature GAA and GAA polypeptides comprising mature GAA in vivo or into cells in vitro, such as into cytoplasm of cells. 3E10 and 3E10 variants and fragments are particularly well suited for this because of their demonstrated ability to effectively promote delivery to muscle cells, including skeletal and cardiac muscle, as well as diaphragm. Thus, in certain embodiments, 3E10 and 3E10 variants and fragments (or antibodies or antibody fragments that bind the same epitope and/or transit cells via ENT2) are useful for promoting effective delivery into cells in subjects, such as human patients or model organisms, having Pompe Disease or symptoms that recapitulate Pompe Disease. In certain embodiments, chimeric polypeptides in which the internalizing moiety is related to 3E10 are suitable to facilitate delivery of a GAA polypeptide comprising mature GAA to the cytoplasm of cells.

As described further below, a recombinant 3E10 or 3E10-like variant or fragment can be conjugated, linked or otherwise joined to a mature GAA polypeptide, such as to a GAA polypeptide comprising a mature GAA polypeptide. In the context of making chimeric polypeptides to mature GAA, chemical conjugation, as well as making the chimeric polypeptide as a fusion protein is available and known in the art.

Preparation of antibodies or fragments thereof (e.g., a single chain Fv fragment encoded by $V_H$-linker-$V_L$ or $V_L$-linker-$V_H$ or a Fab) is well known in the art. In particular, methods of recombinant production of mAb 3E10 antibody fragments have been described in WO 2008/091911. Further, methods of generating scFv fragments of antibodies or Fabs are well known in the art. When recombinantly producing an antibody or antibody fragment, a linker may be used. For example, typical surface amino acids in flexible protein regions include Gly, Asn and Ser. One exemplary linker is provided in SEQ ID NO: 5 or 6. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4 (SEQ ID NO: 34). Other near neutral amino acids, such as Thr and Ala, can also be used in the linker sequence.

In addition to linkers interconnecting portions of, for example, an scFv, the disclosure contemplates the use of additional linkers to, for example, interconnect the mature GAA portion to the antibody portion of the chimeric polypeptide.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising an peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

(b) Homing Peptides

In certain aspects, an internalizing moiety may comprise a homing peptide which selectively directs the subject chimeric mature GAA polypeptide to a target tissue (e.g., muscle). For example, delivering a chimeric polypeptide to the muscle can be mediated by a homing peptide comprising an amino acid sequence of ASSLNIA (SEQ ID NO: 35). Further exemplary homing peptides are disclosed in WO 98/53804. Homing peptides for a target tissue (or organ) can be identified using various methods well known in the art. Additional examples of homing peptides include the HIV transactivator of transcription (TAT) which comprises the nuclear localization sequence Tat48-60; Drosophila antennapedia transcription factor homeodomain (e.g., Penetratin which comprises Antp43-58 homeodomain 3rd helix); Homo-arginine peptides (e.g., Arg7 peptide-PKC-ε agonist protection of ischemic rat heart ("Arg7" is disclosed as SEQ ID NO: 36)); alpha-helical peptides; cationic peptides ("superpositively" charged proteins). In some embodiments, the homing peptide transits cellular membranes via an equilibrative nucleoside (ENT) transporter. In some embodiments, the homing peptide transits cellular membranes via an ENT1, ENT2, ENT3 or ENT4 transporter. In some embodiments, the homing peptide targets ENT2. In other embodiments, the homing peptide targets muscle cells. The muscle cells targeted by the homing peptide may include skeletal, cardiac or smooth muscle cells. In other embodiments, the homing peptide targets neurons, epithelial cells, liver cells, kidney cells or Leydig cells.

In certain embodiments, the homing peptide is capable of binding polynucleotides. In certain embodiments, the homing peptide is capable of binding DNA. In certain embodiments, the homing peptide is capable of binding DNA with a $K_D$ of less than 1 μM. In certain embodiments, the homing peptide is capable of binding DNA with a $K_D$ of less than 100 nM.

Additionally, homing peptides for a target tissue (or organ) can be identified using various methods well known in the art. Once identified, a homing peptide that is selective for a particular target tissue can be used, in certain embodiments.

An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated two more times. Each round of injection includes, by default, a negative selection component, as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection. Many laboratories have identified the homing peptides that are selective for vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996, Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,699; 6,068,829; 6,174,687; 6,180,084; 6,232,287; 6,296,832; 6,303,573; 6,306,365. Homing peptides that target any of the above tissues may be used for targeting a mature GAA protein to that tissue.

(c) Additional Targeting to Lysosomes and Autophagic Vesicles

A traditional method of targeting a protein to lysosomes is modification of the protein with M6P residues, which directs their transport to lysosomes through interaction of M6P residues and M6PR molecules on the inner surface of structures such as the Golgi apparatus or late endosome. Transport of endogenous GAA to the lysosome depends on M6P and M6PR interaction. There are also forms of M6P independent transport of GAA, as evidenced by normal activity of GAA even in patients with I-cell disease, which manifests with severe deficiencies in other lysosomal enzymes (Wisselar et al., J. Biological Chemistry, 268(3): 2223-2231, 1993). Further evidence of M6P independent transport of GAA is evidenced by a study showing no disruption in lysosomal GAA in muscle-specific M6PR-knockout mice targeting (Wylie et al., 2003, Am J Pathol, 162(1): 321-28). In certain embodiments, chimeric polypeptides of the present disclosure (e.g., polypeptides comprising mature GAA and an internalizing moiety) may further include modification to facilitate additional targeting to the lysosome through M6PRs or in pathways independent of M6PRs. Such targeting moieties may be added, for example, at the N-terminus or C-terminus of a chimeric polypeptide, and via conjugation to 3E10 or mature GAA. In other embodiments, the GAA portion of a chimeric polypeptide comprises all or some of the endogenous sequences to facilitate M6P transport.

In some embodiments, the chimeric polypeptides of the present disclosure are transported to lysosomes via the cellular process of autophagy. Autophagy is a catabolic mechanism that involves cell degradation of unnecessary or dysfunctional cellular components through the lysosomal machinery. During this process, targeted cytoplasmic constituents are isolated from the rest of the cell within vesicles called autophagosomes, which are then fused with lysosomes and degraded or recycled. Uptake of proteins into autophagic vesicles is mediated by the formation of a membrane around the targeted region of a cell and subsequent fusion of the vesicle with a lysosome. Several mechanisms for autophagy are known, including macroautophagy in which organelles and proteins are sequestered within the cell in a vesicle called an autophagic vacuole. Upon fusion with the lysosome, the contents of the autophagic vacuole are degraded by acidic lysosomal hydrolases. In microautophagy, lysosomes engulf cytoplasm directly, and in chaperone-mediated autophagy, proteins with a consensus peptide sequence are bound by a hsc70-containing chaperone-cochaperone complex, which is recognized by a lysosomal protein and translocated across the lysosomal membrane. Autophagic vacuoles have a lysosomal environment (low pH), which is conducive for activity of enzymes such as mature GAA.

Autophagy naturally occurs in muscle cells of mammals (Masiero et al, 2009, Cell Metabolism, 10(6): 507-15). It also has been demonstrated that autophagic degradation is enhanced in Pompe Disease (Malicdan et al., 2008, Neuromuscular Disorders, 18: 521-29; Fukuda et al, 2006, Mol Ther, 14(6): 831-39; Takikita et al, 2009, Autophagy, 5(5): 729-31; Raben et al., 2008, 17(24): 3897-3908). Moreover, the autophagic vacuoles present in Pompe Disease contain glycogen (Malicdan et al., 2008, Neuromuscular Disorders, 18: 521-29). As the autophagic vacuoles take up proteins from the cytoplasm, the chimeric polypeptides of the present disclosure are expected to be taken up by glycogen-containing autophagic vesicles, where the chimeric polypeptides would be free to degrade the glycogen present within those vacuoles. As such, in some embodiments, the chimeric polypeptides are capable of taken up by autophagic vacuoles without addition of any autophagic vacuole-specific targeting motif.

In certain embodiments, the chimeric polypeptides of the present disclosure may further include modification to facilitate additional targeting to autophagic vesicles. One known chaperone-targeting motif is KFERQ-like motif (SEQ ID NO: 33). Accordingly, this motif can be added to chimeric polypeptides as described herein, in order to target the polypeptides for autophagy. Such targeting moieties may be added, for example, at the N-terminus or C-terminus of a chimeric polypeptide, and via conjugation to 3E10 or mature GAA.

M6P residues or chaperone-targeting motifs may be added to the mature GAA polypeptides. Mature GAA polypeptides of the present disclosure may comprise, for example, the 76 kDa form of GAA or the 70 kDa form of GAA or similar forms that use an alternative starting and/or ending site, administered either separately or in combination. For combinations of 70 kDa and 76 kDa forms of GAA, or similar forms of GAA as described herein, the internalizing motifs may be added to either or both of the mature GAA polypeptides.

III. Chimeric Polypeptides

Chimeric polypeptides of the present disclosure can be made in various manners. The chimeric polypeptides may comprise any of the internalizing moiety portions and the mature GAA polypeptide portions disclosed herein (e.g., a GAA polypeptide comprising mature GAA, as described herein). As used herein, chimeric polypeptides of the disclosure comprising (i) a GAA polypeptide portion and (ii) an internalizing moiety portion, such as a GAA polypeptide portion comprising a GAA polypeptide comprising a mature GAA (e.g., the GAA polypeptide portion comprises a GAA polypeptide which includes mature GAA but is longer than the mature GAA generated in vivo by endogenous processing of a GAA precursor. In addition, any of the chimeric polypeptides disclosed herein may be utilized in any of the methods or compositions disclosed herein. In some embodiments, an internalizing moiety (e.g. an antibody or a homing peptide) is linked, directly or indirectly, to any one of the mature GAA polypeptides, fragments or variants disclosed herein. In some embodiments, the chimeric polypeptide does not comprise an: i) immature GAA polypeptide of approximately 110 kDa and/or, ii) immature GAA possessing the signal sequence, i.e., amino acid residues 1-27 of SEQ ID NO: 1 or 2. In other words, the disclosure contemplates chimeric polypeptides in which the chimeric polypeptide comprises a mature GAA polypeptide, but may also include additional polypeptide sequence from a GAA polypeptide, including sequence contiguous with the mature GAA polypeptide (e.g., the GAA polypeptide portion comprises a GAA polypeptide comprising a mature GAA polypeptide sequence). For example, in some embodiments, the chimeric polypeptides comprise a GAA polypeptide comprising the amino acid sequence of any of SEQ ID NOs: 21-23 (e.g., SEQ ID NOs 21-23 are exemplary of GAA polypeptides comprising mature GAA but which also include additional contiguous amino acids of a GAA polypeptide). The disclosure also contemplates embodiments in which the chimeric polypeptide comprises a mature GAA polypeptide but does not include additional GAA polypeptide sequence contiguous with the mature GAA polypeptide portion. Finally, the disclosure contemplates embodiments in which the chimeric polypeptide does not include additional GAA polypeptide portions in addition to the mature GAA polypeptide.

In certain embodiments, it may be desirable to conjugate any of the internalizing moieties described herein with a mature GAA polypeptide (e.g., a GAA polypeptide having the amino acid sequence of SEQ ID NO: 3 or 4) in order to reduce the likelihood that a chimeric polypeptide comprising a larger GAA polypeptide (e.g., a GAA polypeptide having the amino acid sequence of any of SEQ ID NOs: 21-24) is inadvertently cleaved at any of the cleavage sites present in the full-length GAA polypeptide (e.g., cleaving between any of the amino acids corresponding to amino acids 56-57, 77-78, 113-114, 121-122, 200-201, 203-204, 781-782, or 791-792 of SEQ ID NO: 1) by a subject's proteases prior to uptake of the chimeric polypeptide by a targeted cell in the subject.

In certain embodiments, the C-terminus of a mature GAA polypeptide can be linked, directly or indirectly, to the N-terminus of an internalizing moiety (e.g., an antibody, an antibody fragment, or a homing peptide). Alternatively, the C-terminus of an internalizing moiety (e.g., an antibody, an antibody fragment, or a homing peptide) can be linked, directly or indirectly, to the N-terminus of a mature GAA polypeptide. For example, chimeric polypeptides can be designed to place the mature GAA polypeptide at the amino or carboxy terminus of either the antibody heavy or light chain of mAb 3E10. In some embodiments, the GAA polypeptide comprises the amino acid sequence of SEQ ID NO: 22 or 23 fused to the C-terminus of an internalizing moiety. In some embodiments, the GAA polypeptide comprises the amino acid sequence of SEQ ID NO: 22 or 23 fused to the C-terminus of the heavy chain segment of a Fab internalizing moiety. In some embodiments, the GAA polypeptide comprises the amino acid sequence of SEQ ID NO: 22 or 23 fused to the C-terminus of the heavy chain segment of a full-length antibody internalizing moiety.

In certain embodiments, potential configurations include the use of truncated portions of an antibody's heavy and light chain sequences (e.g., mAB 3E10) as needed to maintain the functional integrity of the attached mature GAA polypeptide. Further still, the internalizing moiety can be linked to an exposed internal (non-terminus) residue of mature GAA or a variant thereof. In further embodiments, any combination of the mature GAA-internalizing moiety configurations can be employed, thereby resulting in a mature GAA: internalizing moiety ratio that is greater than 1:1 (e.g., two mature GAA molecules to one internalizing moiety).

The mature GAA polypeptide and the internalizing moiety may be linked directly to each other. Alternatively, they may be linked to each other via a linker sequence, which separates the mature GAA polypeptide and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the mature GAA polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 20 amino acids can be used to provide a suitable separation of functional protein domains, although longer or shorter linker sequences may also be used. The length of the linker sequence separating the mature GAA polypeptide and the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the mature GAA polypeptide to an internalizing moiety can be a constant domain of an antibody (e.g., constant domain of mAb 3E10 or all or a portion of an Fc region of another antibody). In certain embodiments, the linker is a cleavable linker. In certain embodiments, the linker sequence comprises the linker sequence of SEQ ID NO: 30.

In other embodiments, the mature GAA polypeptide or functional fragment thereof may be conjugated or joined directly to the internalizing moiety. For example, a recombinantly conjugated chimeric polypeptide can be produced as an in-frame fusion of the mature GAA portion and the internalizing moiety portion. In certain embodiments, the linker may be a cleavable linker. In any of the foregoing embodiments, the internalizing moiety may be conjugated (directly or via a linker) to the N-terminal or C-terminal amino acid of the mature GAA polypeptide, such as to the N-terminal or C-terminal amino acid of a GAA polypeptide comprising a mature GAA. In other embodiments, the internalizing moiety may be conjugated (directly or indirectly) to an internal amino acid of the mature GAA polypeptide. Note that the two portions of the construct are conjugated/joined to each other. Unless otherwise specified, describing the chimeric polypeptide as a conjugation of the mature GAA portion to the internalizing moiety is used equivalently as a conjugation of the internalizing moiety to the mature GAA portion. Further, unless otherwise specified, conjugation and/or joining refers to either chemical or genetic conjugation.

In certain embodiments, the chimeric polypeptides of the present disclosure can be generated using well-known cross-linking reagents and protocols. For example, there are a large number of chemical cross-linking agents that are known to those skilled in the art and useful for cross-linking the mature GAA polypeptide with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl)cyclohexane-1-carboxylate (SMCC), m-Maleimidobenzoyl-N-hydroxysuccinimide ester (MBS); N-succinimidyl(4-iodoacetyl)aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-$\alpha$-methyl-$\alpha$-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

In some embodiments, the chimeric polypeptide comprises multiple linkers. For example, if the chimeric polypeptide comprises an scFv internalizing moiety, the chimeric polypeptide may comprise a first linker conjugating the GAA to the internalizing moiety, and a second linker in the scFv conjugating the $V_H$ domain (e.g., SEQ ID NO: 9) to the $V_L$ domain (e.g., SEQ ID NO: 10).

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, chimeric polypeptides of the disclosure can be produced by using a universal carrier system. For example, a mature GAA polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, chimeric polypeptides of the disclosure can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of crosslinking for chemical conjugation of mature GAA to an internalizing moiety, a cleavable domain or cleavable linker can be used. Cleavage will allow separation of the internalizing moiety and the mature GAA polypeptide. For example, following penetration of a cell by a chimeric polypeptide, cleavage of the cleavable linker would allow separation of mature GAA from the internalizing moiety.

In certain embodiments, the chimeric polypeptides comprising a GAA polypeptide portion (e.g., a GAA polypeptide comprising a mature GA polypeptide sequence) and an internalizing moiety portion can be generated as a fusion protein containing the GAA polypeptide and the internalizing moiety. In certain embodiments, the chimeric polypeptides of the present disclosure can be generated as a fusion protein containing a mature GAA polypeptide and an internalizing moiety (e.g., an antibody or a homing peptide), expressed as one contiguous polypeptide chain. In certain embodiments, the chimeric polypeptide is generated as a fusion protein that comprises a GAA polypeptide portion and internalizing moiety portion, wherein the GAA polypeptide portion comprises a mature GAA polypeptide and also includes additional polypeptide sequence from a GAA polypeptide, including sequence contiguous with the mature GAA polypeptide. In preparing such fusion protein, a fusion gene is constructed comprising nucleic acids which encode a mature GAA polypeptide and an internalizing moiety, and optionally, a peptide linker sequence to span the mature GAA polypeptide and the internalizing moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the mature GAA polypeptide is conjugated to the N-terminus or C-terminus of the internalizing moiety. Exemplary chimeric polypeptides in which mature GAA polypeptides are conjugated to variant light and heavy chains of Fv3E10 are indicated in SEQ ID NOS: 11 and 12. In certain embodiments, a chimeric polypeptide of the disclosure further comprises, at the N-terminus (at or within 10 amino acid residues of the N-terminus), an amino acid sequence set forth in SEQ ID NO: 19 or 20.

Recombinantly conjugated chimeric polypeptides include embodiments in which the internalizing moiety is N-terminal to the GAA polypeptide and embodiments in which the internalizing moiety is C-terminal to the GAA polypeptide portion.

We note that methods of making fusion proteins recombinantly are well known in the art. Any of the chimeric proteins described herein can readily be made recombinantly. This includes proteins having one or more tags and/or one or more linkers. For example, if the chimeric polypeptide comprises an scFv internalizing moiety, the chimeric polypeptide may comprise a first linker interconnection the internalizing moiety to the mature GAA polypeptide portion, and a second linker in the scFv conjugating the $V_H$ domain. Moreover, in certain embodiments, the chimeric polypeptides comprise a "AGIH" portion (SEQ ID NO: 19) on the N-terminus of the chimeric polypeptide (or within 10 amino acid residues of the N-terminus), and such chimeric polypeptides may be provided in the presence or absence of one or more epitope tags. In further embodiments, the chimeric polypeptide comprises a serine at the N-terminal most position of the polypeptide. In some embodiments, the chimeric polypeptides comprise an "SAGIH" (SEQ ID NO: 20) portion at the N-terminus of the polypeptide (or within 10 amino acid residues of the N-terminus), and such chimeric polypeptides may be provided in the presence or absence of one or more epitope tags.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

Chimeric polypeptides according to the disclosure can be used for numerous purposes. We note that any of the chimeric polypeptides described herein can be used in any of the methods described herein, and such suitable combinations are specifically contemplated.

Chimeric polypeptides described herein can be used to deliver mature GAA polypeptide to cells, particular to a muscle cell. In certain embodiments, chimeric polypeptides deliver mature GAA to liver cells. Thus, the chimeric polypeptides can be used to facilitate transport of mature GAA to cells in vitro or in vivo. By facilitating transport to cells, the chimeric polypeptides improve delivery efficiency, thus facilitating working with mature GAA polypeptide in vitro or in vivo. Further, by increasing the efficiency of transport, the chimeric polypeptides may help decrease the amount of mature GAA needed for in vitro or in vivo experimentation. Moreover, by facilitating delivery to the cytoplasm, the chimeric polypeptides and methods of the disclosure can address the problems associated with cytoplasmic accumulation of glycogen in, for example, Pompe disease.

The chimeric polypeptides can be used to study the function of mature GAA in cells in culture, as well as to study transport of mature GAA. The chimeric polypeptides can be used to identify binding partners for mature GAA in cells, such as transport between cytoplasm and lysosome. The chimeric polypeptides can be used in screens to identify modifiers (e.g., small organic molecules or polypeptide modifiers) of mature GAA activity in a cell. The chimeric polypeptides can be used to help treat or alleviate the symptoms of Pompe disease in humans or in an animal model. The foregoing are merely exemplary of the uses for the subject chimeric polypeptides.

Any of the chimeric polypeptides described herein, including chimeric polypeptides combining any of the features of the GAA polypeptides, internalizing moieties, and linkers, may be used in any of the methods of the disclosure.

IV. GAA-Related Nucleic Acids and Expression

In certain embodiments, the present disclosure makes use of nucleic acids for producing a mature GAA polypeptide (including functional fragments, variants, and fusions thereof), such as for producing GAA polypeptides comprising a mature GAA polypeptide.

In certain specific embodiments, the nucleic acids may further comprise DNA which encodes an internalizing moiety (e.g., an antibody or a homing peptide) for making a recombinant chimeric protein of the disclosure. In certain embodiments, the nucleic acid construct does not encode a chimeric polypeptide comprising a GAA precursor polypeptide of approximately 110 kDa. In certain embodiments, the nucleic acid construct encodes a GAA polypeptide comprising mature GAA but does not encode a GAA polypeptide comprising (i) the amino acid sequence set forth in SEQ ID NO: 1 or 2 or (ii) a portion corresponding to residues 1-27 and/or 1-56 of SEQ ID NO: 1 or 2. All these nucleic acids are collectively referred to as mature GAA nucleic acids because they encode a polypeptide comprising a mature GAA polypeptide and, optionally, additional contiguous portions of a GAA polypeptide.

The nucleic acids may be single-stranded or double-stranded, DNA or RNA molecules. In certain embodiments, the disclosure relates to isolated or recombinant nucleic acid sequences that are at least 80%, 85%, 90%, 95%, 97%, 98%, 99% or 100% identical to a region of a GAA nucleotide sequence (e.g., GenBank Accession No.: NM_000152.3 which encodes NP000143.2; NM_001079803.1 which encodes NP_001073271.1; and NM_001079804.1 which encodes NP_001073272.1) that encodes mature GAA (e.g., mature GAA nucleotide sequence). The nucleotide sequences for GAA are hereby incorporated by reference in their entirety. In further embodiments, the GAA nucleic acid sequences can be isolated, recombinant, and/or fused with a heterologous nucleotide sequence, or in a DNA library.

In certain embodiments, mature GAA nucleic acids also include nucleotide sequences that hybridize under highly stringent conditions to any of the above-mentioned native GAA nucleotide sequences (e.g., GenBank Accession No.: NM_000152.3; NM_001079803.1; and NM_001079804.1), or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the native mature GAA nucleic acids due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant mature GAA nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a mature GAA polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell (e.g., Chines Hamster Ovary cells) to be transformed and/or the type of protein desired to be expressed. Moreover, the vector's copy number, the ability to control that copy number and the expression of any other protein encoded by the vector, such as antibiotic markers, should also be considered.

In some embodiments, a nucleic acid construct, comprising a nucleotide sequence that encodes a mature GAA polypeptide or a bioactive fragment thereof, is operably linked to a nucleotide sequence that encodes an internalizing moiety, wherein the nucleic acid construct encodes a chimeric polypeptide having mature GAA biological activity. In certain embodiments, the nucleic acid constructs may further comprise a nucleotide sequence that encodes a linker.

This disclosure also pertains to a host cell transfected with a recombinant gene which encodes a mature GAA polypeptide or a chimeric polypeptide of the disclosure. The host cell may be any prokaryotic or eukaryotic cell. For example, a mature GAA polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present disclosure further pertains to methods of producing a mature GAA polypeptide or a chimeric polypeptide of the disclosure. For example, a host cell transfected with an expression vector encoding a mature GAA polypeptide or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained cytoplasmically or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., a GAA polypeptide). In a preferred embodiment, the polypeptide is a fusion protein containing a domain which facilitates its purification.

A recombinant mature GAA nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The disclosure contemplates methods of producing chimeric proteins recombinantly, such as described above. Suitable vectors and host cells may be readily selected for expression of proteins in, for example, yeast or mammalian cells. Host cells may express a vector encoding a chimeric polypeptide stably or transiently. Such host cells may be cultured under suitable conditions to express chimeric polypeptide which can be readily isolated from the cell culture medium.

Chimeric polypeptides of the disclosure (e.g., polypeptides comprising a GAA portion comprising mature GAA and an internalizing moiety portion) may be expressed as a single polypeptide chain or as more than one polypeptide chains. An example of a single polypeptide chain is when a GAA portion is fused inframe to an internalizing moiety, which internalizing moiety is an scFv. In certain embodiments, this single polypeptide chain is expressed from a single vectors as a fusion protein.

An example of more than one polypeptide chains is when the internalizing moiety is an antibody or Fab. In certain embodiments, the heavy and light chains of the antibody or Fab may be expressed in a host cell expressing a single vector or two vectors (one expressing the heavy chain and one expressing the light chain). In either case, the GAA polypeptide may be expressed as an inframe fusion to, for example, the C-terminus of the heavy chain such that the GAA polypeptide is appended to the internalizing moiety but at a distance to the antigen binding region of the internalizing moiety.

As noted above, methods for recombinantly expressing polypeptides, including chimeric polypeptides, are well known in the art. Nucleotide sequences expressing a GAA polypeptide, such as a human GAA polypeptide, having a particular amino acid sequence are available and can be used. Moreover, nucleotide sequences expressing an internalizing moiety portion, such as expressing a 3E10 antibody, scFv, or Fab comprising the VH and VL set forth in SEQ ID NO: 9 and 10) are publicly available and can be combined with nucleotide sequence encoding suitable heavy and light chain constant regions. The disclosure contemplates nucleotide sequences encoding any of the chimeric polypeptides of the disclosure, vectors (single vector or set of vectors) comprising such nucleotide sequences, host cells comprising such vectors, and methods of culturing such host cells to express chimeric polypeptides of the disclosure.

V. Methods of Treatment and Other Methods of Use

For any of the methods described herein, the disclosure contemplates the use of any of the chimeric polypeptides and/or compositions described throughout the application. In addition, for any of the methods described herein, the disclosure contemplates the combination of any step or steps of one method with any step or steps from another method.

For example, a chimeric polypeptide of the disclosure comprising a GAA polypeptide portion and an internalizing moiety portion can be used in any of the methods of the disclosure.

In certain embodiments, GAA polypeptides may comprise one of the mature, active forms of the GAA protein, such as the 70 kDa form or the mature 76 kDa form, or a combination of the two. Mature GAA polypeptides may also be administered in combination with the immature 110 kDa form of GAA, in order to target as many organelles and cellular regions/compartments as possible. In addition, mature GAA polypeptides may be administered in combination with and/or following administration of immunotolerizing fragments of GAA, such as small fragments of GAA, and/or immunosuppressive compounds. In some embodiments, the GAA polypeptides comprise a mature GAA polypeptide as well as additional polypeptide sequence from a GAA polypeptide, such as sequence contiguous with the mature GAA polypeptide.

In certain embodiments, the present disclosure provides methods of delivering chimeric polypeptides to cells, including cells in culture (in vitro or ex vivo) and cells in a subject. Delivery to cells in culture, such as healthy cells or cells from a model of disease, have numerous uses. These uses include to identify GAA substrates or binding partners, to evaluate localization and/or trafficking (e.g., to cytoplasm, lysosome, and/or autophagic vesicles), to evaluate enzymatic activity under a variety of conditions (e.g., pH), to assess glycogen accumulation, and the like. In certain embodiments, chimeric polypeptides of the disclosure can be used as reagents to understand GAA activity, localization, and trafficking in healthy or disease contexts.

Delivery to subjects, such as to cells in a subject, have numerous uses. Exemplary therapeutic uses are described below. Moreover, the chimeric polypeptides may be used for diagnostic or research purposes. For example, a chimeric polypeptide of the disclosure may be detectably labeled and administered to a subject, such as an animal model of disease or a patient, and used to image the chimeric polypeptide in the subject's tissues (e.g., localization to muscle and/or liver). Additionally exemplary uses include delivery to cells in a subject, such as to an animal model of disease (e.g., Pompe disease). By way of example, chimeric polypeptides of the disclosure may be used as reagents and delivered to animals to understand GAA bioactivity, localization and trafficking, protein-protein interactions, enzymatic activity, and impacts on animal physiology in healthy or diseased animals.

In certain embodiments, the present disclosure provides methods of treating conditions associated with dysfunction of GAA and Pompe disease. Such conditions include, but are not limited to, aberrant accumulation of glycogen in the lysosomes, cytoplasm, and/or autophagic vesicles of affected cells, for example heart and skeletal muscle cells; cell starvation; disorganization of microtubule structure; increase in number and/or size of lysosomes, rupture of lysosomes; accumulation of cellular debris including autophagic components; disruption of mitochondrial structure; cell swelling; motorneuron disease; muscle weakness; progressive muscle decline; damage to skeletal, respiratory, and/or cardiac muscles; and premature death. Some symptoms of Pompe disease do not manifest until the patients have lived without functional GAA or with diminished levels of GAA for extended periods of time, such as 6 months or longer. In these cases, there has been additional time for glycogen to accumulate not only in the lysosomes but also in cytoplasm and autophagic vacuoles of the patient's cells, triggering disruption of cell and organelle function as described above. When the disease progresses to this stage, traditional enzyme replacement therapies that target GAA to the lysosome may no longer be effective or may be inadequate to treat the condition. Thus, in some embodiments, administration of the mature GAA polypeptides of the present disclosure targets polypeptides comprising the mature GAA to the cytoplasm of affected cells and treats symptoms associated with accumulation of glycogen in the cytoplasm and/or autophagic vacuoles.

These methods involve, in certain embodiments, administering to the individual a therapeutically effective amount of a chimeric polypeptide as described above (e.g., a chimeric polypeptide comprising (i) a GAA portion comprising a GAA polypeptide and (ii) an internalizing moiety portion). These methods are particularly aimed at therapeutic and prophylactic treatments of animals, and more particularly, humans. With respect to methods for Pompe disease, the disclosure contemplates all combinations of any of the foregoing aspects and embodiments, as well as combinations with any of the embodiments set forth in the detailed description and examples.

The present disclosure provides a method of delivering a chimeric polypeptide or nucleic acid construct into a cell via an equilibrative nucleoside transporter (ENT2) pathway, comprising contacting a cell with a chimeric polypeptide or nucleic acid construct. In certain embodiments, the method comprises contacting a cell with a chimeric polypeptide, which chimeric polypeptide comprises a mature GAA polypeptide or bioactive fragment thereof and an internalizing moiety which mediates transport across a cellular membrane via an ENT2 pathway, thereby delivering the chimeric polypeptide into the cell. In certain embodiments, the cell is a muscle cell. The muscle cells targeted using the claimed method may include skeletal, cardiac or smooth muscle cells. In other embodiments, chimeric polypeptides are delivered to liver.

The present disclosure also provides a method of delivering a chimeric polypeptide or nucleic acid construct into a cell via a pathway that allows access to cells other than muscle cells. Other cell types that could be targeted using the claimed method include, for example, liver cells, neurons, epithelial cells, uterine cells, and kidney cells.

Conditions associated with GAA dysfunction and Pompe disease are manifold. Pompe disease is characterized by massive accumulation of glycogen in many tissues, but predominantly skeletal and cardiac muscles, leading to severe dysfunction of the affected tissues. The disease symptoms are progressive. Early onset form of the disease manifests clinically in infants as a combination of hypotonia and generalized muscle weakness, such as a head lag or a "floppy baby" appearance. Cardiomegaly appears in an estimated 92-95% of all infant patients, and heart failure often occurs. Respiratory failure due to weakness of the diaphragm is common, and infants may present with difficulties feeding. Without treatment, infants usually die within the first two years of life.

In juvenile and adult onset forms of the disease, symptoms include musculoskeletal dysfunction, such as muscle weakness, gait abnormalities, muscle pain, frequent falls, difficulty chewing; respiratory complications due to weakening of the diaphragm and other respiratory muscles; cardiac abnormalities such as arrhythmias; and gastrointestinal problems such as difficulty swallowing or feeding. Patients may become dependent on ventilators as the respiratory complications progress, or on wheelchairs as motor function declines.

The terms "treatment", "treating", and the like are used herein to generally mean obtaining a desired pharmacologic and/or physiologic effect. "Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. "Treatment" as used herein covers any treatment of a disease or condition of a mammal, particularly a human, and includes: (a) preventing symptoms of the disease or condition from occurring in a subject which may be predisposed to the disease or condition but has not yet begun experiencing symptoms; (b) inhibiting the disease or condition (e.g., arresting its development); or (c) relieving the disease or condition (e.g., causing regression of the disease or condition, providing improvement in one or more symptoms). For example, "treatment" of Pompe disease encompasses a complete reversal or cure of the disease, or any range of improvement in symptoms and/or adverse effects attributable to Pompe disease. Merely to illustrate, "treatment" of Pompe disease includes an improvement in any of the following effects associated with dysfunction of GAA (or combination thereof): decreased GAA activity (e.g., treatment increases GAA activity), glycogen accumulation in cells (e.g., treatment decreases glycogen accumulation), increased creatine kinase levels, elevation of urinary glucose tetrasaccharide, reduction in heart size, hypertrophic cardiomyopathy, respiratory complications, dependence on a ventilator, muscle dysfunction and/or weakening, loss of motor function, dependence on a wheelchair or other form of mobility assistance, dependence on neck or abdominal support for sitting upright, ultrastructural damage of muscle fibers, loss of muscle tone and function. Improvements in any of these symptoms can be readily assessed according to standard methods and techniques known in the art. Other symptoms not listed above may also be monitored in order to determine the effectiveness of treating Pompe disease. The population of subjects treated by the method of the disclosure includes subjects suffering from the undesirable condition or disease, as well as subjects at risk for development of the condition or disease. In certain embodiments, administering a mature GAA chimeric polypeptide may have any one or more of the following affects: decrease accumulation of glycogen in cytoplasm of cells, decrease accumulation of glycogen in cytoplasm of muscle cells, decrease accumulation of glycogen in cytoplasm of liver cells, decrease accumulation of glycogen in cytoplasm of neurons, decrease accumulation of glycogen in lysosomes of cells, decrease accumulation of glycogen in lysosomes of muscle cells, decrease accumulation of glycogen in lysosomes of liver cells, decrease accumulation of glycogen in lysosomes of neurons, decrease accumulation of glycogen in autophagic vacuoles of cells, decrease accumulation of glycogen in autophagic vacuoles of muscle cells, decrease accumulation of autophagic vacuoles in cytoplasm of liver cells, decrease accumulation of glycogen in autophagic vacuoles of neurons, decrease elevated levels of alanine transaminase (such as elevated levels in serum), decrease elevated levels of aspartate transaminase (such as elevated levels in serum), decrease elevated levels of alkaline phosphatase (such as elevated levels in serum), and/or decrease elevated levels of creatine phosphokinase (such as elevated levels in serum). It should be noted that any of the GAA chimeric polypeptides described above or herein may be used in any of the methods described herein.

In certain embodiments, the subjects in need of treatment are subjects having infantile form of Pompe disease. In other embodiments, the subjects in need of treatment are subjects having juvenile onset By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, one or more chimeric polypeptides of the present disclosure can be administered, together (simultaneously) or at different times (sequentially). In addition, chimeric polypeptides of the present disclosure can be administered alone or in combination with one or more additional compounds or therapies for treating Pompe disease. For example, one or more chimeric polypeptides can be co-administered in conjunction with one or more other therapeutic compounds. In some embodiments, the one or more chimeric polypeptides can be co-administered in conjunction with alglucosidase alfa (Myozyme, Genzyme Corporation). When co-administration is indicated, the combination therapy may encompass simultaneous or alternating administration. In addition, the combination may encompass acute or chronic administration. Optionally, the chimeric polypeptide of the present disclosure and additional compounds act in an additive or synergistic manner for treating Pompe disease. Additional compounds to be used in combination therapies include, but are not limited to, small molecules, polypeptides, antibodies, antisense oligonucleotides, and siRNA molecules. Depending on the nature of the combinatory therapy, administration of the chimeric polypeptides of the disclosure may be continued while the other therapy is being administered and/or thereafter. Administration of the chimeric polypeptides may be made in a single dose, or in multiple doses. In some instances, administration of the chimeric polypeptides is commenced at least several days prior to the other therapy, while in other instances, administration is begun either immediately before or at the time of the administration of the other therapy.

One type of combination therapy makes use of molecules that promote muscle synthesis and/or fat reduction. Molecules such as IGF-1, growth hormones, steroids, β-2 agonists (for example Clenbuterol), and myostatin inhibitors may be administered to patients in order to build muscle tissue and reduce fat infiltration. These molecules may also increase ENT2 levels. Accordingly, the molecules may be administered before treatment with mature GAA polypeptides begins, in between treatments with mature GAA polypeptides, or after treatment with mature GAA polypeptides.

In another example of combination therapy, one or more chimeric polypeptides of the disclosure can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, and the like.

Note that although the chimeric polypeptides described herein can be used in combination with other therapies, in certain embodiments, a chimeric polypeptide is provided as the sole form of therapy. Regardless of whether administrated alone or in combination with other medications or therapeutic regiments, the dosage, frequency, route of administration, and timing of administration of the chimeric polypeptides is determined by a physician based on the condition and needs of the patient.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand GAA bioactivity, localization and trafficking, protein-protein interactions, enzymatic activity, and impacts on animal physiology in healthy or diseases animals.

Chimeric polypeptides may also be used in vitro to evaluate, for example, GAA bioactivity, localization and trafficking, protein-protein interactions, and enzymatic activity in cells in culture, including healthy and GAA deficient cells in culture. The disclosure contemplates that chimeric polypeptides of the disclosure may be used to deliver GAA to cytoplasm, lysosome, and/or autophagic vesicles of cells, including cells in culture.

VI. Gene Therapy

Conventional viral and non-viral based gene transfer methods can be used to introduce nucleic acids encoding polypeptides of mature GAA and or chimeric polypeptides comprising mature GAA in mammalian cells or target tissues. In certain embodiments, the chimeric polypeptides for use in the methods described herein comprise a mature GAA polypeptide, but also include additional polypeptide sequence from a GAA polypeptide, including sequence contiguous with the mature GAA polypeptide. Such methods can be used to administer nucleic acids encoding polypeptides of the disclosure (e.g., mature GAA, including variants thereof, and include chimeric polypeptides) to cells in vitro. The disclosure contemplates that gene transfer methods may be used to deliver nucleic acid encoding any of the chimeric polypeptides of the disclosure or GAA polypeptides. In some embodiments, the nucleic acids encoding mature GAA are administered for in vivo or ex vivo gene therapy uses. In other embodiments, gene delivery techniques are used to study the activity of chiermic polypeptides or GAA polypeptide or to study Pompe disease in cell based or animal models, such as to evaluate cell trafficking, enzyme activity, and protein-protein interactions following delivery to healthy or diseased cells and tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding mature GAA or its variants take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof, all of which are well known in the art.

In applications where transient expression of the polypeptides of the disclosure is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are described in a number of publications, including U.S. Pat. No. 5,173,414; Tratschin et al., *Mol. Cell. Biol.* 5:3251-3260 (1985); Tratschin, et al.; *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells, such as muscle cells.

Gene therapy vectors can be delivered in vivo by administration to an individual patient, by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. For example, cells are isolated from the subject organism, transfected with a nucleic acid (gene or cDNA) encoding, e.g., mature GAA or its variants, and re-infused back into the subject organism (e.g., patient). Various cell types suitable for ex vivo transfection are well known to those of skill in the art.

In certain embodiments, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Stem cells are isolated for transduction and differentiation using known methods.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure, as described herein.

VII. Methods of Administration

Various delivery systems are known and can be used to administer the chimeric polypeptides of the disclosure. Any such methods may be used to administer any of the chimeric polypeptides described herein. Methods of introduction can be enteral or parenteral, including but not limited to, intradermal, intramuscular, intraperitoneal, intramyocardial, intravenous, subcutaneous, pulmonary, intranasal, intraocular, epidural, and oral routes. The chimeric polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

In certain embodiments, the chimeric polypeptide is administered intravenously.

In certain embodiments, it may be desirable to administer the chimeric polypeptides of the disclosure locally to the area in need of treatment (e.g., muscle); this may be achieved, for example, and not by way of limitation, by local infusion during surgery, by means of a catheter, or by means of an implant, the implant being of a porous, non-porous, or gelatinous material, including membranes, such as sialastic membranes, fibers, or commercial skin substitutes.

In another embodiment, such local administration can be to all or a portion of the heart. For example, administration can be by intrapericardial or intramyocardial administration. Similarly, administration to cardiac tissue can be achieved using a catheter, wire, and the like intended for delivery of agents to various regions of the heart.

In another embodiment, local administration is directed to the liver. Glycogen storage and glycogenolysis in the liver affect the availability of glycogen for many other tissues in the body. For example, a venous catheter may be placed in the hepatic portal vein to deliver chimeric polypeptides directly to the liver. In addition, in some embodiments where the internalizing moieties of the chimeric polypeptides show a lower affinity for liver cells than for other cell types, delivery through the hepatic portal vein ensures that adequate concentrations of mature GAA reach the liver cells.

Note that the disclosure contemplates methods in which chimeric polypeptides are administered, at the same or different times, via one than one route of administration. For example, the disclosure contemplates a regimen in which chimeric polypeptides are administered systemically, such as by intravenous infusion, in combination with local administration via the hepatic portal vein.

In other embodiments, the chimeric polypeptides of the disclosure can be delivered in a vesicle, in particular, a liposome (see Langer, 1990, Science 249:1527-1533). In yet another embodiment, the chimeric polypeptides of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric polypeptides of the disclosure can be delivered intravenously.

In certain embodiments, the chimeric polypeptides are administered by intravenous infusion. In certain embodiments, the chimeric polypeptides are infused over a period of at least 10, at least 15, at least 20, or at least 30 minutes. In other embodiments, the chimeric polypeptides are infused over a period of at least 60, 90, or 120 minutes. Regardless of the infusion period, the disclosure contemplates that each infusion is part of an overall treatment plan where chimeric polypeptide is administered according to a regular schedule (e.g., weekly, monthly, etc.).

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

VIII. Pharmaceutical Compositions

In certain embodiments, the subject chimeric polypeptides of the present disclosure are formulated with a pharmaceutically acceptable carrier. One or more chimeric polypeptides can be administered alone or as a component of a pharmaceutical formulation (composition). Any of the chimeric polypeptides described herein may be formulated, as described herein. In certain embodiments, the composition includes two or more chimeric polypeptides of the disclosure, such as a chimeric polypeptide comprising a mature GAA of approximately 70 kDa and a chimeric polypeptide comprising a mature GAA of approximately 76 kDa. The chimeric polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric polypeptides include, for example, those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject chimeric polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more chimeric polypeptide therapeutic agents of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In certain embodiments, methods of the disclosure include topical administration, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject chimeric polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject chimeric polypeptides, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more chimeric polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the chimeric polypeptides of the present disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the chimeric polypeptides of the present disclosure are formulated for subcutaneous administration to human beings.

In certain embodiments, the chimeric polypeptides of the present disclosure are formulated for deliver to the heart, such as for intramyocardial or intrapericaridal delivery.

In certain embodiments, the composition is intended for local administration to the liver via the hepatic portal vein, and the chimeric polypeptides are formulated accordingly.

Note that, in certain embodiments, a particular formulation is suitable for use in the context of deliver via more than one route. Thus, for example, a formulation suitable for intravenous infusion may also be suitable for delivery via the hepatic portal vein. However, in other embodiments, a formulation is suitable for use in the context of one route of delivery, but is not suitable for use in the context of a second route of delivery.

The amount of the chimeric polypeptides of the disclosure which will be effective in the treatment of a tissue-related condition or disease (e.g., Pompe disease) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

IX. Animal Models

Pompe disease has been modeled in animals such as Brahman and Shorthorn cattle, Lapland dog, cats, sheep, and a strain of Japanese quail (Kikuchi et al., Clinical and Metabolic Correction of Pompe Disease by Enzyme Therapy in Acid Maltase-deficient Quail, J. Clin. Invest., 101(4): 827-833, 1998). In addition, mouse models have been developed by targeted disruption of the GAA gene (summarized in Geel et al., Pompe disease: Current state of treatment modalities and animal models, *Molecular Genetics and Metabolism,* 92:299-307, 2007). Briefly, mice possessing a knockout in exon 13 of the GAA gene exhibit glycogen accumulation in lysosomes of liver, heart, and skeletal muscle cells, but remain phenotypically normal (Bijvoet et al., Generalized glycogen storage and cardiomegaly in a knockout mouse model of Pompe disease, Human Molecular Genetics, 7(1): 53-62, 1998). Mice in which exon 6 of the GAA gene was replaced by a neomycin resistance gene flanked by LoxP sites was developed, and lacked GAA function in several tissues. This mouse has also been crossed with Cre-producing mice, and the resultant progeny have abnormal lysosomal glycogen storage in heart and skeletal muscle (Raben et al., Targeted Disruption of the Acid α-Glucosidase Gene in Mice Causes an Illness with Critical Features of Both Infantile and Adult Human Glycogen Storage Disease Type II, J. Biological Chemistry, 272(30): 19086-19092, 1998). A similar mouse model has targeted replacement of exon 14 with a neomycin cassette and is comparable to the neomycin-exon 6 mouse (Raben et al., Modulation of disease severity in mice with targeted disruption of the acid alpha-glucosidase gene, Neuromuscl. Disord. 10: 283-291, 2000). Two additional mouse models have been developed to address issues of immune response: one mouse model in which the exon 6 deletion was targeted to maintain GAA function in the liver while keeping the disease phenotype in other tissues, and one GAA knockout mouse model in SCID mice, which do not produce anti-hGAA antibodies upon administration of hGAA (Raben et al., Induction of tolerance to a recombinant human enzyme, acid alpha-glucosidase, in enzyme deficient knockout mice, Transgenic Research, 12:171-178, 2003; Xu et al., Improved efficacy of gene therapy approaches for Pompe disease using a new, immune-deficient GSD-II mouse model, Gene Therapy, 11:15890-1598, 2004). More recently, a double KO mouse has been developed that pairs deletion of GAA and deletion of glycogen synthase 1 to help determine the effects of decreased glycogen production (Xu et al., Impaired organization and function of myofilaments in single muscle fibers from a mouse model of Pompe disease, *J Appl Physiol* 108: 1383-1388, 2010).

Accordingly, in certain embodiments, the present disclosure contemplates methods of surveying improvements in disease phenotypes using the mature GAA constructs (e.g., the chimeric polypeptides comprising mature GAA) disclosed herein in any one or more animal models, such as the mouse models described herein. By way of example, various parameters can be examined in experimental animals treated with a subject chimeric polypeptide, and such animals can be compared to controls. Exemplary parameters that can be assessed to evaluate potential efficacy include, but are not limited to: increase in lifespan; increase in glycogen clearance, decrease in glycogen accumulation, decrease in alanine transaminase serum levels, decrease in aspartate transaminase serum levels, decrease in alkaline phosphatase serum levels, decrease in creatine phosphokinase serum levels, improved muscle strength, for example in open field and open wire hang paradigms, restoration of function of GAA in lysosomes in liver, skeletal muscle, smooth muscle and/or cardiac muscle. Increase in glycogen clearance and decrease in glycogen accumulation may be assessed, for example, by periodic acid Schiff staining in a biopsy (e.g., muscle, liver or neuronal) from a treated or untreated animal model.

Moreover, once it is established that, for example, 3E10*mature GAA results in an improvement in any one or more of these phenotypes, a complete pharmacokinetic study to determine the effective dose, clearance rate, volume of distribution, and half-life of 3E10-mature GAA can be determined. The PK/PD/TK of the final product can be examined in larger animals such as rats, dogs, and primates.

The above models are exemplary of suitable animal model systems for assessing the activity and effectiveness of the subject chimeric polypeptides and/or formulations. These models have correlations with symptoms of GAA deficiency, and thus provide appropriate models for studying Pompe disease. Activity of the subject chimeric polypeptides and/or formulations can be assessed in any one or more of these models, and the results compared to that observed in wildtype control animals and animals not treated with the chimeric polypeptides. Similarly, the subject chimeric polypeptides can be evaluated using cells in culture, for example, cells prepared from any of the foregoing mutant mice or other animals, as well as wild type cells, such as fibroblasts Additionally, cell free systems may be used to assess, for example, enzymatic activity of the subject chimeric polypeptides. An example of an in vitro assay for testing activity of the chimeric polypeptides disclosed herein would be to treat Pompe cells with or without the chimeric polypeptides and then, after a period of incubation, stain the cells for the presence of glycogen, e.g., by using a periodic acid Schiff (PAS) stain. Another example of an in vitro assay for testing activity of the chimeric polypeptides disclosed herein would be a cell or cell-free assay in which whether the ability of the chimeric polypeptides to hydrolyze 4-methylumbelliferyl-α-D-glucoside as a substrate is assessed.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand GAA bioactivity, localization and trafficking, protein-protein interactions, enzymatic activity, and impacts on animal physiology in healthy or diseases animals.

Chimeric polypeptides may also be used in vitro to evaluate, for example, GAA bioactivity, localization and trafficking, protein-protein interactions, and enzymatic activity in cells in culture, including healthy and GAA deficient cells in culture. The disclosure contemplates that chimeric polypeptides of the disclosure may be used to deliver GAA to cytoplasm, lysosome, and/or autophagic vesicles of cells, including cells in culture.

X. Kits

In certain embodiments, the disclosure also provides a pharmaceutical package or kit comprising one or more containers filled with at least one chimeric polypeptide of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the kit includes additional materials to facilitate delivery of the subject chimeric polypeptides. For example, the kit may include one or more of a catheter, tubing, infusion bag, syringe, and the like. In certain embodiments, the chimeric polypeptide is packaged in a lyophilized form, and the kit includes at least two containers: a container comprising the lyophilized chimeric polypeptide and a container comprising a suitable amount of water, buffer, or other liquid suitable for reconstituting the lyophilized material.

The foregoing applies to any of the chimeric polypeptides, compositions, and methods described herein. The disclosure specifically contemplates any combination of the features of such chimeric polypeptides, compositions, and methods (alone or in combination) with the features described for the various kits described in this section.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1: Chemical Conjugation of 3E10 and Human Mature GAA (mAb3E10*Mature GAA)

Chemical Conjugation

In this example, ten milligrams (10 mg) of an exemplary 3E10 antigen binding fragment comprising a heavy chain variable domain comprising the amino acid sequence of SEQ ID NO: 9 and a light chain variable domain comprising the amino acid sequence of SEQ ID NO: 10 (e.g., such as an scFv in which the VH and VL domains are interconnected via a linker) are conjugated covalently, directly or indirectly, to 76 kDa or 70 kDa mature human GAA, or to a GAA polypeptide comprising a mature human GAA, in a 1/1 molar ratio with the use of two different heterobifunctional reagents, succinimidyl 3-(2-pyridyldithio) propionate and succinimidyl trans-4-(maleimidylmethyl)cyclo-hexane-1-carboxylate. This reaction modifies the lysine residues of 3E10 into thiols and adds thiolreactive maleimide groups to mature GAA (Weisbart R H, et al., J Immunol. 2000 Jun. 1; 164(11): 6020-6). After deprotection, each modified protein is reacted to each other to create a stable thioether bond. Chemical conjugation is performed, and the products are fractionated by gel filtration chromatography. The composition of the fractions is assessed by native and SDS-PAGE in reducing and nonreducing environments. Fractions containing the greatest ratio of 3E10-mature GAA conjugate to free 3E10 and free mature GAA are pooled and selected for use in later studies.

Similarly, conjugates are made in which an antigen binding portion of 3E10 (such as a single chain Fv fragment) or a full length 3E10 or a 3E10 Fab is conjugated to a mature GAA polypeptide, such as mature GAA polypeptide having a molecular weight of approximately 70-76 kDa (e.g., mature, active forms of GAA), or similar forms that use an alternative starting and/or ending residue, or to a GAA polypeptide comprising a mature GAA polypeptide. Other exemplary conjugates include conjugates in which the internalizing moiety is either a full length 3E10 mAb, or variant thereof, or an antigen binding fragment of the foregoing. The foregoing methods can be used to make chemical conjugates that include any combination of GAA portions and internalizing moiety portions, and the foregoing are merely exemplary. Both N-terminal and C-terminal conjugates are made (e.g., conjugates in which the 3E10 portion is N-terminal to the mature GAA portion and conjugates in which the 3E10 portion is C-terminal to the mature GAA portion). Moreover, the experimental approaches detailed herein can be used to evaluate any such chimeric polypeptide or to compare activity amongst chimeric polypeptides.

In Vitro Assessment of Chemically Conjugated 3E10 and Mature GAA

Preparations of conjugated Fv3E10-mature GAA chimeric polypeptides and suitable control polypeptide are summarized in Table 1. The listed chimeric polypeptides are solely for illustrative purposes, and any chimeric polypeptides of the disclosure comprising a GAA polypeptide portion comprising a mature GAA and an internalizing moiety portion are similarly contemplated. Subject chimeric polypeptides are added, for example, to cell cultures and the extent of protein uptake, protein localization and/or GAA enzymatic activity are determined and compared to controls. Similarly, GAA enzymatic activity can be assessed in cell free systems. We note that although, in this example, the internalizing moiety portion and GAA portion are chemically conjugated, each individual portion may be made recombinantly (e.g., by expressing nucleotide sequence encoding the polypeptide in a cell in culture and purifying the expressed polypeptide).

TABLE 1

Exemplary Chemically Conjugated Fv3E10 to human mature GAA

| Group | Polypeptides | |
|---|---|---|
| 1 | Fv3E10*mature GAA (76 kDa) Chemically conjugated | Fv3E10*mature GAA (70 kDa) Chemically conjugated |
| 2 | Fv3E10 & mature GAA (76 kDa) Mixed unconjugated | Fv3E10 & mature GAA (70 kDa) Mixed unconjugated |
| 3 | Fv3E10 alone | Fv3E10 alone |
| 4 | mature GAA(76 kDa) alone | mature GAA(70 kDa) alone |

Note:
Fv3E10 refers to an scFv antigen binding fragment of 3E10, as described above i) Enzymatic Activity of 3E10-Mature GAA GAA enzymatic activity is measured by determining the rate of 3E10-mature GAA catalyzed hydrolysis of a synthetic substrate, p-nitrophenyl-D-α-glucopyranoside, in 50 mM sodium acetate, 0.1% BSA, pH 4.3, as described in McVie et al. (Biochemical and Pharmacological Characterization of Different Recombinant Acid α-Glucosidase Preparations Evaluated for the Treatment of Pompe Disease, Mol Genet Metab., 94(4): 448-455, 2008). The released chromophore, p-nitrophenol, is quantified spectrophotometrically at an alkaline pH (>10.2) at 400 nm. One unit of mature GAA is defined as that amount of activity which resulted in the hydrolysis of 1 μmol of substrate per minute at 37° C. under the assay conditions. Duplicate experiments are performed for Fv3E10 and mature GAA, Fv3E10 alone, or mature GAA alone.

ii) Uptake of 3E10-Mature GAA

Uptake of 3E10-mature GAA is first assessed in COS-7 cells. Previous studies indicate that ENT2 is involved in 3E10 transport across the membrane of COS-7 cells (Hansen et al., J. Biol. Chem., 282: 20790-20793, 2007), and a similar strategy can be used to determine transport of the chimeric 3E10-mature GAA across the membrane. Briefly, purified chimeric polypeptides are prepared in PBS with 10% fetal calf serum; control buffer is PBS with 10% fetal calf serum. 50 μL of control buffer or 3E10-mature GAA is added to COS-7 cells and incubated for 1 hour. The buffer is aspirated, cells are washed, fixed in chilled 100% ethanol, and stained with either an antibody to 3E10 or to GAA.

To demonstrate that muscle cells also uptake Fv3E10-mature GAA polypeptides, the same experiment is conducted in muscle cells. The murine cardiomyocte HL-1 cell line expresses ENT2 (Naydenova et al., Inosine and equilibrative nucleoside transporter 2 contribute to hypoxic preconditioning in the murine cardiomyocyte HL-1 cell line, Am J Physiol. Heart Circ. Physiol., 294 (6):H2687-2692, 2008), and this cell line can be used in place of COS-7 cells in the above experiment.

Human Pompe fibroblasts (TR4192) are grown to confluence in a T-75 flask using MEM/FBS media. The cells are washed with PBS, trypsinized and plated at $1 \times 10^6$ cells/mL in a 96-well plate (100 μL/well). Plates are incubated overnight at 37° C. Following incubation, samples of Fv3E10 and mature GAA, Fv3E10 alone, or mature GAA alone (each assayed in triplicate) are diluted in reduced serum media (MEM/1% FBS) and added to the cells. Following a 24 hour incubation at 37° C., cells are washed and lysed with the addition of PBS/1% Triton X-100 and frozen at −80° C. A protein determination assay using bicinchoninic acid (BCA) and an activity analysis (using 4-methylumbelliferyl-α-D-glucoside as the substrate for GAA) are performed on the cell lysates in order to determine the extent of mature GAA uptake by cells McVie et al. (Biochemical and Pharmacological Characterization of Different Recombinant Acid α-Glucosidase Preparations Evaluated for the Treatment of Pompe Disease, Mol Genet Metab., 94(4): 448-455, 2008).

iii) Immunoblot Detection of Cell-Penetrating 3E10-Mature GAA

Additional tests are performed to determine the uptake of 3E10-mature GAA in muscle fibers isolated from either wildtype or GAA KO mice (Bijvoet et al., Generalized glycogen storage and cardiomegaly in a knockout mouse model of Pompe disease, Human Molecular Genetics, 7(1): 53-62, 1998). White gastrocnemius (G), tibialis anterior (TA) and extensor digitorum longus (EDL) muscles are removed immediately after sacrifice from WT and GAA-KO mice and pinned to Sylgaard coated dishes for fixation with 2% paraformaldehyde in 0.1M phosphate buffer for 1 h, followed by fixation in methanol (−20° C.) for 6 min (Fukuda et al., Autophagy and Mis-targeting of Therapeutic Enzyme in Skeletal Muscle in Pompe Disease, Mol Ther., 14(6): 831-839, 2006). Single fibers are obtained by manual teasing.

Ten to 100 μM of chemically conjugated 3E10-mature GAA, an unconjugated mixture of Fv3E10 and mature GAA, Fv3E10 alone, or mature GAA alone are cultured with the isolated myofibers. The specificity of 3E10-mature GAA for the ENT2 transporter is validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-mature GAA. Eight to 24 hours later the myofibers are collected for immunoblot and Periodic acid-Schiff (PAS) stain for glycogen.

Myofibers are collected and resuspended in 500 ul PBS, lysed, and the supernatants are collected for immunoblot analysis of 3E10 and mature GAA. Epitope tagging will not, in certain embodiments, be employed, therefore the presence of a coincident anti-3E10 and anti-GAA immunoreactive band of ~150-156 kDa (for the full length 3E10+76 kDa GAA or full length 3E10+70 kDa GAA) in 3E10*mature GAA treated cells versus 3E10-alone and GAA-alone controls will constitute successful penetration of chemically conjugated 3E10*mature GAA. Tubulin detection is used as a loading control.

In addition, coverslips of treated cells are washed, fixed in 100% ethanol, rehydrated, and 3E10 and mature GAA are detected with previously described antibodies (Fukuda et al., Autophagy and Mis-targeting of Therapeutic Enzyme in Skeletal Muscle in Pompe Disease, Mol Ther., 14(6): 831-839, 2006).

Respective tissues are frozen, homogenized, and centrifuged to remove insoluble proteins, and protein content of the supernatants are measured by the Bradford assay. Equivalent amounts of protein are electrophoretically separated in a 10% polyacrylamide-SDS gel, are transferred to a nylon membrane, and are probed with a rabbit anti-human GAA polyclonal antibody. Detection of the bound anti-GAA antibody is visualized via the ECL detection system (Amersham Pharmacia).

iv) Tissue Glycogen Content

Myofibers from treated wildtype mice and GAA KO mice are fixed with 5% formaldehyde in 95% ethanol for 5 minutes at room temperature. Glycogen content is evaluated using high resolution light microscopy and computer assisted histomorphometry as described in McVie et al. (Biochemical and Pharmacological Characterization of Different Recombinant Acid α-Glucosidease Preparations Evaluated for the Treatment of Pompe Disease, *Mol Genet Metab.*, 94(4): 448-455, 2008). Briefly, representative samples of muscle tissue are fixed in 3% gluteraldehyde in 0.2 mol/L sodium cacodylate buffer (Electron Microscopy Sciences, Fort Washington, Pa.) and embedded in epon-araldite. One micron sections are stained with Periodic acid-Schiff (PAS) reaction and counterstained with Richardson's solution. This results in high quality tissue preservation in which glycogen is fully retained and appears purple against a blue counterstain of myocyte cytoplasm. One representative field from each slide will be photographed with a Nikon DXM1200 digital camera (Nikon Inc, Instrument Group, Meville, N.Y.) and analyzed using Metamorph Imaging Processing and Analysis software (version 4.6; Universal Imaging Corporation). For each image, glycogen load will be expressed as a percentage of total tissue area.

Example 2: Genetic Construct of Fv 3E10 and Human Mature GAA (Fv3E10-GS3-Mature GAA)

Mammalian expression vectors encoding a genetic fusion of Fv3E10 and one of the two mature forms of human GAA (e.g., such as a GAA polypeptide comprising a mature GAA) (fv3E10-G53-mature GAA, comprising the scFv of mAb 3E10 fused to mature GAA by, for example, the GS3 linker) will be generated. Note that in the examples, we have used "Fv3E10" to refer to an scFv of 3E10. Note that these genetic fusions are also referred to as recombinant conjugates or recombinantly produced conjugates. Other linkers may similarly be used. Further, linkerless fusions where the 3E10 moiety and the mature GAA moiety are directly fused may also be used. Similarly fusions to a portion of a full length antibody or Fab may be made. As with the chemical conjugates, recombinant fusions comprising any of the chimeric polypeptides of the disclosure are contemplated. Recombinantly produced chimeric polypetides may comprises a GAA polypeptide portion, according to the disclosure (e.g., a GAA polypeptide comprising a mature GAA) and an internalizing moiety portion, according to the disclosure.

Additional recombinantly produced conjugates will similarly be made for later testing. By way of non-limiting example: (a) mature GAA-GS3-3E10, (b) 3E10-G53-mature GAA, (c) mature GAA-GS3-Fv3E10, (d) mature GAA-3E10, (e) 3E10-mature GAA, (f) mature GAA-Fv3E10. Note that throughout the examples, the abbreviation Fv is used to refer to a single chain Fv of 3E10. Similarly, mAb 3E10 and 3E10 are used interchangeably. Similarly, mature GAA refers to a mature GAA protein having a molecular weight of from about 70-76 kDa, such as a mature GAA protein having a molecular weight of about 76 kDa or about 70 kDa. These and other chimeric polypeptides can be tested using, for example, the assays detailed herein. Further polypeptides in which the chimeric polypeptides comprise a mature GAA polypeptide, but which polypeptides also include additional contiguous GAA polypeptide sequence (but not the entire 110 kD precursor polypeptide and/or not the signal sequence of the set forth in residues 1-56 or SEQ ID NO: 1 or 2) are also contemplated and can similarly be made and tested.

Create the cDNA for Human GAA and Confirm Activity In Vitro i) Synthesis of the cDNA for GAA The full-length, 3.6 kb human GAA cDNA that encodes a full length, precursor form of human GAA (hGAA cDNA) may be found at http://www.ncbi.nlm.nih.gov/sites/entrez, for example, under GenBank Accession No. NM_000152.3. This cDNA sequences and other transcript variants are hereby incorporated in their entirety. A portion of such a human cDNA sequence corresponding approximately to the region that encodes mature GAA is used herein to generate a recombinant construct. However, it is also contemplated that the full length cDNA can be used.

The mature GAA cDNA along with flanking restriction sites that facilitate cloning into appropriate expression vectors will be synthesized and sequenced by Genscript or other qualified manufacturer of gene sequences. To maximize expression, the mature GAA cDNA will be codon optimized for mammalian and pichia expression. In the event that mammals or pichia prefer a different codon for a given amino acid, we will use the next best candidate to unify the preference. The resulting cDNA is cloned into a CMV-based mammalian expression cassette and large scale preps of the plasmid pCMV-mature GAA will be made using the Qiagen Mega Endo-free plasmid purification kit. To avoid complicating immune responses to the 3E10-GAA protein, epitopes or purification tags are not, in certain embodiments, included. However, conjugates that do include such tags may also be made and tested.

ii) Transfection of Cells In Vitro

A strategy to assess the function of GAA in transfected cells is described above. Ten micrograms of the plasmid pCMV (mock) or pCMV-mature GAA is transfected into 1) COS-7 cells, 2) HL-1 cells, 3) myofibers from wildtype mice, and 4) myofibers from GAA KO mice using commercially available transfection reagents (Table 2). To track the efficiency of transfection, duplicate transfections with plasmids encoding a suitable reporter such as beta-galactosidase or GFP is performed. Forty-eight hours later transfected cells are pelleted by centrifugation resuspended in 500 μl PBS for protein and immunoblot analysis.

TABLE 2

Transfection strategy for pCMV and pCMV-mature GAA

| Group | Cells | Transfected plasmid |
|---|---|---|
| 1 | COS-7 | pCMV (mock) |
| 2 | COS-7 | pCMV-mature GAA (76 kDa or 70 kDa) |
| 3 | HL-1 | pCMV (mock) |
| 4 | HL-1 | pCMV-mature GAA (76 kDa or 70 kDa) |
| 5 | Myofibers from GAA KO mice $6^{neo}/6^{neo}$ | pCMV (mock) |
| 6 | Myofibers from GAA KO mice $6^{neo}/6^{neo}$ | pCMV-mature GAA (76 kDa or 70 kDa) |
| 7 | Myofibers from WT mice | pCMV (mock) |
| 8 | Myofibers from WT mice | pCMV-mature GAA (76 kDa or 70 kDa) | iii) Viral Infection with AAV cDNA Construct

Constructs described above are cloned into an adenovirus vector plasmid, according to methods described in Sun et al., (Enhanced Efficacy of an AAV Vector Encoding Chimeric, Highly-Secreted Acid α-glucosidase in Glycogen Storage Disease Type II, Mol Ther., 14(6): 822-830, 2006). These constructs provide a means to test the cDNA constructs in cells, and/or use constructs in vivo for gene therapy.

Briefly, 293 cells are transfected with an AAV vector plasmid, the AAV packaging plasmid p5E18-VD 2/8, and pAdHelper (Stratagene, La Jolla, Calif.). Cell lysate is harvested 48 hours following infection, freeze-thawed 3 times, and isolated by sucrose cushion pelleting followed by 2 cesium chloride gradient centrifugation steps. AAV stocks are dialyzed against 3 changes of Hanks buffer, and aliquots are stored at −80° C. The number of vector DNA containing-particles is determined by DNase I digestion, DNA extraction, and Southern blot analysis. All viral vector stocks are handled according to Biohazard Safety Level 2 guidelines published by the NIH.

The uptake of chimeric mature GAA is analyzed in (1) COS-7 cells, (2) HL-1 cells, and (3) Pompe disease patient cells as described in Example 1 above. COS-7 cells, HL-1 cells, or fibroblasts from a GSD-II patient are grown in medium containing 10% FBS and incubated for 40 hours with the medium of transfected 293 cells producing chimeric hGAA with activity of 300 nmol·hr·ml. GAA activity and glycogen in cultured patient fibroblasts is analyzed as described above.

iii) Immunoblot Detection of Transfected Human GAA, and Assay of GAA Mediated Hydrolysis of Glycogen.

The same procedures described in Example 1 are utilized. Create and Validate cDNA Fv3E10 Genetically Conjugated to 76 kDa or 70 kDa Forms of GAA i) Synthesis of the cDNA for Fv3E10

The cDNA encoding the mouse Fv3E10 variable light chain linked to the 3E10 heavy chain (SEQ ID NOs: 9-10) contains a mutation in the VH CDR1 that enhances the cell penetrating capacity of the Fv fragment (Zack et al., 1996, J Immunol, 157(5): 2082-8). The 3E10 cDNA is flanked by restriction sites that facilitate cloning in frame with the cDNA coding sequence that corresponds to the amino acid sequences in the mature forms of GAA (SEQ ID NOS: 3-4) or with a GAA polypeptide comprising mature GAA. The constructs are synthesized and sequenced by Genscript or other qualified manufacturer of gene sequences. To maximize expression the 3E10 cDNA will be codon optimized for mammalian and pichia expression. In the event that mammals or pichia prefer a different codon for a given amino acid, the next best candidate to unify the preference will be used. The resulting cDNA will be cloned into a mammalian expression cassette and large scale preps of the plasmid pCMV-3E10-mature GAA will be made using the Qiagen Mega Endo-free plasmid purification kit. The constructs will be tested in 1) COS-7 cells, 2) HL-1 cells, 3) myofibers from wildtype mice, and 4) myofibers from GAA KO mice. A transfection strategy is outlined in Table 3.

TABLE 3

Transfection strategy for pCMV 3E10-GS3-GAA

| Group | Cells | Transfected plasmid |
|---|---|---|
| 1 | COS-7 | pCMV |
| 2 | COS-7 | pCMV-GAA (76 kDa or 70 kDa) |
| 3 | COS-7 | pCMV Fv3E10-GS3-GAA (76 kDa or 70 kDa) |
| 4 | HL-1 | pCMV |
| 5 | HL-1 | pCMV-GAA (76 kDa or 70 kDa) |
| 6 | HL-1 | pCMV Fv3E10-GS3-GAA (76 kDa or 70 kDa) |
| 7 | Myofibers from GAA KO mice $6^{neo}/6^{neo}$ | pCMV |
| 8 | Myofibers from GAA KO mice $6^{neo}/6^{neo}$ | pCMV-GAA (76 kDa or 70 kDa) |
| 9 | Myofibers from GAA KO mice $6^{neo}/6^{neo}$ | pCMV Fv3E10-GS3-GAA (76 kDa or 70 kDa) |
| 10 | Myofibers from WT mice | pCMV (mock) |
| 11 | Myofibers from WT mice | pCMV-GAA (76 kDa or 70 kDa) |
| 12 | Myofibers from WT mice | pCMV Fv3E10-GS3-GAA (76 kDa or 70 kDa) | ii) Transfection of Cells

The strategy to test the expression and glycogen hydrolysis of the 3E10-GS3-mature GAA genetic fusion is described above. The transfection procedure will be the same as described above for transfection of the human GAA cDNA. Transfected cells will be assayed for expression of hGAA and hydrolysis of glycogen.

Production of Recombinant 3E10 Genetically Conjugated to Mature GAA i) Construction of protein expression vectors for pichia. Plasmid construction, transfection, colony selection and culture of Pichia will use kits and manuals per the manufacturer's instructions (Invitrogen). The cDNAs for genetically conjugated 3E10-GS3-mature GAA created and validated as described above will be cloned into two alternative plasmids; PICZ for intracellular expression and PICZalpha for secreted expression. Protein expression from each plasmid is driven by the AOX1 promoter. Transfected pichia will be selected with Zeocin and colonies will be tested for expression of recombinant 3E10-GS3-mature GAA. High expressers will be selected and scaled for purification.

ii) Purification of Recombinant 3E10-GS3-Mature GAA cDNA fusions with mAb 3E10 Fv are ligated into the yeast expression vector pPICZA which is subsequently electroporated into the Pichia pastoris X-33 strain. Colonies are selected with Zeocin (Invitrogen, Carlsbad, Calif.) and identified with anti-his6 antibodies (Qiagen Inc, Valencia, Calif. X-33 cells are grown in baffled shaker flasks with buffered glycerol/methanol medium, and protein synthesis is induced with 0.5% methanol according to the manufacturer's protocol (EasySelect Pichia Expression Kit, Invitrogen, Carlsbad, Calif.). The cells are lysed by two passages through a French Cell Press at 20,000 lbs/in2, and recombinant protein is purified from cell pellets solubilized in 9M guanidine HCl and 2% NP40 by immobilized metal ion affinity chromatography (IMAC) on Ni-NTAAgarose (Qiagen, Valencia, Calif.). Bound protein is eluted in 50 mM NaH2PO4 containing 300 mM NaCl, 500 mM imidazole, and 25% glycerol. Samples of eluted fractions are electrophoresed in 4-20% gradient SDSPAGE (NuSep Ltd, Frenchs Forest, Australia), and recombinant proteins is identified by Western blotting to nitrocellulose membranes developed with cargo-specific mouse antibodies followed by alkaline-phosphatase-conjugated goat antibodies to mouse IgG. Alkaline phosphatase activity is measured by the chromogenic substrate, nitroblue tetrazolium chloride/5-bromo-4-chloro-3-indolylphosphate p-toluidine salt. Proteins are identified in SDS-PAGE gels with GelCode Blue Stain Reagent (Pierce Chemical Co., Rockford, Ill.). Eluted protein is concentrated, reconstituted with fetal calf serum to 5%, and exchange dialyzed 100-fold in 30,000 MWCO spin filters (Millipore Corp., Billerica, Mass.) against McCoy's medium (Mediatech, Inc., Herndon, Va.) containing 5% glycerol. Although in this example a Pichia expression system is illustrated, protein may also be produced in other expression systems, including mammalian expressions systems such as CHO cells. Vectors and methodologies, including contract manufacturing services, for expressing proteins in CHO cells are available, for example, from Lonza.

iii) Quality Assessment and Formulation

Immunoblot against 3E10 and mature GAA is used to verify the size and identity of recombinant proteins, followed by silver staining to identify the relative purity among preparations of 3E10, GAA and 3E10-GS3-mature GAA. Recombinant material is formulated in a buffer and concentration (~0.5 mg/ml).

iv) In Vitro Assessment of Recombinant Material

The activity of 3E10-GS3-mature GAA protein is evaluated using any one or more of the assays detailed in Example 1. Cell penetration and/or enzymatic activity is compared to suitable controls. Moreover, the amount of 3E10-GS3-mature GAA protein needed to alleviate the GAA deficiency is determined using the methods described above. The amounts of GAA activity in mammalian cell-derived and pichia-derived recombinant 3E10-GS3-mature GAA can be tested, for example, on (1) fibroblasts from Pompe disease patients and control patients and (2) myofibers isolated from wildtype and GAA KO mice.

Example 3: In Vivo Assessment of Muscle Targeted GAA in GAA KO Mice

GAA Mouse Models for Evaluation

Several GAA KO mice have been characterized previously: a GAA KO line (Bijvoet et al., Generalized glycogen storage and cardiomegaly in a knockout mouse model of Pompe disease, Human Molecular Genetics, 7(1): 53-62, 1998); a line in which exon 6 has been replaced with loxP-flanked neo gene)($6^{neo}/6^{neo}$) or deleted ($\Delta 6/\Delta 6$) (Raben et al., Targeted Disruption of the Acid α-Glucosidase Gene in Mice Causes an Illness with Critical Features of Both Infantile and Adult Human Glycogen Storage Disease Type II, J. Biological Chemistry, 272(30): 19086-19092, 1998); a mouse line in which exon 14 has been deleted ($\Delta 14^{neo}/\Delta 14^{neo}$) (Raben et al., Modulation of disease severity in mice with targeted disruption of the acid alpha-glucosiase gene, Neuromuscl. Disord. 10: 283-291, 2000); a GAA KO crossed with an inducible hGAA that restores GAA specifically to the liver or muscles (Raben et al., Conditional tissue-specific expression of the acid alpha-glucosidase (GAA) gene in the GAA knockout mouse: implications for therapy, Hum. Molec. Genet. 10: 2039-2047, 2001); a GAA KO crossed with an inducible hGAA mouse line in which expression of GAA in the liver induces immunological tolerance to GAA; (Raben et al., Induction of tolerance to a recombinant human enzyme, acid alpha-glucosidase, in enzyme deficient knockout mice, Transgenic Research, 12:171-178, 2003); a GAA KO/SCID mouse developed to avoid an immune response to GAA in GAA KO mice (Xu et al., Improved efficacy of gene therapy approaches for Pompe disease using a new, immune-deficient GSD-II mouse model, Gene Therapy, 11:15890-1598, 2004); and a double KO mouse of GAA and glycogen synthase 1, in which the effects of decreased glycogen production are studied (Xu et al., Impaired organization and function of myofilaments in single muscle fibers from a mouse model of Pompe disease, J Appl Physiol 108: 1383-1388, 2010).

Of these mice, the $6^{neo}/6^{neo}$ and $\Delta 14^{neo}/\Delta^{neo}$ mice show features of the infantile and adult phenotypes of Pompe disease, while $\Delta 6/\Delta 6$ shows muscle weakness at a later age. All mice show abnormal glycogen storage in heart and skeletal muscle. Accordingly, all of these models serve as appropriate animal models to test the efficacy of 3E10-mature GAA therapy. If the mice develop an immunological response to high doses of 3E10-mature GAA, then one of the immune tolerant mouse models is used.

Selection of Dose of Mature GAA

To determine a dosage that treats glycogen accumulation in skeletal muscle without inducing a harmful immune response, weekly doses of 1 mg/kg, 20 mg/kg, or 100 mg/kg of fv3E10*mature GAA or fv3E10-GS3-mature GAA are injected intravenously to GAA KO mice, followed by assessment of changes in glycogen accumulation. The development of anti-3E10-GAA antibodies are also monitored. Assessment of changes in muscle morphology, muscle fiber strength, and decrease in autophagic vacuoles are also evaluated. The below table illustrates exemplary chimeric polypeptides that can be evaluated. As noted above, any of the chimeric polypeptides of the disclosure are similarly made and tested.

TABLE 4

In vivo dosing plan for chemically and genetically conjugated Fv3E10-GAA

| Group | Mouse Genotype | *Age (months) | # of mice | Treatment | Dose (mg/kg) | *Months of treatment |
|---|---|---|---|---|---|---|
| 1 | GAA KO (or immune tolerant GAA KO line) | 1.5 | 5 | Fv3E10*mature GAA (76 kDa or 70 kDa) Chemically conjugated | 1, 20, or 100 | 3 |
| 2 | GAA KO (or immune tolerant GAA KO line) | 1.5 | 5 | Fv3E10 & mature GAA (76 kDa or 70 kDa) Mixed unconjugated | 1, 20, or 100 | 3 |
| 3 | GAA KO (or immune tolerant GAA KO line) | 1.5 | 5 | Fv3E10-GS3-mature GAA (76 kDa or 70 kDa) Genetic conjugate | 1, 20, or 100 | 3 |
| 4 | GAA KO (or immune tolerant GAA KO line) | 1.5 | 5 | Vehicle | N/A | 3 |
| 5 | WT | 1.5 | 5 | Fv3E10*mature GAA (76 kDa or 70 kDa) Chemically conjugated | 1, 20, or 100 | 3 |
| 6 | WT | 1.5 | 5 | Fv3E10 & mature GAA (76 kDa or 70 kDa) Mixed unconjugated | 1, 20, or 100 | 3 |

TABLE 4-continued

In vivo dosing plan for chemically and genetically conjugated Fv3E10-GAA

| Group | Mouse Genotype | *Age (months) | # of mice | Treatment | Dose (mg/kg) | *Months of treatment |
|---|---|---|---|---|---|---|
| 7 | WT | 1.5 | 5 | Fv3E10-GS3-mature GAA (76 kDa or 70 kDa) Genetic conjugate | 1, 20, or 100 | 3 |
| 8 | WT | 1.5 | 5 | Vehicle | N/A | 3 |

*Animals at 3.5 months or 6 months will also be tested. The months of treatment for these two groups will be 5 months and 1-2 months, respectively.
Note
that chemical or genetic conjugates with 3E10 or Fv3E10 are tested.

Materials and Methods i) Injection of Chemically and Genetically Conjugated 3E10-Mature GAA Fv3E10*mature GAA or Fv3E10-GS3-mature GAA is formulated and diluted in a buffer that is consistent with intravenous injection (e.g. sterile saline solution or a buffered solution of 50 mM Tris-HCl, pH 7.4, 0.15 M NaCl). The amount of 3E10*mature GAA or 3E10-GS3-mature GAA given to each mouse is calculated as follows: dose (mg/kg)×mouse weight (kg)×stock concentration (mg/ml)=volume (ml) of stock per mouse, q.s. to 100 µl with vehicle. Exemplary Fv3E10-GS3-mature GAA chimeric polypeptides for use in these experiments are set forth in SEQ ID NO: 11 or 12.

ii) Measurement of Anti-GAA Antibodies

The immune response to 3E10*mature GAA is determined as described in Raben et al., (Enzyme replacement therapy in the mouse model of Pompe disease, Molecular Genetics and Metabolism, 80: 159-166, 2003). Briefly, blood is drawn from the tail vein at various time points to test the sera for the presence of antibodies to the enzyme by ELISA using 96-well plates. Plates are coated overnight at 4° C. with 5 µg/ml of rhGAA in PBS, incubated with blocking solution (0.1% BSA in PBS) for 2 h at 37° C., and washed with TPBS (0.1% Tween-20 in PBS). Next, the plates are incubated with serial dilutions of test sera (1:100-1:12 800) in triplicates for 1 h at 37° C., washed extensively, incubated for 1 h at 37° C. with 1:12000 goat-anti-mouse IgG-horseradish peroxidase (Southern Biotechnology, Birmingham, Al), washed again, and developed with trimethylbenzidine (TMB) substrate for 15 min at room temperature (KPL, Gaithersburg, Md.). The reaction will be stopped by adding 1N HCL, and the plates will be read in a microplate reader at 450/650 nm.

iii) Tissue Collection and Preparation

Sampled tissues are obtained from the liver, heart, diaphragm, and lower leg skeletal muscles of 3E10*mature GAA, 3E10-GS3-mature GAA, or control untreated mice at 48-72 hour after the final dose of mature enzyme. Tissues are homogenized for measuring GAA activity, extracts are prepared for glycogen measurements and/or tissues are fixed, embedded, and sectioned into 1 µm sections for staining. For electron microscopy of muscle tissues, clamped muscle specimens are fixed in 2.5% buffered glutaraldehyde in 0.1 M sodium cacodylate buffer for 2-4 h at 4° C., stored in 0.1M cacodylate buffer (pH 7.4) and further processed.

iv) Histological Evaluation

For periodic acid Schiff analysis, tissues are fixed in 10% formalin, embedded in paraffin, sectioned, and stained with periodic acid-Schiff (PAS) by standard methods. Additionally, PAS-staining and histochemistry are performed on snap-frozen muscle biopsies. Serial transverse sections (7 µm) are stained with alkaline ATPase (pH 10.4) or NADH-TR by standard methods.

v) Immunohistochemistry

To assess proliferation of lysosomes, as described by Raben et al., (Enzyme replacement therapy in the mouse model of Pompe disease, Molecular Genetics and Metabolism, 80: 159-166, 2003), antibodies to the lysosomal membrane protein LAMP are used. In addition, MPR antibodies are used to determine which histochemical muscle fiber types (as assessed by staining for alkaline ATPase or NADH) are able to clear glycogen most effectively. The following primary antibodies may be used: (FITC)-conjugated rat anti-mouse CD107b (LAMP-2; 1:20) (BD Biosciences, San Diego, Calif.); (FITC)-conjugated rat antimouse CD107a (LAMP-1; 1:20); and rabbit anti-bovine CI-MPR (1:500). Seven micrometer sections of muscle biopsies, snap-frozen in liquid nitrogen cooled isopentane, are collected on cover slips coated with poly-L-lysine and fixed in cold acetone for 10 min followed by re-hydration by immersing in Tris-buffered saline (TBS) for 10 min. Nonspecific binding sites are blocked with 10% horse serum in phosphate-buffered saline (PBS) for 1 h in a humidified chamber at room temperature followed by incubation with primary antibodies for 24 h at 4° C. in a humid chamber. After several washes in PBS, the sections are either mounted with antifade mounting reagent mixture (ProLong Antifade kit, Molecular Probes, Inc., Eugene, Oreg.) or developed with phycoerythrin (PE) conjugated goat F (ab')2 anti-rabbit IgG (H+L) (1:200) secondary antibody (Caltag laboratories, Burlingame, Calif.) (for CI-MPR) prior to mounting.

vi) Tests of Muscle Function

Assessment of motor ability: locomotor activity in an open field is measured in a Digiscan apparatus (Omnitech Electronics), as described in Raben et al. (Enzyme replacement therapy in the mouse model of Pompe disease, Molecular Genetics and Metabolism, 80: 159-166, 2003). Total distance, horizontal activity, and vertical activity is measured by the total number of photocell beam breaks in 10-min intervals during 1-h sessions. Three independent sessions are conducted for each animal over a period of 1 week. Animals are starved overnight before sacrifice. The student's t test will be used for comparisons between the groups. Differences are considered significant at p<0:05.

In addition, all mice are subjected to a battery of motor tests to determine muscle function, as described in Sidman et al., Temporal Neuropathological and Behavioral Phenotype of $6^{neo}/6^{neo}$ Pompe Disease Mice, J Neuropathol Exp Neurol. 67(8): 803-818, 2008). Briefly, all mice are evaluated once a week from 3 months of age. Motor coordination and balance are measured with a rotating rod apparatus (SmartRod, Accuscan Instruments, Columbus, Ohio). For the rocking rotorod test, the rod is programmed to rock backwards and forwards for up to 2.5 sec duration with the overall acceleration in either direction increasing to 25 rpm. Cutoff times are 60 seconds for the accelerating test and 54 seconds for the rocking test. Animals are tested three times on each version of the test with a rest period of at least 5 minutes between measurements. Average fall latency from the rod (or cutoff time) is recorded for each animal and used for statistical analysis. Analyses of locomotor function is performed with the Student t test (Prism GraphPad, San Diego, Calif.). Data are mean±SEM. $p<0.05$ is considered as a statistically significant difference. For the Foot Fault Test, each animal is placed on a wire rack with square holes for 60 seconds and the number of times the paws slipped into the holes is recorded. Each animal is tested twice. Mean values are used for statistical analysis. Strength is measured with a Wire Hang Test. The ability to hang upside down from a wire screen placed 60 cm above a large housing cage is measured as a latency to fall into the cage. A score of zero is assigned to animals that fall immediately and a score of 60 seconds is assigned to animals that did not fall. Cut-off time is 60 seconds. Each animal is tested twice and means are used for statistical analyses. Data will be expressed as mean±SEM. For two groups the Student t test is used; for more than two group comparisons, one-way ANOVA is used followed by the post hoc Bonferroni multiple comparison test.

vii) Assessing Serum Enzyme Levels

Blood is collected from tail veins or from the venous sinus from each mouse every three to four days for the duration of the study. Samples are tested for levels of alanine transaminase, aspartate transaminase, alkaline phosphatase, and/or creatine phosphokinase. Decrease in the elevated levels of one or more of these enzymes is indicative of reduction of some of the pathological effects of cytoplasmic glycogen accumulation.

viii) Survival Assessment

Those treated and untreated diseased and control mice that are not sacrificed in the experiments described above will be monitored in a survival study. Specifically, the disease state, treatment conditions and date of death of the animals are recorded. A survival curve will be prepared based on the results of this study.

Example 4: Trials of 3E10*Mature GAA and 3E10-GS3-Mature GAA in Human Pompe Disease Patients Following the examples of clinical trials in infantile-onset Pompe disease patients and late-onset Pompe patients (summarized by Schoser et al., Therapeutic approaches in Glycogen Storage Disease type II (GSDII)/Pompe disease, Neurotherapeutics, 5(4): 569-578, 2008), 3E10*mature GAA and/or 3E10-G53-mature GAA is administered intravenously to patients in, for example, dosages of up to 40 mg/kg weekly (such as chimeric polypeptides comprising a GAA portion comprising mature GAA and an internalizing moiety portion). Patients may receive 10 mg/kg weekly for 52 weeks, or may receive 5-20 mg/kg weekly or biweekly for 153 weeks. Patients are monitored for tolerance of the therapeutic and for improvements in glycogen clearance, tissue morphology, motor function, and/or cardiac function. Muscle biopsies are taken, and analyzed by high-resolution light microscopy, digital histomorphometry, electron microscopy, capillary density, fiber type analysis, and/or confocal microscopy. The left ventricular mass index (LVMI) of infants is monitored. Motor milestones, for example walking or sitting upright, of infants and toddlers undergoing treatment is compared with age-matched subjects not suffering from Pompe disease. Dependence on ventilator support for breathing is also be monitored.

The foregoing experimental schemes will similarly be used to evaluate other chimeric polypeptides. By way of non-limiting example, this scheme will be used to evaluate chemical conjugates and fusion proteins having a GAA portion (or a fragment thereof) and an internalizing moiety portion. By way of further example, the foregoing methods may also be used to evaluate use of compositions comprising a mixture of two or more conjugates, such as a mixture of 3E10*mature GAA (70 kDa) and 3E10*mature GAA (76 kDa).

The particular chimeric polypeptides described above for evaluation in examples 1-4 are exemplary of the chimeric polypeptides of the disclosure—any of which can be made and evaluated using, for example, the methods described in examples 1-4. By way of example, chemical and genetic conjugates in the presence or absence of a linker are made and tested. Conjugates in which the mature GAA moiety is located N-terminal to the internalizing moiety, as well as conjugates in which the mature GAA moiety is located C-terminal to the internalizing moiety are made and test. Any of a range of internalizing moieties and linker moieties are used.

By way of non-limiting example the following chimeric polypeptides are made and tested: (a) mature GAA-GS3-3E10, (b) 3E10-G53-mature GAA, (c) mature GAA-GS3-Fv3E10, (d) mature GAA-3E10, (e) 3E10-mature GAA, (f) mature GAA-Fv3E10, (g) 3E10*mature GAA, (h) mature GAA*3E10, (i) internalizing moiety*mature GAA, (j) mature GAA*internalizing moiety, (k) internalizing moiety-GS3-mature GAA, (l) mature GAA-GS3-internalizing moiety. Note that throughout the examples, the abbreviation Fv is used to refer to a single chain Fv of 3E10. Similarly, mAb 3E10 and 3E10 are used interchangeably. Similarly, mature GAA refers to a mature GAA protein having a molecular weight of from about 70-76 kDa, such as a mature GAA protein having a molecular weight of about 76 kDa or about 70 kDa. These and other chimeric polypeptides can be tested using, for example, the assays detailed herein.

By way of further example, the foregoing methods may also be used to evaluate use of compositions comprising a mixture of two or more conjugates, such as a mixture of 3E10*mature GAA (70 kDa) and 3E10*mature GAA (76 kDa).

Example 5: Generation and Characterization of 3E10 mAb-GAA and 3E10 Fab-GAA Fusion Constructs We expressed representative chimeric polypeptides according to the protocol described in Hacker et al., 2013, Protein Expr Purif. 92: 67. Specifically, chimeric polypeptides comprising a GAA polypeptide portion and an internalizing moiety portion were made recombinantly. In this experiment, a GAA polypeptide comprising mature GAA (the GAA polypeptide portion of the chimeric polypeptide) was fused to either a full-length murine monoclonal 3E10 antibody comprising the light chain variable domain set forth in SEQ ID NO: 10 and the heavy chain variable domain set forth in SEQ ID NO: 9 (the internalizing moiety portion), or to a Fab of this 3E10 antibody (see FIG. 1). Specifically, in this example, the N-terminus of a GAA polypeptide comprising a mature GAA and having the amino acid sequence of SEQ ID NO: 22 was fused to the C-terminus of either the heavy chain constant region of a murine 3E10 Fab fragment or to the C-terminus of the heavy chain constant region of a full-length murine 3E10 monoclonal antibody (mAb). In this example, the heavy chain of the internalizing moiety comprises murine 3E10 antibody comprises the foregoing VH and a murine heavy chain constant domain comprising CH1, hinge, CH2, and CH3 regions, such as constant domain regions from an IgG1, IgG2a, IgG2b, or IgG4 antibody. In either case, a nucleotide sequence expressing the recombinant heavy chain and 3E10 light chain comprising the foregoing 3E10 VL were inserted into separate vectors and transiently transfected into CHO-DG44 cells in order to produce to produce the recombinant, chimeric protein. Similarly, the nucleotide sequence encoding the heavy and light chains could be expressed from a single vector. The chimeric constructs are shown schematically in FIG. 1.

In this example, a linker sequence was used to fuse the GAA polypeptide to the Fab or mAb heavy chains, and that linker had the amino acid sequence of SEQ ID NO: 30.

Exemplary Sequences

SEQ ID NO: 1=full-length, immature GAA amino acid sequence (952 amino acids; signal sequence indicated in bold/underline)

MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPVEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKVLDICVSLLMGEQFLVS

WC

SEQ ID NO: 2=full-length, immature GAA amino acid sequence (957 amino acids; signal sequence indicated in bold/underline)
(GenBank Accession No. EAW89583.1)

MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPIEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKARGPRVLDICVSLLMGE

QFLVSWC

SEQ ID NO: 3=exemplary mature GAA amino acid sequence (corresponding to residues 123-782 of SEQ ID NO: 1; one embodiment of a mature GAA polypeptide)

GQPWCFFPPSYPSYKLENLSSSEMGYTATLTRTTPTFFPKDILTLRLDV

MMETENRLHFTIKDPANRRYEVPLETPHVHSRAPSPLYSVEFSEEPFGV

IVRRQLDGRVLLNTTVAPLFFADQFLQLSTSLPSQYITGLAEHLSPLML

STSWTRITLWNRDLAPTPGANLYGSHPFYLALEDGGSAHGVFLLNSNAM

DVVLQPSPALSWRSTGGILDVYIFLGPEPKSVVQQYLDVVGYPFMPPYW

GLGFHLCRWGYSSTAITRQVVENMTRAHFPLDVQWNDLDYMDSRRDFTF

NKDGFRDFPAMVQELHQGGRRYMMIVDPAISSSGPAGSYRPYDEGLRRG

VFITNETGQPLIGKVWPGSTAFPDFTNPTALAWWEDMVAEFHDQVPFDG

MWIDMNEPSNFIRGSEDGCPNNELENPPYVPGVVGGTLQAATICASSHQ

FLSTHYNLHNLYGLTEAIASHRALVKARGTRPFVISRSTFAGHGRYAGH

WTGDVWSSWEQLASSVPEILQFNLLGVPLVGADVCGFLGNTSEELCVRW

TQLGAFYPFMRNHNSLLSLPQEPYSFSEPAQQAMRKALTLRYALLPHLY

TLFHQAHVAGETVARPLFLEFPKDSSTWTVDHQLLWGEALLITPVLQAG

KAEVTGYFPLGTWYDLQTVPVEA

SEQ ID NO: 4=exemplary mature GAA amino acid sequence (corresponding to residues 288-782 of SEQ ID NO: 1; one embodiment of a mature GAA polypeptide)

GANLYGSHPFYLALEDGGSAHGVFLLNSNAMDVVLQPSPALSWRSTGGI

LDVYIFLGPEPKSVVQQYLDVVGYPFMPPYWGLGFHLCRWGYSSTAITR

QVVENMTRAHFPLDVQWNDLDYMDSRRDFTFNKDGFRDFPAMVQELHQG

-continued

GRRYMMIVDPAISSSGPAGSYRPYDEGLRRGVFITNETGQPLIGKVWPG

STAFPDFTNPTALAWWEDMVAEFHDQVPFDGMWIDMNEPSNFIRGSEDG

CPNNELENPPYVPGVVGGTLQAATICASSHQFLSTHYNLHNLYGLTEAI

ASHRALVKARGTRPFVISRSTFAGHGRYAGHWTGDVWSSWEQLASSVPE

ILQFNLLGVPLVGADVCGFLGNTSEELCVRWTQLGAFYPFMRNHNSLLS

LPQEPYSFSEPAQQAMRKALTLRYALLPHLYTLFHQAHVAGETVARPLF

LEFPKDSSTWTVDHQLLWGEALLITPVLQAGKAEVTGYFPLGTWYDLQT

VPVEA

SEQ ID NO: 5=GS3 linker

GGGGSGGGGSGGGGS

SEQ ID NO: 6=Linker

GSTSGSGKSSEGKG

SEQ ID NO: 7=His tag

HHHHHH

SEQ ID NO: 8=c-Myc tag

EQKLISEEDL

SEQ ID NO: 9=exemplary 3E10 Variable Heavy Chain (V$_H$ having D31N substitution; see examples)

EVQLVESGGGLVKPGGSRKLSCAASGFTFSNYGMHWVRQAPEKGLEWVA

YISSGSSTIYYADTVKGRFTISRDNAKNTLFLQMTSLRSEDTAMYYCAR

RGLLLDYWGQGTTLTVSS

SEQ ID NO: 10=3E10 Variable Light Chain (V$_L$)

DIVLTQSPASLAVSLGQRATISCRASKSVSTSSYSYMHWYQQKPGQPPK

LLIKYASYLESGVPARFSGSGSGTDFHLNIHPVEEEDAATYYCQHSREF

PWTFGGGTKLELK

SEQ ID NO: 11=Exemplary chimeric polypeptide, Fv3E10-GAA (123-782)

DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELKGGGGSGGGGSGGGGSEVQLVESGGGLVKPGGSRKLSCAA

SGFTFSNYGMHWVRQAPEKGLEWVAYISSGSSTIYYADTVKGRFTISRDN

AKNTLFLQMTSLRSEDTAMYYCARRGLLLDYWGQGTTLTVSSEQKLSEED

LGSTSGSGKSSEGKGGGGPWCFFPPSYPSYKLENLSSSEMGYTATLTRTTP

TFFPKDILTLRLDVMMETENRLHFTIKDPANRRYEVPLETPRVHSRAPSP

LYSVEFSEEPFGVIVHRQLDGRVLLNTTVAPLFFADQFLQLSTSLPSQYI

TGLAEHLSPLMLSTSWTRITLWNRDLAPTPGANLYGSHPFYLALEDGGSA

HGVFLLNSNAMDVVLQPSPALSWRSTGGILDVYIFLGPEPKSVVQQYLDV

VGYPFMPPYWGLGFHLCRWGYSSTAITRQVVENMTRAHFPLDVQWNDLDY

MDSRRDFTFNKDGFRDFPAMVQELHQGGRRYMMIVDPAISSSGPAGSYRL

YDEGLRRGVFITNETGQPLIGKVWPGSTAFPDFTNPTALAWWEDMVAEFH

DQVPFDGMWIDMNEPSNFIRGSEDGCPNNELENPPYVPGVVGGTLQAATI

CASSHQFLSTHYNLHNLYGLTEAIASHRALVKARGTRPFVISRSTFAGHG

RYAGHWTGDVWSSWEQLASSVPEILQFNLLGVPLVGADVCGFLGNTSEEL

CVRWTQLGAFYPFMRNHNSLLSLPQEPYSFSEPAQQAMRKALTLRYALLP

HLYTLFHQAHVAGETVARPLFLEFPKDSSTWTVDHQLLWGEALLITPVLQ

AGKAEVTGYFPLGTWYDLQTVPIEAHHHHHH

SEQ ID NO:12=Exemplary chimeric polypeptide, Fv3E10-GAA (288-782)

DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELKGGGGSGGGGSGGGGSEVQLVESGGGLVKPGGSRKLSCAA

SGFTFSNYGMHWVRQAPEKGLEWVAYISSGSSTIYYADTVKGRFTISRDN

AKNTLFLQMTSLRSEDTAMYYCARRGLLLDYWGQGTTLTVSSEQKLSEED

LGSTSGSGKSSEGKGGGANLYGSHPFYLALEDGGSAHGVFLLNSNAMDVVL

QPSPALSWRSTGGILDVYIFLGPEPKSVVQQYLDVVGYPFMPPYWGLGFH

LCRWGYSSTAITRQVVENMTRAHFPLDVQWNDLDYMDSRRDFTFNKDGFR

DFPAMVQELHQGGRRYMMIVDPAISSSGPAGSYRLYDEGLRRGVFITNET

GQPLIGKVWPGSTAFPDFTNPTALAWWEDMVAEFHDQVPFDGMWIDMNEP

SNFIRGSEDGCPNNELENPPYVPGVVGGTLQAATICASSHQFLSTHYNLH

NLYGLTEAIASHRALVKARGTRPFVISRSTFAGHGRYAGHWTGDVWSSWE

QLASSVPEILQFNLLGVPLVGADVCGFLGNTSEELCVRWTQLGAFYPFMR

NHNSLLSLPQEPYSFSEPAQQAMRKALTLRYALLPHLYTLFHQAHVAGET

VARPLFLEFPKDSSTWTVDHQLLWGEALLITPVLQAGKAEVTGYFPLGTW

YDLQTVPIEAHHHHHH

SEQ ID NO: 13—heavy chain variable domain CDR1 of 3E10 VH (as that VH is defined with reference to SEQ ID NO: 9), in accordance with Kabat system

NYGMH

SEQ ID NO: 14—heavy chain variable domain CDR2 of 3E10 VH (as that VH is defined with reference to SEQ ID NO: 9), in accordance with Kabat system

YISSGSSTIYYADTVKG

SEQ ID NO: 15—heavy chain variable domain CDR3 of 3E10 VH (as that VH is defined with reference to SEQ ID NO: 9), in accordance with Kabat system

RGLLLDY

SEQ ID NO: 16—light chain variable domain CDR1 of 3E10 VL (as that VL is defined with reference to SEQ ID NO: 10), in accordance with Kabat system

RASKSVSTSSYSYMH

SEQ ID NO: 17—light chain variable domain CDR2 of 3E10 VL (as that VL is defined with reference to SEQ ID NO: 10), in accordance with Kabat system

YASYLES

SEQ ID NO: 18—light chain variable domain CDR3 of 3E10 VL (as that VL is defined with reference to SEQ ID NO: 10), in accordance with Kabat system

QHSREFPWT

SEQ ID NO: 19

AGIH

SEQ ID NO: 20

SAGIH

SEQ ID NO: 21—Exemplary GAA polypeptide comprising mature GAA (residues 61-952; one embodiment of a GAA polypeptide)

SRPGPRDAQAHPGRPRAVPTQCDVPPNSRFDCAPDKAITQEQCEARGCCY
IPAKQGLQGAQMGQPWCFFPPSYPSYKLENLSSSEMGYTATLTRTTPTFF
PKDILTLRLDVMMETENRLHFTIKDPANRRYEVPLETPHVHSRAPSPLYS
VEFSEEPFGVIVRRQLDGRVLLNTTVAPLFFADQFLQLSTSLPSQYITGL
AEHLSPLMLSTSWTRITLWNRDLAPTPGANLYGSHPFYLALEDGGSAHGV
FLLNSNAMDVVLQPSPALSWRSTGGILDVYIFLGPEPKSVVQQYLDVVGY
PFMPPYWGLGFHLCRWGYSSTAITRQVVENMTRAHFPLDVQWNDLDYMDS
RRDFTFNKDGFRDFPAMVQELHQGGRRYMMIVDPAISSSGPAGSYRPYDE
GLRRGVFITNETGQPLIGKVWPGSTAFPDFTNPTALAWWEDMVAEFHDQV
PFDGMWIDMNEPSNFIRGSEDGCPNNELENPPYVPGVVGGTLQAATICAS
SHQFLSTHYNLHNLYGLTEAIASHRALVKARGTRPFVISRSTFAGHRYA
GHWTGDVWSSWEQLASSVPEILQFNLLGVPLVGADVCGFLGNTSEELCVR
WTQLGAFYPFMRNHNSLLSLPQEPYSFSEPAQQAMRKALTLRYALLPHLY
TLFHQAHVAGETVARPLFLEFPKDSSTWTVDHQLLWGEALLITPVLQAGK
AEVTGYFPLGTWYDLQTVPVEALGSLPPPPAAPREPAIHSEGQWVTLPAP
LDTINVHLRAGYIIPLQGPGLTTTESRQQPMALAVALTKGGEARGELFWD
DGESLEVLERGAYTQVIFLARNNTIVNELVRVTSEGAGLQLQKVTVLGVA
TAPQQVLSNGVPVSNFTYSPDTKVLDICVSLLMGEQFLVSWC

SEQ ID NO: 22—Exemplary GAA polypeptide comprising mature GAA (residues 67-952; one embodiment of a GAA polypeptide)

DAQAHPGRPRAVPTQCDVPPNSRFDCAPDKAITQEQCEARGCCYIPAKQ
GLQGAQMGQPWCFFPPSYPSYKLENLSSSEMGYTATLTRTTPTFFPKDI
LTLRLDVMMETENRLHFTIKDPANRRYEVPLETPHVHSRAPSPLYSVEF
SEEPFGVIVRRQLDGRVLLNTTVAPLFFADQFLQLSTSLPSQYITGLAE
HLSPLMLSTSWTRITLWNRDLAPTPGANLYGSHPFYLALEDGGSAHGVF
LLNSNAMDVVLQPSPALSWRSTGGILDVYIFLGPEPKSVVQQYLDVVGY
PFMPPYWGLGFHLCRWGYSSTAITRQVVENMTRAHFPLDVQWNDLDYMD
SRRDFTFNKDGFRDFPAMVQELHQGGRRYMMIVDPAISSSGPAGSYRPY
DEGLRRGVFITNETGQPLIGKVWPGSTAFPDFTNPTALAWWEDMVAEFH
DQVPFDGMWIDMNEPSNFIRGSEDGCPNNELENPPYVPGVVGGTLQAAT
ICASSHQFLSTHYNLHNLYGLTEAIASHRALVKARGTRPFVISRSTFAG
HGRYAGHWTGDVWSSWEQLASSVPEILQFNLLGVPLVGADVCGFLGNTS
EELCVRWTQLGAFYPFMRNHNSLLSLPQEPYSFSEPAQQAMRKALTLRY
ALLPHLYTLFHQAHVAGETVARPLFLEFPKDSSTWTVDHQLLWGEALLI
TPVLQAGKAEVTGYFPLGTWYDLQTVPVEALGSLPPPPAAPREPAIHSE
GQWVTLPAPLDTINVHLRAGYIIPLQGPGLTTTESRQQPMALAVALTKG
GEARGELFWDDGESLEVLERGAYTQVIFLARNNTIVNELVRVTSEGAGL
QLQKVTVLGVATAPQQVLSNGVPVSNFTYSPDTKVLDICVSLLMGEQFL
VSWC

SEQ ID NO: 23—Exemplary GAA polypeptide comprising mature GAA (residues 70-952; one embodiment of a GAA polypeptide)

AHPGRPRAVPTQCDVPPNSRFDCAPDKAITQEQCEARGCCYIPAKQGLQA
QMGQPWCFFPPSYPSYKLENLSSSEMGYTATLTRTTPTFFPKDILTLRLDV
MMETENRLHFTIKDPANRRYEVPLETPHVHSRAPSPLYSVEFSEEPFGVIV
RRQLDGRVLLNTTVAPLFFADQFLQLSTSLPSQYITGLAEHLSPLMLSTSW
TRITLWNRDLAPTPGANLYGSHPFYLALEDGGSAHGVFLLNSNAMDVVLQP
SPALSWRSTGGILDVYIFLGPEPKSVVQQYLDVVGYPFMPPYWGLGFHLCR
WGYSSTAITRQVVENMTRAHFPLDVQWNDLDYMDSRRDFTFNKDGFRDFPA
MVQELHQGGRRYMMIVDPAISSSGPAGSYRPYDEGLRRGVFITNETGQPLI
GKVWPGSTAFPDFTNPTALAWWEDMVAEFHDQVPFDGMWIDMNEPSNFIRG
SEDGCPNNELENPPYVPGVVGGTLQAATICASSHQFLSTHYNLHNLYGLTE
AIASHRALVKARGTRPFVISRSTFAGHGRYAGHWTGDVWSSWEQLASSVPE
ILQFNLLGVPLVGADVCGFLGNTSEELCVRWTQLGAFYPFMRNHNSLLSLP
QEPYSFSEPAQQAMRKALTLRYALLPHLYTLFHQAHVAGETVARPLFLEFP
KDSSTWTVDHQLLWGEALLITPVLQAGKAEVTGYFPLGTWYDLQTVPVEAL

-continued

GSLPPPPAAPREPAIHSEGQWVTLPAPLDTINVHLRAGYIIPLQGPGLTTT

ESRQQPMALAVALTKGGEARGELFWDDGESLEVLERGAYTQVIFLARNNTI

VNELVRVTSEGAGLQLQKVTVLGVATAPQQVLSNGVPVSNFTYSPDTKVLD

ICVSLLMGEQFLVSWC

SEQ ID NO: 24—heavy chain variable (VH) domain CDR1 of exemplary 3E10 $V_H$ (as that VH is defined with reference to SEQ ID NO: 9), in accordance with the IMGT system

GFTFSNYG

SEQ ID NO: 25—heavy chain variable (VH) domain CDR2 of exemplary 3E10 $V_H$ (as that VH is defined with reference to SEQ ID NO: 9), in accordance with the IMGT system

ISSGSSTI

SEQ ID NO: 26—heavy chain variable (VH) domain CDR3 of exemplary 3E10 $V_H$ (as that VH is defined with reference to SEQ ID NO: 9), in accordance with the IMGT system

ARRGLLLDY

SEQ ID NO: 27—light chain variable (VL) domain CDR1 of exemplary 3E10 $V_L$ (as that VL is defined with reference to SEQ ID NO: 10), in accordance with the IMGT system

KSVSTSSYSY

SEQ ID NO: 28—light chain variable (VL) domain CDR2 of exemplary 3E10 $V_L$ (as that VL is defined with reference to SEQ ID NO: 10), in accordance with the IMGT system

YAS

SEQ ID NO: 29—light chain variable (VL) domain CDR3 of exemplary 3E10 $V_L$ (as that VL is defined with reference to SEQ ID NO: 10), in accordance with the IMGT system

QHSREFPWT

SEQ ID NO: 30—linker sequence

GGSGGGSGGGSGG

SEQ ID NO: 31—full linker region (residues 57-78 of GAA)

HILLHDFLLVPRELSGSSPVLEETHPAH

SEQ ID NO: 32—bovine GAA precursor protein (GenBank Accession No. NP_776338.1)

MMRWPPCSRPLLGVCTLLSLALLGHILLHDLEVVPRELRGFSQDEIHQAC

QPGASSPECRGSPRAAPTQCDLPPNSRFDCAPDKGITPQQCEARGCCYMP

AEWPPDAQMGQPWCFFPPSYPSYRLENLTTTETGYTATLTRAVPTFFPKD

IMTLRLDMLMETESRLHFTIKDPANRRYEVPLETPRVYSQAPFTLYSVEF

SEEPFGVVVRRKLDGRVLLNTTVAPLFFADQFLQLSTSLPSQHITGLAEH

LGSLMLSTNWTKITLWNRDIAPEPNVNLYGSHPFYLVLEDGGLAHGVFLL

NSNAMDVVLQPSPALSWRSTGGILDVYIFLGPEPKSVVQQYLDVVGYPFM

PPYWGLGFHLCRWGYSTSAITRQVVENMTRAYFPLDVQWNDLDYMDARRD

FTFNKDHFGDFPAMVQELHQGGRRYIMIVDPAISSSGPAGTYRPYDEGLR

RGVFITNETGQPLIGQVWPGLTAFPDFTNPETLDWWQDMVTEFHAQVPFD

GMWIDMNEPSNFVRGSVDGCPDNSLENPPYLPGVVGGTLRAATICASSHQ

FLSTHYDLHNLYGLTEALASHRALVKARGMRPFVISRSTFAGHGRYSGHW

TGDVWSNWEQLSYSVPEILLFNLLGVPLVGADICGFLGNTSEELCVRWTQ

LGAFYPFMRNHNALNSQPQEPYRFSETAQQAMRKAFTLRYVLLPYLYTLF

HRAHVRGETVARPLFLEFPEDPSTWTVDRQLLWGEALLITPVLEAEKVEV

TGYFPQGTWYDLQTVPMEAFGSLPPPAPLTSVIHSKGQWVTLSAPLDTIN

VHLRAGHIIPMQGPALTTTESRKQHMALAVALTASGEAQGELFWDDGESL

GVLDGGDYTQLIFLAKNNTFVNKLVHVSSEGASLQLRNVTVLGVATAPQQ

VLCNSVPVSNFTFSPDTETLAIPVSLTMGEQFVISWS

SEQ ID NO: 33—KFERQ

KFERQ

SEQ ID NO: 34—$(G_4S)_n$—, wherein n is an integer from 1-10

$(GGGGS)_n$

SEQ ID NO: 35—ASSLNIA homing peptide

ASSLNIA

SEQ ID NO: 36—Arg7 Peptide

RRRRRRR

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A chimeric polypeptide comprising: (i) a GAA polypeptide comprising the amino acid sequence set forth in SEQ ID NO: 21 or SEQ ID NO: 22 and (ii) an internalizing moiety that binds DNA with a $K_D$ of less than 100 nM and/or promotes transit across cellular membranes via an equilibrative nucleoside transporter 2 (ENT2) transporter;
   wherein the internalizing moiety is an antibody or an antigen binding fragment comprising:
   a) a monoclonal antibody 3E10, or a variant thereof that retains cell penetrating activity, or a variant thereof that binds the same epitope as 3E10, or an antigen binding fragment of any of the foregoing; or
   b) a VH CDR1 having the amino acid sequence of SEQ ID NO: 24; a VH CDR2 having the amino acid sequence of SEQ ID NO: 25; a VH CDR3 having the amino acid sequence of SEQ ID NO: 26; a VL CDR1 having the amino acid sequence of SEQ ID NO: 27; a VL CDR2 having the amino acid sequence of SEQ ID NO: 28; and a VL CDR3 having the amino acid sequence of SEQ ID NO: 29; which CDRs are according to the IMGT system; or
   c) at least one of a heavy chain variable domain comprising the amino acid sequence of SEQ ID NO: 9, or a humanized variant thereof and a light chain variable domain comprising the amino acid sequence of SEQ ID NO: 10, or a humanized variant thereof; and
   wherein the chimeric polypeptide does not comprise the full length, GAA precursor polypeptide set forth in SEQ ID NO: 1, wherein the chimeric polypeptide does not comprise the portion of GAA polypeptide set forth in residues 1-57 of SEQ ID NO: 1 or 2.

2. The chimeric polypeptide of claim 1, wherein the chimeric polypeptide has acid alpha-glucosidase activity.

3. The chimeric polypeptide of claim 1, wherein the chimeric polypeptide lacks at least a portion of the GAA full linker region, wherein the full linker region corresponds to the amino acids 57-78 of SEQ ID NOs: 1 or 2.

4. The chimeric polypeptide of claim 1, wherein neither the GAA polypeptide nor the chimeric polypeptide comprise a contiguous amino acid sequence corresponding to the amino acids 1-60 of SEQ ID NO: 1 or 2.

5. The chimeric polypeptide of claim 4, wherein the chimeric polypeptide or GAA polypeptide comprises the amino acid sequence of SEQ ID NO: 21.

6. The chimeric polypeptide of claim 1, wherein neither the GAA polypeptide nor the chimeric polypeptide comprise a contiguous amino acid sequence corresponding to the amino acids 1-66 of SEQ ID NO: 1 or 2.

7. The chimeric polypeptide of claim 6, wherein the chimeric polypeptide or GAA polypeptide comprises the amino acid sequence of SEQ ID NO: 22.

8. The chimeric polypeptide of claim 1, wherein the mature GAA polypeptide has a glycosylation pattern that differs from that of naturally occurring human GAA.

9. The chimeric polypeptide of claim 1, wherein the internalizing moiety promotes delivery of the chimeric polypeptide into cytoplasm of cells.

10. The chimeric polypeptide of claim 1, wherein the chimeric polypeptide is capable of being taken up by an autophagic vacuole.

11. The chimeric polypeptide of claim 1, wherein the internalizing moiety promotes transport of said chimeric polypeptide into muscle cells or hepatocytes.

12. The chimeric polypeptide of claim 1, wherein the chimeric polypeptide further comprises one or more polypeptide portions that enhance one or more of in vivo stability, in vivo half life, uptake/administration, production, or purification.

13. The chimeric polypeptide of claim 1, wherein the internalizing moiety comprises an antibody or antigen binding fragment that can transit a cellular membrane via an equilibrative nucleoside transporter 2 (ENT2) transporter and/or binds DNA with a $K_D$ of less than 100 nM.

14. The chimeric polypeptide of claim 13, wherein said antibody or antigen binding fragment is:
   a) a monoclonal antibody 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing; or
   b) a monoclonal antibody 3E10, or a variant thereof that retains the cell penetrating activity of 3E10, or an antigen binding fragment of 3E10 or said 3E10 variant.

15. The chimeric polypeptide of claim 14, wherein the antibody or antigen binding fragment is a chimeric, humanized, or fully human antibody or antigen binding fragment.

16. The chimeric polypeptide of claim 13, wherein the antibody or antigen binding fragment comprises a heavy chain variable domain comprising an amino acid sequence at least 95% identical to SEQ ID NO: 9, or a humanized variant thereof.

17. The chimeric polypeptide of claim 13, wherein the antibody or antigen binding fragment comprises a light chain variable domain comprising an amino acid sequence at least 95% identical to SEQ ID NO: 10, or a humanized variant thereof.

18. The chimeric polypeptide of claim 13, wherein the antibody or antigen binding fragment comprises a heavy chain variable domain comprising the amino acid sequence of SEQ ID NO: 9, or a humanized variant thereof, and a light chain variable domain comprising the amino acid sequence of SEQ ID NO: 10, or a humanized variant thereof.

19. The chimeric polypeptide of claim 13, wherein the antibody or antigen binding fragment comprises
   a VH CDR1 having the amino acid sequence of SEQ ID NO 24;
   a VH CDR2 having the amino acid sequence of SEQ ID NO: 25;
   a VH CDR3 having the amino acid sequence of SEQ ID NO: 26;
   a VL CDR1 having the amino acid sequence of SEQ ID NO: 27;
   a VL CDR2 having the amino acid sequence of SEQ ID NO: 28; and
   a VL CDR3 having the amino acid sequence of SEQ ID NO: 29;
which CDRs are according to the IMGT system.

20. The chimeric polypeptide of claim 13, wherein the antibody or antigen binding fragment is an Fab.

21. The chimeric polypeptide of claim 13, wherein the internalizing moiety is an antibody.

22. The chimeric polypeptide of claim 20, wherein the N-terminus of the GAA polypeptide is fused to the C-terminus of the heavy chain of the Fab.

23. The chimeric polypeptide of claim 11, wherein the N-terminus of the GAA polypeptide is fused to the C-terminus of the heavy chain of the Fab by means of a linker.

24. A nucleic acid construct, comprising a nucleotide sequence that encodes the chimeric polypeptide of claim 18.

25. A nucleic acid construct, comprising a nucleotide sequence that encodes a GAA polypeptide, operably linked to a nucleotide sequence that encodes an internalizing moiety, wherein the nucleic acid construct encodes a chimeric polypeptide comprising: (i) the amino acid sequence set forth in SEQ ID NO: 21 or SEQ ID NO: 22 and (ii) an internalizing moiety that promotes transit across cellular membranes via an equilibrative nucleoside transporter 2 (ENT2) transporter and/or that binds DNA with a $K_D$ of less than 100 nM;
   wherein the internalizing moiety is an antibody or an antigen binding fragment comprising:
   a) a monoclonal antibody 3E10, or a variant thereof that retains cell penetrating activity, or a variant thereof that binds the same epitope as 3E10, or an antigen binding fragment of any of the foregoing; or
   b) a VH CDR1 having the amino acid sequence of SEQ ID NO: 24; a VH CDR2 having the amino acid sequence of SEQ ID NO: 25; a VH CDR3 having the amino acid sequence of SEQ ID NO: 26; a VL CDR1 having the amino acid sequence of SEQ ID NO: 27; a VL CDR2 having the amino acid sequence of SEQ ID NO: 28; and a VL CDR3 having the amino acid sequence of SEQ ID NO: 29; which CDRs are according to the IMGT system; or
   c) at least one of a heavy chain variable domain comprising the amino acid sequence of SEQ ID NO: 9, or a humanized variant thereof and a light chain variable domain comprising the amino acid sequence of SEQ ID NO: 10, or a humanized variant thereof; and
   wherein the chimeric polypeptide does not comprise the full length, GAA polypeptide set forth in SEQ ID NO: 1, wherein the chimeric polypeptide does not comprise the portion of GAA polypeptide set forth in residues 1-57 of SEQ ID NO: 1 or 2.

26. A vector comprising the nucleic acid construct of claim 24.

27. A host cell comprising the vector of claim 26.

28. A method of producing a chimeric polypeptide comprising culturing the host cell of claim 27 under appropriate conditions to allow expression of the polypeptide to occur.

29. A composition comprising the chimeric polypeptide of claim 1, and a pharmaceutically acceptable carrier.

30. A method of treating Pompe disease in a subject in need thereof, comprising administering to the subject an effective amount of the chimeric polypeptide of claim 1.

31. The method of claim 30, wherein said subject in need thereof is a subject:
   a) whose disease has been refractory to one or more previous enzyme replacement therapies;
   b) having pathologic cytoplasmic glycogen accumulation prior to initiation of treatment with said chimeric polypeptide;
   c) diagnosed with Pompe disease greater than six months prior to initiation of treatment with said chimeric polypeptide;

d) diagnosed with Pompe disease at least one year prior to initiation of treatment with said chimeric polypeptide;
e) in whom the onset of symptoms of Pompe disease occurred greater than six months prior to initiation of treatment with said chimeric polypeptide; and/or
f) in whom the onset of symptoms of Pompe disease occurred at least one year prior to initiation of treatment with said chimeric polypeptide.

32. A method of decreasing glycogen accumulation in cytoplasm, lysosomes, and/or autophagic vacuoles of muscle cells, comprising contacting muscle cells with a chimeric polypeptide, which chimeric polypeptide comprising: (i) the amino acid sequence set forth in SEQ ID NO: 21 or SEQ ID NO: 22 and (ii) an internalizing moiety that promotes transit across cellular membranes via an equilibrative nucleoside transporter 2 (ENT2) transporter; wherein the internalizing moiety is an antibody or an antigen binding fragment comprising:

a) a monoclonal antibody 3E10, or a variant thereof that retains cell penetrating activity, or a variant thereof that binds the same epitope as 3E10, or an antigen binding fragment of any of the foregoing; or b) a VH CDR1 having the amino acid sequence of SEQ ID NO: 24; a VH CDR2 having the amino acid sequence of SEQ ID NO: 25; a VH CDR3 having the amino acid sequence of SEQ ID NO: 26; a VL CDR1 having the amino acid sequence of SEQ ID NO: 27; a VL CDR2 having the amino acid sequence of SEQ ID NO: 28; and a VL CDR3 having the amino acid sequence of SEQ ID NO: 29; which CDRs are according to the IMGT stem; or c) at least one of a heavy chain variable domain comprising the amino acid sequence of SEQ ID NO: 9, or a humanized variant thereof and a light chain variable domain comprising the amino acid sequence of SEQ ID NO: 10, or a humanized variant thereof; and wherein the chimeric polypeptide does not comprise the full length, GAA precursor polypeptide set forth in SEQ ID NO: 1, wherein the chimeric polypeptide does not comprise the portion of GAA polypeptide set forth in residues 1-57 of SEQ ID NO: 1 or 2.

* * * * *

SEQUENCE LISTING

<160> NUMBER OF SEQ ID NOS: 36

<210> SEQ ID NO 1
<211> LENGTH: 952
<212> TYPE: PRT
<213> ORGANISM: Homo sapiens

<400> SEQUENCE: 1

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365
```

-continued

| | | | | | | | | | | | | |
|---|---|---|---|---|---|---|---|---|---|---|---|---|
| Leu | Gly | Phe | His | Leu | Cys | Arg | Trp | Gly | Tyr | Ser | Ser | Thr | Ala | Ile | Thr |
| 370 | | | | | 375 | | | | | 380 | | | | | |
| Arg | Gln | Val | Val | Glu | Asn | Met | Thr | Arg | Ala | His | Phe | Pro | Leu | Asp | Val |
| 385 | | | | | 390 | | | | | 395 | | | | | 400 |
| Gln | Trp | Asn | Asp | Leu | Asp | Tyr | Met | Asp | Ser | Arg | Arg | Asp | Phe | Thr | Phe |
| | | | | 405 | | | | | 410 | | | | | 415 | |
| Asn | Lys | Asp | Gly | Phe | Arg | Asp | Phe | Pro | Ala | Met | Val | Gln | Glu | Leu | His |
| | | | 420 | | | | | 425 | | | | | 430 | | |
| Gln | Gly | Gly | Arg | Arg | Tyr | Met | Met | Ile | Val | Asp | Pro | Ala | Ile | Ser | Ser |
| | | 435 | | | | | 440 | | | | | 445 | | | |
| Ser | Gly | Pro | Ala | Gly | Ser | Tyr | Arg | Pro | Tyr | Asp | Glu | Gly | Leu | Arg | Arg |
| 450 | | | | | 455 | | | | | 460 | | | | | |
| Gly | Val | Phe | Ile | Thr | Asn | Glu | Thr | Gly | Gln | Pro | Leu | Ile | Gly | Lys | Val |
| 465 | | | | | 470 | | | | | 475 | | | | | 480 |
| Trp | Pro | Gly | Ser | Thr | Ala | Phe | Pro | Asp | Phe | Thr | Asn | Pro | Thr | Ala | Leu |
| | | | | 485 | | | | | 490 | | | | | 495 | |
| Ala | Trp | Trp | Glu | Asp | Met | Val | Ala | Glu | Phe | His | Asp | Gln | Val | Pro | Phe |
| | | | | 500 | | | | | 505 | | | | | 510 | |
| Asp | Gly | Met | Trp | Ile | Asp | Met | Asn | Glu | Pro | Ser | Asn | Phe | Ile | Arg | Gly |
| | | | 515 | | | | | 520 | | | | | 525 | | |
| Ser | Glu | Asp | Gly | Cys | Pro | Asn | Asn | Glu | Leu | Glu | Asn | Pro | Pro | Tyr | Val |
| | 530 | | | | | 535 | | | | | 540 | | | | |
| Pro | Gly | Val | Val | Gly | Gly | Thr | Leu | Gln | Ala | Ala | Thr | Ile | Cys | Ala | Ser |
| 545 | | | | | 550 | | | | | 555 | | | | | 560 |
| Ser | His | Gln | Phe | Leu | Ser | Thr | His | Tyr | Asn | Leu | His | Asn | Leu | Tyr | Gly |
| | | | | 565 | | | | | 570 | | | | | 575 | |
| Leu | Thr | Glu | Ala | Ile | Ala | Ser | His | Arg | Ala | Leu | Val | Lys | Ala | Arg | Gly |
| | | | | 580 | | | | | 585 | | | | | 590 | |
| Thr | Arg | Pro | Phe | Val | Ile | Ser | Arg | Ser | Thr | Phe | Ala | Gly | His | Gly | Arg |
| | | | 595 | | | | | 600 | | | | | 605 | | |
| Tyr | Ala | Gly | His | Trp | Thr | Gly | Asp | Val | Trp | Ser | Ser | Trp | Glu | Gln | Leu |
| | 610 | | | | | 615 | | | | | 620 | | | | |
| Ala | Ser | Ser | Val | Pro | Glu | Ile | Leu | Gln | Phe | Asn | Leu | Leu | Gly | Val | Pro |
| 625 | | | | | 630 | | | | | 635 | | | | | 640 |
| Leu | Val | Gly | Ala | Asp | Val | Cys | Gly | Phe | Leu | Gly | Asn | Thr | Ser | Glu | Glu |
| | | | | 645 | | | | | 650 | | | | | 655 | |
| Leu | Cys | Val | Arg | Trp | Thr | Gln | Leu | Gly | Ala | Phe | Tyr | Pro | Phe | Met | Arg |
| | | | 660 | | | | | 665 | | | | | 670 | | |
| Asn | His | Asn | Ser | Leu | Leu | Ser | Leu | Pro | Gln | Glu | Pro | Tyr | Ser | Phe | Ser |
| | | | 675 | | | | | 680 | | | | | 685 | | |
| Glu | Pro | Ala | Gln | Gln | Ala | Met | Arg | Lys | Ala | Leu | Thr | Leu | Arg | Tyr | Ala |
| | 690 | | | | | 695 | | | | | 700 | | | | |
| Leu | Leu | Pro | His | Leu | Tyr | Thr | Leu | Phe | His | Gln | Ala | His | Val | Ala | Gly |
| 705 | | | | | 710 | | | | | 715 | | | | | 720 |
| Glu | Thr | Val | Ala | Arg | Pro | Leu | Phe | Leu | Glu | Phe | Pro | Lys | Asp | Ser | Ser |
| | | | | 725 | | | | | 730 | | | | | 735 | |
| Thr | Trp | Thr | Val | Asp | His | Gln | Leu | Leu | Trp | Gly | Glu | Ala | Leu | Leu | Ile |
| | | | 740 | | | | | 745 | | | | | 750 | | |
| Thr | Pro | Val | Leu | Gln | Ala | Gly | Lys | Ala | Glu | Val | Thr | Gly | Tyr | Phe | Pro |
| | | 755 | | | | | 760 | | | | | 765 | | | |
| Leu | Gly | Thr | Trp | Tyr | Asp | Leu | Gln | Thr | Val | Pro | Val | Glu | Ala | Leu | Gly |
| 770 | | | | | 775 | | | | | 780 | | | | | |
| Ser | Leu | Pro | Pro | Pro | Pro | Ala | Ala | Pro | Arg | Glu | Pro | Ala | Ile | His | Ser |

```
            785                 790                 795                 800
        Glu Gly Gln Trp Val Thr Leu Pro Ala Pro Leu Asp Thr Ile Asn Val
                        805                 810                 815

His Leu Arg Ala Gly Tyr Ile Ile Pro Leu Gln Gly Pro Gly Leu Thr
                        820                 825                 830

Thr Thr Glu Ser Arg Gln Pro Met Ala Leu Ala Val Ala Leu Thr
                        835                 840                 845

Lys Gly Gly Glu Ala Arg Gly Glu Leu Phe Trp Asp Asp Gly Glu Ser
                        850                 855                 860

Leu Glu Val Leu Glu Arg Gly Ala Tyr Thr Gln Val Ile Phe Leu Ala
        865                 870                 875                 880

Arg Asn Asn Thr Ile Val Asn Glu Leu Val Arg Val Thr Ser Glu Gly
                        885                 890                 895

Ala Gly Leu Gln Leu Gln Lys Val Thr Val Leu Gly Val Ala Thr Ala
                        900                 905                 910

Pro Gln Gln Val Leu Ser Asn Gly Val Pro Val Ser Asn Phe Thr Tyr
                        915                 920                 925

Ser Pro Asp Thr Lys Val Leu Asp Ile Cys Val Ser Leu Leu Met Gly
                        930                 935                 940

Glu Gln Phe Leu Val Ser Trp Cys
        945                 950

<210> SEQ ID NO 2
<211> LENGTH: 957
<212> TYPE: PRT
<213> ORGANISM: Homo sapiens

<400> SEQUENCE: 2

Met Gly Val Arg His Pro Pro Cys Ser His Arg Leu Leu Ala Val Cys
        1               5                   10                  15

Ala Leu Val Ser Leu Ala Thr Ala Ala Leu Leu Gly His Ile Leu Leu
                        20                  25                  30

His Asp Phe Leu Leu Val Pro Arg Glu Leu Ser Gly Ser Ser Pro Val
                        35                  40                  45

Leu Glu Glu Thr His Pro Ala His Gln Gln Gly Ala Ser Arg Pro Gly
                        50                  55                  60

Pro Arg Asp Ala Gln Ala His Pro Gly Arg Pro Arg Ala Val Pro Thr
        65                  70                  75                  80

Gln Cys Asp Val Pro Pro Asn Ser Arg Phe Asp Cys Ala Pro Asp Lys
                        85                  90                  95

Ala Ile Thr Gln Glu Gln Cys Glu Ala Arg Gly Cys Cys Tyr Ile Pro
                        100                 105                 110

Ala Lys Gln Gly Leu Gln Gly Ala Gln Met Gly Gln Pro Trp Cys Phe
                        115                 120                 125

Phe Pro Pro Ser Tyr Pro Ser Tyr Lys Leu Glu Asn Leu Ser Ser Ser
                        130                 135                 140

Glu Met Gly Tyr Thr Ala Thr Leu Thr Arg Thr Thr Pro Thr Phe Phe
        145                 150                 155                 160

Pro Lys Asp Ile Leu Thr Leu Arg Leu Asp Val Met Met Glu Thr Glu
                        165                 170                 175

Asn Arg Leu His Phe Thr Ile Lys Asp Pro Ala Asn Arg Arg Tyr Glu
                        180                 185                 190

Val Pro Leu Glu Thr Pro His Val His Ser Arg Ala Pro Ser Pro Leu
                        195                 200                 205
```

```
Tyr Ser Val Glu Phe Ser Glu Glu Pro Phe Gly Val Ile Val Arg Arg
    210             215             220

Gln Leu Asp Gly Arg Val Leu Leu Asn Thr Thr Val Ala Pro Leu Phe
225             230             235             240

Phe Ala Asp Gln Phe Leu Gln Leu Ser Thr Ser Leu Pro Ser Gln Tyr
            245             250             255

Ile Thr Gly Leu Ala Glu His Leu Ser Pro Leu Met Leu Ser Thr Ser
            260             265             270

Trp Thr Arg Ile Thr Leu Trp Asn Arg Asp Leu Ala Pro Thr Pro Gly
        275             280             285

Ala Asn Leu Tyr Gly Ser His Pro Phe Tyr Leu Ala Leu Glu Asp Gly
    290             295             300

Gly Ser Ala His Gly Val Phe Leu Leu Asn Ser Asn Ala Met Asp Val
305             310             315             320

Val Leu Gln Pro Ser Pro Ala Leu Ser Trp Arg Ser Thr Gly Gly Ile
            325             330             335

Leu Asp Val Tyr Ile Phe Leu Gly Pro Glu Pro Lys Ser Val Val Gln
            340             345             350

Gln Tyr Leu Asp Val Val Gly Tyr Pro Phe Met Pro Pro Tyr Trp Gly
    355             360             365

Leu Gly Phe His Leu Cys Arg Trp Gly Tyr Ser Ser Thr Ala Ile Thr
370             375             380

Arg Gln Val Val Glu Asn Met Thr Arg Ala His Phe Pro Leu Asp Val
385             390             395             400

Gln Trp Asn Asp Leu Asp Tyr Met Asp Ser Arg Arg Asp Phe Thr Phe
            405             410             415

Asn Lys Asp Gly Phe Arg Asp Phe Pro Ala Met Val Gln Glu Leu His
            420             425             430

Gln Gly Gly Arg Arg Tyr Met Met Ile Val Asp Pro Ala Ile Ser Ser
            435             440             445

Ser Gly Pro Ala Gly Ser Tyr Arg Pro Tyr Asp Glu Gly Leu Arg Arg
    450             455             460

Gly Val Phe Ile Thr Asn Glu Thr Gly Gln Pro Leu Ile Gly Lys Val
465             470             475             480

Trp Pro Gly Ser Thr Ala Phe Pro Asp Phe Thr Asn Pro Thr Ala Leu
            485             490             495

Ala Trp Trp Glu Asp Met Val Ala Glu Phe His Asp Gln Val Pro Phe
            500             505             510

Asp Gly Met Trp Ile Asp Met Asn Glu Pro Ser Asn Phe Ile Arg Gly
        515             520             525

Ser Glu Asp Gly Cys Pro Asn Asn Glu Leu Glu Asn Pro Pro Tyr Val
    530             535             540

Pro Gly Val Val Gly Gly Thr Leu Gln Ala Ala Thr Ile Cys Ala Ser
545             550             555             560

Ser His Gln Phe Leu Ser Thr His Tyr Asn Leu His Asn Leu Tyr Gly
            565             570             575

Leu Thr Glu Ala Ile Ala Ser His Arg Ala Leu Val Lys Ala Arg Gly
            580             585             590

Thr Arg Pro Phe Val Ile Ser Arg Ser Thr Phe Ala Gly His Gly Arg
            595             600             605

Tyr Ala Gly His Trp Thr Gly Asp Val Trp Ser Ser Trp Glu Gln Leu
    610             615             620

Ala Ser Ser Val Pro Glu Ile Leu Gln Phe Asn Leu Leu Gly Val Pro
```

```
            625                 630                 635                 640
        Leu Val Gly Ala Asp Val Cys Gly Phe Leu Gly Asn Thr Ser Glu Glu
                            645                 650                 655
        Leu Cys Val Arg Trp Thr Gln Leu Gly Ala Phe Tyr Pro Phe Met Arg
                            660                 665                 670
        Asn His Asn Ser Leu Leu Ser Leu Pro Gln Glu Pro Tyr Ser Phe Ser
                            675                 680                 685
        Glu Pro Ala Gln Gln Ala Met Arg Lys Ala Leu Thr Leu Arg Tyr Ala
                            690                 695                 700
        Leu Leu Pro His Leu Tyr Thr Leu Phe His Gln Ala His Val Ala Gly
        705                 710                 715                 720
        Glu Thr Val Ala Arg Pro Leu Phe Leu Glu Phe Pro Lys Asp Ser Ser
                            725                 730                 735
        Thr Trp Thr Val Asp His Gln Leu Leu Trp Gly Glu Ala Leu Leu Ile
                            740                 745                 750
        Thr Pro Val Leu Gln Ala Gly Lys Ala Glu Val Thr Gly Tyr Phe Pro
                            755                 760                 765
        Leu Gly Thr Trp Tyr Asp Leu Gln Thr Val Pro Ile Glu Ala Leu Gly
                            770                 775                 780
        Ser Leu Pro Pro Pro Ala Ala Pro Arg Glu Pro Ala Ile His Ser
        785                 790                 795                 800
        Glu Gly Gln Trp Val Thr Leu Pro Ala Pro Leu Asp Thr Ile Asn Val
                            805                 810                 815
        His Leu Arg Ala Gly Tyr Ile Ile Pro Leu Gln Gly Pro Gly Leu Thr
                            820                 825                 830
        Thr Thr Glu Ser Arg Gln Gln Pro Met Ala Leu Ala Val Ala Leu Thr
                            835                 840                 845
        Lys Gly Gly Glu Ala Arg Gly Glu Leu Phe Trp Asp Asp Gly Glu Ser
                            850                 855                 860
        Leu Glu Val Leu Glu Arg Gly Ala Tyr Thr Gln Val Ile Phe Leu Ala
        865                 870                 875                 880
        Arg Asn Asn Thr Ile Val Asn Glu Leu Val Arg Val Thr Ser Glu Gly
                            885                 890                 895
        Ala Gly Leu Gln Leu Gln Lys Val Thr Val Leu Gly Val Ala Thr Ala
                            900                 905                 910
        Pro Gln Gln Val Leu Ser Asn Gly Val Pro Val Ser Asn Phe Thr Tyr
                            915                 920                 925
        Ser Pro Asp Thr Lys Ala Arg Gly Pro Arg Val Leu Asp Ile Cys Val
                            930                 935                 940
        Ser Leu Leu Met Gly Glu Gln Phe Leu Val Ser Trp Cys
        945                 950                 955

<210> SEQ ID NO 3
<211> LENGTH: 660
<212> TYPE: PRT
<213> ORGANISM: Homo sapiens

<400> SEQUENCE: 3

Gly Gln Pro Trp Cys Phe Phe Pro Pro Ser Tyr Pro Ser Tyr Lys Leu
        1                   5                   10                  15
        Glu Asn Leu Ser Ser Ser Glu Met Gly Tyr Thr Ala Thr Leu Thr Arg
                            20                  25                  30
        Thr Thr Pro Thr Phe Phe Pro Lys Asp Ile Leu Thr Leu Arg Leu Asp
                            35                  40                  45
```

Val Met Met Glu Thr Glu Asn Arg Leu His Phe Thr Ile Lys Asp Pro
50                      55                      60

Ala Asn Arg Arg Tyr Glu Val Pro Leu Glu Thr Pro His Val His Ser
65                  70                  75                  80

Arg Ala Pro Ser Pro Leu Tyr Ser Val Glu Phe Ser Glu Pro Phe
            85                  90                  95

Gly Val Ile Val Arg Arg Gln Leu Asp Gly Arg Val Leu Leu Asn Thr
                100                 105                 110

Thr Val Ala Pro Leu Phe Phe Ala Asp Gln Phe Leu Gln Leu Ser Thr
            115                 120                 125

Ser Leu Pro Ser Gln Tyr Ile Thr Gly Leu Ala Glu His Leu Ser Pro
130                 135                 140

Leu Met Leu Ser Thr Ser Trp Thr Arg Ile Thr Leu Trp Asn Arg Asp
145                 150                 155                 160

Leu Ala Pro Thr Pro Gly Ala Asn Leu Tyr Gly Ser His Pro Phe Tyr
                165                 170                 175

Leu Ala Leu Glu Asp Gly Gly Ser Ala His Gly Val Phe Leu Leu Asn
            180                 185                 190

Ser Asn Ala Met Asp Val Val Leu Gln Pro Ser Pro Ala Leu Ser Trp
        195                 200                 205

Arg Ser Thr Gly Gly Ile Leu Asp Val Tyr Ile Phe Leu Gly Pro Glu
210                 215                 220

Pro Lys Ser Val Val Gln Gln Tyr Leu Asp Val Val Gly Tyr Pro Phe
225                 230                 235                 240

Met Pro Pro Tyr Trp Gly Leu Gly Phe His Leu Cys Arg Trp Gly Tyr
            245                 250                 255

Ser Ser Thr Ala Ile Thr Arg Gln Val Val Glu Asn Met Thr Arg Ala
        260                 265                 270

His Phe Pro Leu Asp Val Gln Trp Asn Asp Leu Asp Tyr Met Asp Ser
    275                 280                 285

Arg Arg Asp Phe Thr Phe Asn Lys Asp Gly Phe Arg Asp Phe Pro Ala
290                 295                 300

Met Val Gln Glu Leu His Gln Gly Gly Arg Arg Tyr Met Met Ile Val
305                 310                 315                 320

Asp Pro Ala Ile Ser Ser Ser Gly Pro Ala Gly Ser Tyr Arg Pro Tyr
            325                 330                 335

Asp Glu Gly Leu Arg Arg Gly Val Phe Ile Thr Asn Glu Thr Gly Gln
            340                 345                 350

Pro Leu Ile Gly Lys Val Trp Pro Gly Ser Thr Ala Phe Pro Asp Phe
        355                 360                 365

Thr Asn Pro Thr Ala Leu Ala Trp Trp Glu Asp Met Val Ala Glu Phe
370                 375                 380

His Asp Gln Val Pro Phe Asp Gly Met Trp Ile Asp Met Asn Glu Pro
385                 390                 395                 400

Ser Asn Phe Ile Arg Gly Ser Glu Asp Gly Cys Pro Asn Asn Glu Leu
            405                 410                 415

Glu Asn Pro Pro Tyr Val Pro Gly Val Val Gly Gly Thr Leu Gln Ala
            420                 425                 430

Ala Thr Ile Cys Ala Ser Ser His Gln Phe Leu Ser Thr His Tyr Asn
        435                 440                 445

Leu His Asn Leu Tyr Gly Leu Thr Glu Ala Ile Ala Ser His Arg Ala
450                 455                 460

Leu Val Lys Ala Arg Gly Thr Arg Pro Phe Val Ile Ser Arg Ser Thr

```
              465                 470                 475                 480
        Phe Ala Gly His Gly Arg Tyr Ala Gly His Trp Thr Gly Asp Val Trp
                        485                 490                 495

Ser Ser Trp Glu Gln Leu Ala Ser Ser Val Pro Glu Ile Leu Gln Phe
                        500                 505                 510

Asn Leu Leu Gly Val Pro Leu Gly Ala Asp Val Cys Gly Phe Leu
                        515                 520                 525

Gly Asn Thr Ser Glu Glu Leu Cys Val Arg Trp Thr Gln Leu Gly Ala
                    530                 535                 540

Phe Tyr Pro Phe Met Arg Asn His Asn Ser Leu Leu Ser Leu Pro Gln
        545                 550                 555                 560

Glu Pro Tyr Ser Phe Ser Glu Pro Ala Gln Gln Ala Met Arg Lys Ala
                        565                 570                 575

Leu Thr Leu Arg Tyr Ala Leu Leu Pro His Leu Tyr Thr Leu Phe His
                        580                 585                 590

Gln Ala His Val Ala Gly Glu Thr Val Ala Arg Pro Leu Phe Leu Glu
                        595                 600                 605

Phe Pro Lys Asp Ser Ser Thr Trp Thr Val Asp His Gln Leu Leu Trp
                610                 615                 620

Gly Glu Ala Leu Leu Ile Thr Pro Val Leu Gln Ala Gly Lys Ala Glu
        625                 630                 635                 640

Val Thr Gly Tyr Phe Pro Leu Gly Thr Trp Tyr Asp Leu Gln Thr Val
                        645                 650                 655

Pro Val Glu Ala
                        660

<210> SEQ ID NO 4
<211> LENGTH: 495
<212> TYPE: PRT
<213> ORGANISM: Homo sapiens

<400> SEQUENCE: 4

Gly Ala Asn Leu Tyr Gly Ser His Pro Phe Tyr Leu Ala Leu Glu Asp
        1               5                   10                  15

Gly Gly Ser Ala His Gly Val Phe Leu Leu Asn Ser Asn Ala Met Asp
                        20                  25                  30

Val Val Leu Gln Pro Ser Pro Ala Leu Ser Trp Arg Ser Thr Gly Gly
                        35                  40                  45

Ile Leu Asp Val Tyr Ile Phe Leu Gly Pro Glu Pro Lys Ser Val Val
                    50                  55                  60

Gln Gln Tyr Leu Asp Val Val Gly Tyr Pro Phe Met Pro Pro Tyr Trp
        65                  70                  75                  80

Gly Leu Gly Phe His Leu Cys Arg Trp Gly Tyr Ser Ser Thr Ala Ile
                        85                  90                  95

Thr Arg Gln Val Val Glu Asn Met Thr Arg Ala His Phe Pro Leu Asp
                        100                 105                 110

Val Gln Trp Asn Asp Leu Asp Tyr Met Asp Ser Arg Arg Asp Phe Thr
                        115                 120                 125

Phe Asn Lys Asp Gly Phe Arg Asp Phe Pro Ala Met Val Gln Glu Leu
                    130                 135                 140

His Gln Gly Gly Arg Arg Tyr Met Met Ile Val Asp Pro Ala Ile Ser
        145                 150                 155                 160

Ser Ser Gly Pro Ala Gly Ser Tyr Arg Pro Tyr Asp Glu Gly Leu Arg
                        165                 170                 175
```

```
Arg Gly Val Phe Ile Thr Asn Glu Thr Gly Gln Pro Leu Ile Gly Lys
            180                 185                 190

Val Trp Pro Gly Ser Thr Ala Phe Pro Asp Phe Thr Asn Pro Thr Ala
        195                 200                 205

Leu Ala Trp Trp Glu Asp Met Val Ala Glu Phe His Asp Gln Val Pro
    210                 215                 220

Phe Asp Gly Met Trp Ile Asp Met Asn Glu Pro Ser Asn Phe Ile Arg
225                 230                 235                 240

Gly Ser Glu Asp Gly Cys Pro Asn Asn Glu Leu Glu Asn Pro Pro Tyr
                245                 250                 255

Val Pro Gly Val Val Gly Gly Thr Leu Gln Ala Ala Thr Ile Cys Ala
            260                 265                 270

Ser Ser His Gln Phe Leu Ser Thr His Tyr Asn Leu His Asn Leu Tyr
        275                 280                 285

Gly Leu Thr Glu Ala Ile Ala Ser His Arg Ala Leu Val Lys Ala Arg
    290                 295                 300

Gly Thr Arg Pro Phe Val Ile Ser Arg Ser Thr Phe Ala Gly His Gly
305                 310                 315                 320

Arg Tyr Ala Gly His Trp Thr Gly Asp Val Trp Ser Ser Trp Glu Gln
                325                 330                 335

Leu Ala Ser Ser Val Pro Glu Ile Leu Gln Phe Asn Leu Leu Gly Val
            340                 345                 350

Pro Leu Val Gly Ala Asp Val Cys Gly Phe Leu Gly Asn Thr Ser Glu
        355                 360                 365

Glu Leu Cys Val Arg Trp Thr Gln Leu Gly Ala Phe Tyr Pro Phe Met
    370                 375                 380

Arg Asn His Asn Ser Leu Leu Ser Leu Pro Gln Glu Pro Tyr Ser Phe
385                 390                 395                 400

Ser Glu Pro Ala Gln Gln Ala Met Arg Lys Ala Leu Thr Leu Arg Tyr
                405                 410                 415

Ala Leu Leu Pro His Leu Tyr Thr Leu Phe His Gln Ala His Val Ala
            420                 425                 430

Gly Glu Thr Val Ala Arg Pro Leu Phe Leu Glu Phe Pro Lys Asp Ser
        435                 440                 445

Ser Thr Trp Thr Val Asp His Gln Leu Leu Trp Gly Glu Ala Leu Leu
    450                 455                 460

Ile Thr Pro Val Leu Gln Ala Gly Lys Ala Glu Val Thr Gly Tyr Phe
465                 470                 475                 480

Pro Leu Gly Thr Trp Tyr Asp Leu Gln Thr Val Pro Val Glu Ala
                485                 490                 495

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Ser Gly Gly Gly Gly Ser
1               5                   10                  15

<210> SEQ ID NO 6
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Gly Ser Thr Ser Gly Ser Gly Lys Ser Glu Gly Lys Gly
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Gln Lys Leu Ile Ser Glu Glu Asp Leu
1               5                   10

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 10

| Asp | Ile | Val | Leu | Thr | Gln | Ser | Pro | Ala | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Gln | Arg | Ala | Thr | Ile | Ser | Cys | Arg | Ala | Ser | Lys | Ser | Val | Ser | Thr | Ser |
|---|---|---|---|---|---|---|---|---|---|---|---|---|---|---|---|
| | | | 20 | | | | | 25 | | | | | 30 | | |

| Ser | Tyr | Ser | Tyr | Met | His | Trp | Tyr | Gln | Gln | Lys | Pro | Gly | Gln | Pro | Pro |
|---|---|---|---|---|---|---|---|---|---|---|---|---|---|---|---|
| | | | 35 | | | | | 40 | | | | | 45 | | |

| Lys | Leu | Leu | Ile | Lys | Tyr | Ala | Ser | Tyr | Leu | Glu | Ser | Gly | Val | Pro | Ala |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Gly | Thr | Asp | Phe | His | Leu | Asn | Ile | His |
|---|---|---|---|---|---|---|---|---|---|---|---|---|---|---|---|
| 65 | | | | | 70 | | | | | 75 | | | | | 80 |

| Pro | Val | Glu | Glu | Glu | Asp | Ala | Ala | Thr | Tyr | Tyr | Cys | Gln | His | Ser | Arg |
|---|---|---|---|---|---|---|---|---|---|---|---|---|---|---|---|
| | | | | 85 | | | | | 90 | | | | | 95 | |

| Glu | Phe | Pro | Trp | Thr | Phe | Gly | Gly | Gly | Thr | Lys | Leu | Glu | Leu | Lys |
|---|---|---|---|---|---|---|---|---|---|---|---|---|---|---|
| | | | | 100 | | | | | 105 | | | | | 110 |

<210> SEQ ID NO 11
<211> LENGTH: 931
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

| Asp | Ile | Val | Leu | Thr | Gln | Ser | Pro | Ala | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Gln | Arg | Ala | Thr | Ile | Ser | Cys | Arg | Ala | Ser | Lys | Ser | Val | Ser | Thr | Ser |
|---|---|---|---|---|---|---|---|---|---|---|---|---|---|---|---|
| | | | 20 | | | | | 25 | | | | | 30 | | |

| Ser | Tyr | Ser | Tyr | Met | His | Trp | Tyr | Gln | Gln | Lys | Pro | Gly | Gln | Pro | Pro |
|---|---|---|---|---|---|---|---|---|---|---|---|---|---|---|---|
| | | | 35 | | | | | 40 | | | | | 45 | | |

| Lys | Leu | Leu | Ile | Lys | Tyr | Ala | Ser | Tyr | Leu | Glu | Ser | Gly | Val | Pro | Ala |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Gly | Thr | Asp | Phe | His | Leu | Asn | Ile | His |
|---|---|---|---|---|---|---|---|---|---|---|---|---|---|---|---|
| 65 | | | | | 70 | | | | | 75 | | | | | 80 |

| Pro | Val | Glu | Glu | Glu | Asp | Ala | Ala | Thr | Tyr | Tyr | Cys | Gln | His | Ser | Arg |
|---|---|---|---|---|---|---|---|---|---|---|---|---|---|---|---|
| | | | | 85 | | | | | 90 | | | | | 95 | |

| Glu | Phe | Pro | Trp | Thr | Phe | Gly | Gly | Gly | Thr | Lys | Leu | Glu | Leu | Lys | Gly |
|---|---|---|---|---|---|---|---|---|---|---|---|---|---|---|---|
| | | | | 100 | | | | | 105 | | | | | 110 | |

| Gly | Gly | Gly | Ser | Gly | Gly | Gly | Gly | Ser | Gly | Gly | Gly | Gly | Ser | Glu | Val |
|---|---|---|---|---|---|---|---|---|---|---|---|---|---|---|---|
| | | 115 | | | | | 120 | | | | | 125 | | | |

| Gln | Leu | Val | Glu | Ser | Gly | Gly | Gly | Leu | Val | Lys | Pro | Gly | Gly | Ser | Arg |
|---|---|---|---|---|---|---|---|---|---|---|---|---|---|---|---|
| | 130 | | | | | 135 | | | | | 140 | | | | |

| Lys | Leu | Ser | Cys | Ala | Ala | Ser | Gly | Phe | Thr | Phe | Ser | Asn | Tyr | Gly | Met |
|---|---|---|---|---|---|---|---|---|---|---|---|---|---|---|---|
| 145 | | | | | 150 | | | | | 155 | | | | | 160 |

| His | Trp | Val | Arg | Gln | Ala | Pro | Glu | Lys | Gly | Leu | Glu | Trp | Val | Ala | Tyr |
|---|---|---|---|---|---|---|---|---|---|---|---|---|---|---|---|
| | | | | 165 | | | | | 170 | | | | | 175 | |

| Ile | Ser | Ser | Gly | Ser | Ser | Thr | Ile | Tyr | Tyr | Ala | Asp | Thr | Val | Lys | Gly |
|---|---|---|---|---|---|---|---|---|---|---|---|---|---|---|---|
| | | | 180 | | | | | 185 | | | | | 190 | | |

| Arg | Phe | Thr | Ile | Ser | Arg | Asp | Asn | Ala | Lys | Asn | Thr | Leu | Phe | Leu | Gln |
|---|---|---|---|---|---|---|---|---|---|---|---|---|---|---|---|
| | | | 195 | | | | | 200 | | | | | 205 | | |

| Met | Thr | Ser | Leu | Arg | Ser | Glu | Asp | Thr | Ala | Met | Tyr | Tyr | Cys | Ala | Arg |
|---|---|---|---|---|---|---|---|---|---|---|---|---|---|---|---|
| | 210 | | | | | 215 | | | | | 220 | | | | |

Arg Gly Leu Leu Leu Asp Tyr Trp Gly Gln Gly Thr Thr Leu Thr Val

```
              225                 230                 235                 240
          Ser Ser Glu Gln Lys Leu Ser Glu Glu Asp Leu Gly Ser Thr Ser Gly
                          245                 250                 255

Ser Gly Lys Ser Ser Glu Gly Lys Gly Gly Gln Pro Trp Cys Phe Phe
                          260                 265                 270

Pro Pro Ser Tyr Pro Ser Tyr Lys Leu Glu Asn Leu Ser Ser Ser Glu
                          275                 280                 285

Met Gly Tyr Thr Ala Thr Leu Thr Arg Thr Thr Pro Thr Phe Phe Pro
                          290                 295                 300

Lys Asp Ile Leu Thr Leu Arg Leu Asp Val Met Met Glu Thr Glu Asn
          305                 310                 315                 320

Arg Leu His Phe Thr Ile Lys Asp Pro Ala Asn Arg Arg Tyr Glu Val
                          325                 330                 335

Pro Leu Glu Thr Pro Arg Val His Ser Arg Ala Pro Ser Pro Leu Tyr
                          340                 345                 350

Ser Val Glu Phe Ser Glu Glu Pro Phe Gly Val Ile Val His Arg Gln
                          355                 360                 365

Leu Asp Gly Arg Val Leu Leu Asn Thr Thr Val Ala Pro Leu Phe Phe
                          370                 375                 380

Ala Asp Gln Phe Leu Gln Leu Ser Thr Ser Leu Pro Ser Gln Tyr Ile
          385                 390                 395                 400

Thr Gly Leu Ala Glu His Leu Ser Pro Leu Met Leu Ser Thr Ser Trp
                          405                 410                 415

Thr Arg Ile Thr Leu Trp Asn Arg Asp Leu Ala Pro Thr Pro Gly Ala
                          420                 425                 430

Asn Leu Tyr Gly Ser His Pro Phe Tyr Leu Ala Leu Glu Asp Gly Gly
                          435                 440                 445

Ser Ala His Gly Val Phe Leu Leu Asn Ser Asn Ala Met Asp Val Val
                          450                 455                 460

Leu Gln Pro Ser Pro Ala Leu Ser Trp Arg Ser Thr Gly Gly Ile Leu
          465                 470                 475                 480

Asp Val Tyr Ile Phe Leu Gly Pro Glu Pro Lys Ser Val Val Gln Gln
                          485                 490                 495

Tyr Leu Asp Val Val Gly Tyr Pro Phe Met Pro Pro Tyr Trp Gly Leu
                          500                 505                 510

Gly Phe His Leu Cys Arg Trp Gly Tyr Ser Ser Thr Ala Ile Thr Arg
                          515                 520                 525

Gln Val Val Glu Asn Met Thr Arg Ala His Phe Pro Leu Asp Val Gln
                          530                 535                 540

Trp Asn Asp Leu Asp Tyr Met Asp Ser Arg Arg Asp Phe Thr Phe Asn
          545                 550                 555                 560

Lys Asp Gly Phe Arg Asp Phe Pro Ala Met Val Gln Glu Leu His Gln
                          565                 570                 575

Gly Gly Arg Arg Tyr Met Met Ile Val Asp Pro Ala Ile Ser Ser Ser
                          580                 585                 590

Gly Pro Ala Gly Ser Tyr Arg Leu Tyr Asp Glu Gly Leu Arg Arg Gly
                          595                 600                 605

Val Phe Ile Thr Asn Glu Thr Gly Gln Pro Leu Ile Gly Lys Val Trp
                          610                 615                 620

Pro Gly Ser Thr Ala Phe Pro Asp Phe Thr Asn Pro Thr Ala Leu Ala
          625                 630                 635                 640

Trp Trp Glu Asp Met Val Ala Glu Phe His Asp Gln Val Pro Phe Asp
                          645                 650                 655
```

```
Gly Met Trp Ile Asp Met Asn Glu Pro Ser Asn Phe Ile Arg Gly Ser
            660                 665                 670

Glu Asp Gly Cys Pro Asn Asn Glu Leu Glu Asn Pro Pro Tyr Val Pro
        675                 680                 685

Gly Val Val Gly Gly Thr Leu Gln Ala Ala Thr Ile Cys Ala Ser Ser
    690                 695                 700

His Gln Phe Leu Ser Thr His Tyr Asn Leu His Asn Leu Tyr Gly Leu
705                 710                 715                 720

Thr Glu Ala Ile Ala Ser His Arg Ala Leu Val Lys Ala Arg Gly Thr
                725                 730                 735

Arg Pro Phe Val Ile Ser Arg Ser Thr Phe Ala Gly His Gly Arg Tyr
            740                 745                 750

Ala Gly His Trp Thr Gly Asp Val Trp Ser Ser Trp Glu Gln Leu Ala
        755                 760                 765

Ser Ser Val Pro Glu Ile Leu Gln Phe Asn Leu Leu Gly Val Pro Leu
    770                 775                 780

Val Gly Ala Asp Val Cys Gly Phe Leu Gly Asn Thr Ser Glu Glu Leu
785                 790                 795                 800

Cys Val Arg Trp Thr Gln Leu Gly Ala Phe Tyr Pro Phe Met Arg Asn
                805                 810                 815

His Asn Ser Leu Leu Ser Leu Pro Gln Glu Pro Tyr Ser Phe Ser Glu
            820                 825                 830

Pro Ala Gln Gln Ala Met Arg Lys Ala Leu Thr Leu Arg Tyr Ala Leu
        835                 840                 845

Leu Pro His Leu Tyr Thr Leu Phe His Gln Ala His Val Ala Gly Glu
    850                 855                 860

Thr Val Ala Arg Pro Leu Phe Leu Glu Phe Pro Lys Asp Ser Ser Thr
865                 870                 875                 880

Trp Thr Val Asp His Gln Leu Leu Trp Gly Glu Ala Leu Leu Ile Thr
                885                 890                 895

Pro Val Leu Gln Ala Gly Lys Ala Glu Val Thr Gly Tyr Phe Pro Leu
            900                 905                 910

Gly Thr Trp Tyr Asp Leu Gln Thr Val Pro Ile Glu Ala His His His
        915                 920                 925

His His His
    930

<210> SEQ ID NO 12
<211> LENGTH: 766
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
```

-continued

```
                65                  70                  75                  80
Pro Val Glu Glu Glu Asp Ala Ala Thr Tyr Tyr Cys Gln His Ser Arg
                    85                  90                  95
Glu Phe Pro Trp Thr Phe Gly Gly Gly Thr Lys Leu Glu Leu Lys Gly
                100                 105                 110
Gly Gly Gly Ser Gly Gly Gly Gly Ser Gly Gly Gly Gly Ser Glu Val
                115                 120                 125
Gln Leu Val Glu Ser Gly Gly Gly Leu Val Lys Pro Gly Gly Ser Arg
                130                 135                 140
Lys Leu Ser Cys Ala Ala Ser Gly Phe Thr Phe Ser Asn Tyr Gly Met
145                 150                 155                 160
His Trp Val Arg Gln Ala Pro Glu Lys Gly Leu Glu Trp Val Ala Tyr
                165                 170                 175
Ile Ser Ser Gly Ser Ser Thr Ile Tyr Tyr Ala Asp Thr Val Lys Gly
                180                 185                 190
Arg Phe Thr Ile Ser Arg Asp Asn Ala Lys Asn Thr Leu Phe Leu Gln
                195                 200                 205
Met Thr Ser Leu Arg Ser Glu Asp Thr Ala Met Tyr Tyr Cys Ala Arg
210                 215                 220
Arg Gly Leu Leu Leu Asp Tyr Trp Gly Gln Gly Thr Thr Leu Thr Val
225                 230                 235                 240
Ser Ser Glu Gln Lys Leu Ser Glu Glu Asp Leu Gly Ser Thr Ser Gly
                245                 250                 255
Ser Gly Lys Ser Ser Glu Gly Lys Gly Gly Ala Asn Leu Tyr Gly Ser
                260                 265                 270
His Pro Phe Tyr Leu Ala Leu Glu Asp Gly Gly Ser Ala His Gly Val
                275                 280                 285
Phe Leu Leu Asn Ser Asn Ala Met Asp Val Val Leu Gln Pro Ser Pro
                290                 295                 300
Ala Leu Ser Trp Arg Ser Thr Gly Gly Ile Leu Asp Val Tyr Ile Phe
305                 310                 315                 320
Leu Gly Pro Glu Pro Lys Ser Val Val Gln Gln Tyr Leu Asp Val Val
                325                 330                 335
Gly Tyr Pro Phe Met Pro Pro Tyr Trp Gly Leu Gly Phe His Leu Cys
                340                 345                 350
Arg Trp Gly Tyr Ser Ser Thr Ala Ile Thr Arg Gln Val Val Glu Asn
                355                 360                 365
Met Thr Arg Ala His Phe Pro Leu Asp Val Gln Trp Asn Asp Leu Asp
370                 375                 380
Tyr Met Asp Ser Arg Arg Asp Phe Thr Phe Asn Lys Asp Gly Phe Arg
385                 390                 395                 400
Asp Phe Pro Ala Met Val Gln Glu Leu His Gln Gly Gly Arg Arg Tyr
                405                 410                 415
Met Met Ile Val Asp Pro Ala Ile Ser Ser Ser Gly Pro Ala Gly Ser
                420                 425                 430
Tyr Arg Leu Tyr Asp Glu Gly Leu Arg Arg Gly Val Phe Ile Thr Asn
                435                 440                 445
Glu Thr Gly Gln Pro Leu Ile Gly Lys Val Trp Pro Gly Ser Thr Ala
                450                 455                 460
Phe Pro Asp Phe Thr Asn Pro Thr Ala Leu Ala Trp Trp Glu Asp Met
465                 470                 475                 480
Val Ala Glu Phe His Asp Gln Val Pro Phe Asp Gly Met Trp Ile Asp
                485                 490                 495
```

```
Met Asn Glu Pro Ser Asn Phe Ile Arg Gly Ser Glu Asp Gly Cys Pro
            500                 505                 510

Asn Asn Glu Leu Glu Asn Pro Pro Tyr Val Pro Gly Val Val Gly Gly
            515                 520                 525

Thr Leu Gln Ala Ala Thr Ile Cys Ala Ser Ser His Gln Phe Leu Ser
            530                 535                 540

Thr His Tyr Asn Leu His Asn Leu Tyr Gly Leu Thr Glu Ala Ile Ala
545                 550                 555                 560

Ser His Arg Ala Leu Val Lys Ala Arg Gly Thr Arg Pro Phe Val Ile
                565                 570                 575

Ser Arg Ser Thr Phe Ala Gly His Gly Arg Tyr Ala Gly His Trp Thr
            580                 585                 590

Gly Asp Val Trp Ser Ser Trp Glu Gln Leu Ala Ser Ser Val Pro Glu
            595                 600                 605

Ile Leu Gln Phe Asn Leu Leu Gly Val Pro Leu Val Gly Ala Asp Val
            610                 615                 620

Cys Gly Phe Leu Gly Asn Thr Ser Glu Glu Leu Cys Val Arg Trp Thr
625                 630                 635                 640

Gln Leu Gly Ala Phe Tyr Pro Phe Met Arg Asn His Asn Ser Leu Leu
                645                 650                 655

Ser Leu Pro Gln Glu Pro Tyr Ser Phe Ser Glu Pro Ala Gln Gln Ala
            660                 665                 670

Met Arg Lys Ala Leu Thr Leu Arg Tyr Ala Leu Leu Pro His Leu Tyr
            675                 680                 685

Thr Leu Phe His Gln Ala His Val Ala Gly Glu Thr Val Ala Arg Pro
690                 695                 700

Leu Phe Leu Glu Phe Pro Lys Asp Ser Ser Thr Trp Thr Val Asp His
705                 710                 715                 720

Gln Leu Leu Trp Gly Glu Ala Leu Leu Ile Thr Pro Val Leu Gln Ala
                725                 730                 735

Gly Lys Ala Glu Val Thr Gly Tyr Phe Pro Leu Gly Thr Trp Tyr Asp
            740                 745                 750

Leu Gln Thr Val Pro Ile Glu Ala His His His His His His
            755                 760                 765

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ile Ser Ser Gly Ser Ser Thr Ile Tyr Tyr Ala Asp Thr Val Lys
1               5                   10                  15
```

Gly

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Leu Leu Leu Asp Tyr
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Lys Ser Val Ser Thr Ser Ser Tyr Ser Tyr Met His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ala Ser Tyr Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln His Ser Arg Glu Phe Pro Trp Thr
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Ile His
1

<210> SEQ ID NO 20
<211> LENGTH: 5
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 20

Ser Ala Gly Ile His
1               5

<210> SEQ ID NO 21
<211> LENGTH: 892
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Arg Pro Gly Pro Arg Asp Ala Gln Ala His Pro Gly Arg Pro Arg
1               5                   10                  15

Ala Val Pro Thr Gln Cys Asp Val Pro Pro Asn Ser Arg Phe Asp Cys
            20                  25                  30

Ala Pro Asp Lys Ala Ile Thr Gln Glu Gln Cys Glu Ala Arg Gly Cys
        35                  40                  45

Cys Tyr Ile Pro Ala Lys Gln Gly Leu Gln Gly Ala Gln Met Gly Gln
    50                  55                  60

Pro Trp Cys Phe Phe Pro Pro Ser Tyr Pro Ser Tyr Lys Leu Glu Asn
65                  70                  75                  80

Leu Ser Ser Ser Glu Met Gly Tyr Thr Ala Thr Leu Thr Arg Thr Thr
                85                  90                  95

Pro Thr Phe Phe Pro Lys Asp Ile Leu Thr Leu Arg Leu Asp Val Met
            100                 105                 110

Met Glu Thr Glu Asn Arg Leu His Phe Thr Ile Lys Asp Pro Ala Asn
        115                 120                 125

Arg Arg Tyr Glu Val Pro Leu Glu Thr Pro His Val His Ser Arg Ala
    130                 135                 140

Pro Ser Pro Leu Tyr Ser Val Glu Phe Ser Glu Glu Pro Phe Gly Val
145                 150                 155                 160

Ile Val Arg Arg Gln Leu Asp Gly Arg Val Leu Leu Asn Thr Thr Val
                165                 170                 175

Ala Pro Leu Phe Phe Ala Asp Gln Phe Leu Gln Leu Ser Thr Ser Leu
            180                 185                 190

Pro Ser Gln Tyr Ile Thr Gly Leu Ala Glu His Leu Ser Pro Leu Met
        195                 200                 205

Leu Ser Thr Ser Trp Thr Arg Ile Thr Leu Trp Asn Arg Asp Leu Ala
    210                 215                 220

Pro Thr Pro Gly Ala Asn Leu Tyr Gly Ser His Pro Phe Tyr Leu Ala
225                 230                 235                 240

Leu Glu Asp Gly Gly Ser Ala His Gly Val Phe Leu Leu Asn Ser Asn
                245                 250                 255

Ala Met Asp Val Val Leu Gln Pro Ser Pro Ala Leu Ser Trp Arg Ser
            260                 265                 270

Thr Gly Gly Ile Leu Asp Val Tyr Ile Phe Leu Gly Pro Glu Pro Lys
        275                 280                 285

Ser Val Val Gln Gln Tyr Leu Asp Val Val Gly Tyr Pro Phe Met Pro
    290                 295                 300

Pro Tyr Trp Gly Leu Gly Phe His Leu Cys Arg Trp Gly Tyr Ser Ser
305                 310                 315                 320

```
Thr Ala Ile Thr Arg Gln Val Val Glu Asn Met Thr Arg Ala His Phe
                325                 330                 335

Pro Leu Asp Val Gln Trp Asn Asp Leu Asp Tyr Met Asp Ser Arg Arg
            340                 345                 350

Asp Phe Thr Phe Asn Lys Asp Gly Phe Arg Asp Phe Pro Ala Met Val
        355                 360                 365

Gln Glu Leu His Gln Gly Gly Arg Arg Tyr Met Met Ile Val Asp Pro
    370                 375                 380

Ala Ile Ser Ser Gly Pro Ala Gly Ser Tyr Arg Pro Tyr Asp Glu
385                 390                 395                 400

Gly Leu Arg Arg Gly Val Phe Ile Thr Asn Glu Thr Gly Gln Pro Leu
            405                 410                 415

Ile Gly Lys Val Trp Pro Gly Ser Thr Ala Phe Pro Asp Phe Thr Asn
        420                 425                 430

Pro Thr Ala Leu Ala Trp Trp Glu Asp Met Val Ala Glu Phe His Asp
    435                 440                 445

Gln Val Pro Phe Asp Gly Met Trp Ile Asp Met Asn Glu Pro Ser Asn
450                 455                 460

Phe Ile Arg Gly Ser Glu Asp Gly Cys Pro Asn Asn Glu Leu Glu Asn
465                 470                 475                 480

Pro Pro Tyr Val Pro Gly Val Val Gly Gly Thr Leu Gln Ala Ala Thr
            485                 490                 495

Ile Cys Ala Ser Ser His Gln Phe Leu Ser Thr His Tyr Asn Leu His
        500                 505                 510

Asn Leu Tyr Gly Leu Thr Glu Ala Ile Ala Ser His Arg Ala Leu Val
    515                 520                 525

Lys Ala Arg Gly Thr Arg Pro Phe Val Ile Ser Arg Ser Thr Phe Ala
530                 535                 540

Gly His Gly Arg Tyr Ala Gly His Trp Thr Gly Asp Val Trp Ser Ser
545                 550                 555                 560

Trp Glu Gln Leu Ala Ser Ser Val Pro Glu Ile Leu Gln Phe Asn Leu
            565                 570                 575

Leu Gly Val Pro Leu Val Gly Ala Asp Val Cys Gly Phe Leu Gly Asn
        580                 585                 590

Thr Ser Glu Glu Leu Cys Val Arg Trp Thr Gln Leu Gly Ala Phe Tyr
    595                 600                 605

Pro Phe Met Arg Asn His Asn Ser Leu Leu Ser Leu Pro Gln Glu Pro
610                 615                 620

Tyr Ser Phe Ser Glu Pro Ala Gln Gln Ala Met Arg Lys Ala Leu Thr
625                 630                 635                 640

Leu Arg Tyr Ala Leu Leu Pro His Leu Tyr Thr Leu Phe His Gln Ala
            645                 650                 655

His Val Ala Gly Glu Thr Val Ala Arg Pro Leu Phe Leu Glu Phe Pro
        660                 665                 670

Lys Asp Ser Ser Thr Trp Thr Val Asp His Gln Leu Leu Trp Gly Glu
    675                 680                 685

Ala Leu Leu Ile Thr Pro Val Leu Gln Ala Gly Lys Ala Glu Val Thr
690                 695                 700

Gly Tyr Phe Pro Leu Gly Thr Trp Tyr Asp Leu Gln Thr Val Pro Val
705                 710                 715                 720

Glu Ala Leu Gly Ser Leu Pro Pro Pro Ala Ala Pro Arg Glu Pro
            725                 730                 735

Ala Ile His Ser Glu Gly Gln Trp Val Thr Leu Pro Ala Pro Leu Asp
```

```
                    740                 745                 750
Thr Ile Asn Val His Leu Arg Ala Gly Tyr Ile Ile Pro Leu Gln Gly
            755                 760                 765

Pro Gly Leu Thr Thr Thr Glu Ser Arg Gln Gln Pro Met Ala Leu Ala
        770                 775                 780

Val Ala Leu Thr Lys Gly Gly Glu Ala Arg Gly Glu Leu Phe Trp Asp
785                 790                 795                 800

Asp Gly Glu Ser Leu Glu Val Leu Glu Arg Gly Ala Tyr Thr Gln Val
                805                 810                 815

Ile Phe Leu Ala Arg Asn Asn Thr Ile Val Asn Glu Leu Val Arg Val
            820                 825                 830

Thr Ser Glu Gly Ala Gly Leu Gln Leu Gln Lys Val Thr Val Leu Gly
        835                 840                 845

Val Ala Thr Ala Pro Gln Gln Val Leu Ser Asn Gly Val Pro Val Ser
    850                 855                 860

Asn Phe Thr Tyr Ser Pro Asp Thr Lys Val Leu Asp Ile Cys Val Ser
865                 870                 875                 880

Leu Leu Met Gly Glu Gln Phe Leu Val Ser Trp Cys
                885                 890

<210> SEQ ID NO 22
<211> LENGTH: 886
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ala Gln Ala His Pro Gly Arg Pro Arg Ala Val Pro Thr Gln Cys
1               5                   10                  15

Asp Val Pro Pro Asn Ser Arg Phe Asp Cys Ala Pro Asp Lys Ala Ile
            20                  25                  30

Thr Gln Glu Gln Cys Glu Ala Arg Gly Cys Cys Tyr Ile Pro Ala Lys
        35                  40                  45

Gln Gly Leu Gln Gly Ala Gln Met Gly Gln Pro Trp Cys Phe Phe Pro
    50                  55                  60

Pro Ser Tyr Pro Ser Tyr Lys Leu Glu Asn Leu Ser Ser Ser Glu Met
65              70                  75                  80

Gly Tyr Thr Ala Thr Leu Thr Arg Thr Thr Pro Thr Phe Phe Pro Lys
                85                  90                  95

Asp Ile Leu Thr Leu Arg Leu Asp Val Met Met Glu Thr Glu Asn Arg
            100                 105                 110

Leu His Phe Thr Ile Lys Asp Pro Ala Asn Arg Arg Tyr Glu Val Pro
        115                 120                 125

Leu Glu Thr Pro His Val His Ser Arg Ala Pro Ser Pro Leu Tyr Ser
    130                 135                 140

Val Glu Phe Ser Glu Glu Pro Phe Gly Val Ile Val Arg Arg Gln Leu
145                 150                 155                 160

Asp Gly Arg Val Leu Leu Asn Thr Thr Val Ala Pro Leu Phe Phe Ala
                165                 170                 175

Asp Gln Phe Leu Gln Leu Ser Thr Ser Leu Pro Ser Gln Tyr Ile Thr
            180                 185                 190

Gly Leu Ala Glu His Leu Ser Pro Leu Met Leu Ser Thr Ser Trp Thr
        195                 200                 205
```

-continued

```
Arg Ile Thr Leu Trp Asn Arg Asp Leu Ala Pro Thr Pro Gly Ala Asn
    210                 215                 220
Leu Tyr Gly Ser His Pro Phe Tyr Leu Ala Leu Glu Asp Gly Gly Ser
225                 230                 235                 240
Ala His Gly Val Phe Leu Leu Asn Ser Asn Ala Met Asp Val Val Leu
                    245                 250                 255
Gln Pro Ser Pro Ala Leu Ser Trp Arg Ser Thr Gly Gly Ile Leu Asp
                260                 265                 270
Val Tyr Ile Phe Leu Gly Pro Glu Pro Lys Ser Val Gln Gln Tyr
            275                 280                 285
Leu Asp Val Val Gly Tyr Pro Phe Met Pro Pro Tyr Trp Gly Leu Gly
290                 295                 300
Phe His Leu Cys Arg Trp Gly Tyr Ser Ser Thr Ala Ile Thr Arg Gln
305                 310                 315                 320
Val Val Glu Asn Met Thr Arg Ala His Phe Pro Leu Asp Val Gln Trp
                325                 330                 335
Asn Asp Leu Asp Tyr Met Asp Ser Arg Arg Asp Phe Thr Phe Asn Lys
                340                 345                 350
Asp Gly Phe Arg Asp Phe Pro Ala Met Val Gln Glu Leu His Gln Gly
            355                 360                 365
Gly Arg Arg Tyr Met Met Ile Val Asp Pro Ala Ile Ser Ser Ser Gly
370                 375                 380
Pro Ala Gly Ser Tyr Arg Pro Tyr Asp Glu Gly Leu Arg Arg Gly Val
385                 390                 395                 400
Phe Ile Thr Asn Glu Thr Gly Gln Pro Leu Ile Gly Lys Val Trp Pro
                405                 410                 415
Gly Ser Thr Ala Phe Pro Asp Phe Thr Asn Pro Thr Ala Leu Ala Trp
            420                 425                 430
Trp Glu Asp Met Val Ala Glu Phe His Asp Gln Val Pro Phe Asp Gly
        435                 440                 445
Met Trp Ile Asp Met Asn Glu Pro Ser Asn Phe Ile Arg Gly Ser Glu
    450                 455                 460
Asp Gly Cys Pro Asn Asn Glu Leu Glu Asn Pro Pro Tyr Val Pro Gly
465                 470                 475                 480
Val Val Gly Gly Thr Leu Gln Ala Ala Thr Ile Cys Ala Ser Ser His
                485                 490                 495
Gln Phe Leu Ser Thr His Tyr Asn Leu His Asn Leu Tyr Gly Leu Thr
                500                 505                 510
Glu Ala Ile Ala Ser His Arg Ala Leu Val Lys Ala Arg Gly Thr Arg
            515                 520                 525
Pro Phe Val Ile Ser Arg Ser Thr Phe Ala Gly His Gly Arg Tyr Ala
530                 535                 540
Gly His Trp Thr Gly Asp Val Trp Ser Ser Trp Glu Gln Leu Ala Ser
545                 550                 555                 560
Ser Val Pro Glu Ile Leu Gln Phe Asn Leu Leu Gly Val Pro Leu Val
                565                 570                 575
Gly Ala Asp Val Cys Gly Phe Leu Gly Asn Thr Ser Glu Glu Leu Cys
            580                 585                 590
Val Arg Trp Thr Gln Leu Gly Ala Phe Tyr Pro Phe Met Arg Asn His
        595                 600                 605
Asn Ser Leu Leu Ser Leu Pro Gln Glu Pro Tyr Ser Phe Ser Glu Pro
    610                 615                 620
Ala Gln Gln Ala Met Arg Lys Ala Leu Thr Leu Arg Tyr Ala Leu Leu
```

Pro His Leu Tyr Thr Leu Phe His Gln Ala His Val Ala Gly Glu Thr
            625                 630                 635                 640

Val Ala Arg Pro Leu Phe Leu Glu Phe Pro Lys Asp Ser Ser Thr Trp
            645                 650                 655

Thr Val Asp His Gln Leu Leu Trp Gly Glu Ala Leu Leu Ile Thr Pro
            660                 665                 670

Val Leu Gln Ala Gly Lys Ala Glu Val Thr Gly Tyr Phe Pro Leu Gly
            675                 680                 685

Thr Trp Tyr Asp Leu Gln Thr Val Pro Val Glu Ala Leu Gly Ser Leu
            690                 695                 700

Pro Pro Pro Pro Ala Ala Pro Arg Glu Pro Ala Ile His Ser Glu Gly
705                 710                 715                 720

Gln Trp Val Thr Leu Pro Ala Pro Leu Asp Thr Ile Asn Val His Leu
            725                 730                 735

Arg Ala Gly Tyr Ile Ile Pro Leu Gln Gly Pro Gly Leu Thr Thr Thr
            740                 745                 750

Glu Ser Arg Gln Gln Pro Met Ala Leu Ala Val Ala Leu Thr Lys Gly
            755                 760                 765

Gly Glu Ala Arg Gly Glu Leu Phe Trp Asp Asp Gly Glu Ser Leu Glu
            770                 775                 780

Val Leu Glu Arg Gly Ala Tyr Thr Gln Val Ile Phe Leu Ala Arg Asn
785                 790                 795                 800

Asn Thr Ile Val Asn Glu Leu Val Arg Val Thr Ser Glu Gly Ala Gly
            805                 810                 815

Leu Gln Leu Gln Lys Val Thr Val Leu Gly Val Ala Thr Ala Pro Gln
            820                 825                 830

Gln Val Leu Ser Asn Gly Val Pro Val Ser Asn Phe Thr Tyr Ser Pro
            835                 840                 845

Asp Thr Lys Val Leu Asp Ile Cys Val Ser Leu Leu Met Gly Glu Gln
865                 850                 855                 860

Phe Leu Val Ser Trp Cys
            885

<210> SEQ ID NO 23
<211> LENGTH: 883
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala His Pro Gly Arg Pro Arg Ala Val Pro Thr Gln Cys Asp Val Pro
1               5                   10                  15

Pro Asn Ser Arg Phe Asp Cys Ala Pro Asp Lys Ala Ile Thr Gln Glu
                20                  25                  30

Gln Cys Glu Ala Arg Gly Cys Cys Tyr Ile Pro Ala Lys Gln Gly Leu
            35                  40                  45

Gln Gly Ala Gln Met Gly Gln Pro Trp Cys Phe Phe Pro Pro Ser Tyr
        50                  55                  60

Pro Ser Tyr Lys Leu Glu Asn Leu Ser Ser Ser Glu Met Gly Tyr Thr
65                  70                  75                  80

Ala Thr Leu Thr Arg Thr Thr Pro Thr Phe Phe Pro Lys Asp Ile Leu
                85                  90                  95

-continued

```
Thr Leu Arg Leu Asp Val Met Met Glu Thr Glu Asn Arg Leu His Phe
            100                 105                 110

Thr Ile Lys Asp Pro Ala Asn Arg Arg Tyr Glu Val Pro Leu Glu Thr
            115                 120                 125

Pro His Val His Ser Arg Ala Pro Ser Pro Leu Tyr Ser Val Glu Phe
            130                 135                 140

Ser Glu Glu Pro Phe Gly Val Ile Val Arg Arg Gln Leu Asp Gly Arg
145                 150                 155                 160

Val Leu Leu Asn Thr Thr Val Ala Pro Leu Phe Phe Ala Asp Gln Phe
                165                 170                 175

Leu Gln Leu Ser Thr Ser Leu Pro Ser Gln Tyr Ile Thr Gly Leu Ala
                180                 185                 190

Glu His Leu Ser Pro Leu Met Leu Ser Thr Ser Trp Thr Arg Ile Thr
            195                 200                 205

Leu Trp Asn Arg Asp Leu Ala Pro Thr Pro Gly Ala Asn Leu Tyr Gly
            210                 215                 220

Ser His Pro Phe Tyr Leu Ala Leu Glu Asp Gly Gly Ser Ala His Gly
225                 230                 235                 240

Val Phe Leu Leu Asn Ser Asn Ala Met Asp Val Val Leu Gln Pro Ser
                245                 250                 255

Pro Ala Leu Ser Trp Arg Ser Thr Gly Gly Ile Leu Asp Val Tyr Ile
                260                 265                 270

Phe Leu Gly Pro Glu Pro Lys Ser Val Val Gln Gln Tyr Leu Asp Val
            275                 280                 285

Val Gly Tyr Pro Phe Met Pro Pro Tyr Trp Gly Leu Gly Phe His Leu
            290                 295                 300

Cys Arg Trp Gly Tyr Ser Ser Thr Ala Ile Thr Arg Gln Val Val Glu
305                 310                 315                 320

Asn Met Thr Arg Ala His Phe Pro Leu Asp Val Gln Trp Asn Asp Leu
                325                 330                 335

Asp Tyr Met Asp Ser Arg Arg Asp Phe Thr Phe Asn Lys Asp Gly Phe
                340                 345                 350

Arg Asp Phe Pro Ala Met Val Gln Glu Leu His Gln Gly Gly Arg Arg
            355                 360                 365

Tyr Met Met Ile Val Asp Pro Ala Ile Ser Ser Ser Gly Pro Ala Gly
            370                 375                 380

Ser Tyr Arg Pro Tyr Asp Glu Gly Leu Arg Arg Gly Val Phe Ile Thr
385                 390                 395                 400

Asn Glu Thr Gly Gln Pro Leu Ile Gly Lys Val Trp Pro Gly Ser Thr
                405                 410                 415

Ala Phe Pro Asp Phe Thr Asn Pro Thr Ala Leu Ala Trp Trp Glu Asp
                420                 425                 430

Met Val Ala Glu Phe His Asp Gln Val Pro Phe Asp Gly Met Trp Ile
            435                 440                 445

Asp Met Asn Glu Pro Ser Asn Phe Ile Arg Gly Ser Glu Asp Gly Cys
            450                 455                 460

Pro Asn Asn Glu Leu Glu Asn Pro Pro Tyr Val Pro Gly Val Val Gly
465                 470                 475                 480

Gly Thr Leu Gln Ala Ala Thr Ile Cys Ala Ser Ser His Gln Phe Leu
                485                 490                 495

Ser Thr His Tyr Asn Leu His Asn Leu Tyr Gly Leu Thr Glu Ala Ile
            500                 505                 510

Ala Ser His Arg Ala Leu Val Lys Ala Arg Gly Thr Arg Pro Phe Val
```

```
            515                 520                 525
Ile Ser Arg Ser Thr Phe Ala Gly His Gly Arg Tyr Ala Gly His Trp
530                 535                 540
Thr Gly Asp Val Trp Ser Ser Trp Glu Gln Leu Ala Ser Ser Val Pro
545                 550                 555                 560
Glu Ile Leu Gln Phe Asn Leu Leu Gly Val Pro Leu Val Gly Ala Asp
                565                 570                 575
Val Cys Gly Phe Leu Gly Asn Thr Ser Glu Glu Leu Cys Val Arg Trp
            580                 585                 590
Thr Gln Leu Gly Ala Phe Tyr Pro Phe Met Arg Asn His Asn Ser Leu
        595                 600                 605
Leu Ser Leu Pro Gln Glu Pro Tyr Ser Phe Ser Glu Pro Ala Gln Gln
610                 615                 620
Ala Met Arg Lys Ala Leu Thr Leu Arg Tyr Ala Leu Leu Pro His Leu
625                 630                 635                 640
Tyr Thr Leu Phe His Gln Ala His Val Ala Gly Glu Thr Val Ala Arg
                645                 650                 655
Pro Leu Phe Leu Glu Phe Pro Lys Asp Ser Ser Thr Trp Thr Val Asp
            660                 665                 670
His Gln Leu Leu Trp Gly Glu Ala Leu Leu Ile Thr Pro Val Leu Gln
        675                 680                 685
Ala Gly Lys Ala Glu Val Thr Gly Tyr Phe Pro Leu Gly Thr Trp Tyr
690                 695                 700
Asp Leu Gln Thr Val Pro Val Glu Ala Leu Gly Ser Leu Pro Pro Pro
705                 710                 715                 720
Pro Ala Ala Pro Arg Glu Pro Ala Ile His Ser Glu Gly Gln Trp Val
                725                 730                 735
Thr Leu Pro Ala Pro Leu Asp Thr Ile Asn Val His Leu Arg Ala Gly
            740                 745                 750
Tyr Ile Ile Pro Leu Gln Gly Pro Gly Leu Thr Thr Thr Glu Ser Arg
        755                 760                 765
Gln Gln Pro Met Ala Leu Ala Val Ala Leu Thr Lys Gly Gly Glu Ala
770                 775                 780
Arg Gly Glu Leu Phe Trp Asp Asp Gly Glu Ser Leu Glu Val Leu Glu
785                 790                 795                 800
Arg Gly Ala Tyr Thr Gln Val Ile Phe Leu Ala Arg Asn Asn Thr Ile
                805                 810                 815
Val Asn Glu Leu Val Arg Val Thr Ser Glu Gly Ala Gly Leu Gln Leu
            820                 825                 830
Gln Lys Val Thr Val Leu Gly Val Ala Thr Ala Pro Gln Gln Val Leu
        835                 840                 845
Ser Asn Gly Val Pro Val Ser Asn Phe Thr Tyr Ser Pro Asp Thr Lys
850                 855                 860
Val Leu Asp Ile Cys Val Ser Leu Leu Met Gly Glu Gln Phe Leu Val
865                 870                 875                 880
Ser Trp Cys

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Gly Phe Thr Phe Ser Asn Tyr Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ser Ser Gly Ser Ser Thr Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Arg Arg Gly Leu Leu Leu Asp Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Val Ser Thr Ser Ser Tyr Ser Tyr
1               5                   10

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ala Ser
1

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln His Ser Arg Glu Phe Pro Trp Thr
1               5

<210> SEQ ID NO 30
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Gly Gly Ser Gly Gly Gly Ser Gly Gly Gly Ser Gly Gly
1               5                   10

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Ile Leu Leu His Asp Phe Leu Leu Val Pro Arg Glu Leu Ser Gly
1               5                   10                  15

Ser Ser Pro Val Leu Glu Glu Thr His Pro Ala His
            20                  25

<210> SEQ ID NO 32
<211> LENGTH: 937
<212> TYPE: PRT
<213> ORGANISM: Bos taurus

<400> SEQUENCE: 32

Met Met Arg Trp Pro Pro Cys Ser Arg Pro Leu Leu Gly Val Cys Thr
1               5                   10                  15

Leu Leu Ser Leu Ala Leu Leu Gly His Ile Leu Leu His Asp Leu Glu
            20                  25                  30

Val Val Pro Arg Glu Leu Arg Gly Phe Ser Gln Asp Glu Ile His Gln
        35                  40                  45

Ala Cys Gln Pro Gly Ala Ser Ser Pro Glu Cys Arg Gly Ser Pro Arg
    50                  55                  60

Ala Ala Pro Thr Gln Cys Asp Leu Pro Pro Asn Ser Arg Phe Asp Cys
65                  70                  75                  80

Ala Pro Asp Lys Gly Ile Thr Pro Gln Gln Cys Glu Ala Arg Gly Cys
                85                  90                  95

Cys Tyr Met Pro Ala Glu Trp Pro Pro Asp Ala Gln Met Gly Gln Pro
            100                 105                 110

Trp Cys Phe Phe Pro Pro Ser Tyr Pro Ser Tyr Arg Leu Glu Asn Leu
        115                 120                 125

Thr Thr Thr Glu Thr Gly Tyr Thr Ala Thr Leu Thr Arg Ala Val Pro
    130                 135                 140

Thr Phe Phe Pro Lys Asp Ile Met Thr Leu Arg Leu Asp Met Leu Met
145                 150                 155                 160

Glu Thr Glu Ser Arg Leu His Phe Thr Ile Lys Asp Pro Ala Asn Arg
                165                 170                 175

Arg Tyr Glu Val Pro Leu Glu Thr Pro Arg Val Tyr Ser Gln Ala Pro
            180                 185                 190

Phe Thr Leu Tyr Ser Val Glu Phe Ser Glu Pro Phe Gly Val Val
        195                 200                 205

Val Arg Arg Lys Leu Asp Gly Arg Val Leu Asn Thr Thr Val Ala
    210                 215                 220

Pro Leu Phe Phe Ala Asp Gln Phe Leu Gln Leu Ser Thr Ser Leu Pro
225                 230                 235                 240
```

```
Ser Gln His Ile Thr Gly Leu Ala Glu His Leu Gly Ser Leu Met Leu
            245                 250                 255

Ser Thr Asn Trp Thr Lys Ile Thr Leu Trp Asn Arg Asp Ile Ala Pro
            260                 265                 270

Glu Pro Asn Val Asn Leu Tyr Gly Ser His Pro Phe Tyr Leu Val Leu
            275                 280                 285

Glu Asp Gly Gly Leu Ala His Gly Val Phe Leu Leu Asn Ser Asn Ala
            290                 295                 300

Met Asp Val Val Leu Gln Pro Ser Pro Ala Leu Ser Trp Arg Ser Thr
305                 310                 315                 320

Gly Gly Ile Leu Asp Val Tyr Ile Phe Leu Gly Pro Glu Pro Lys Ser
            325                 330                 335

Val Val Gln Gln Tyr Leu Asp Val Val Gly Tyr Pro Phe Met Pro Pro
            340                 345                 350

Tyr Trp Gly Leu Gly Phe His Leu Cys Arg Trp Gly Tyr Ser Thr Ser
            355                 360                 365

Ala Ile Thr Arg Gln Val Val Glu Asn Met Thr Arg Ala Tyr Phe Pro
            370                 375                 380

Leu Asp Val Gln Trp Asn Asp Leu Asp Tyr Met Asp Ala Arg Arg Asp
385                 390                 395                 400

Phe Thr Phe Asn Lys Asp His Phe Gly Asp Phe Pro Ala Met Val Gln
            405                 410                 415

Glu Leu His Gln Gly Gly Arg Arg Tyr Ile Met Ile Val Asp Pro Ala
            420                 425                 430

Ile Ser Ser Ser Gly Pro Ala Gly Thr Tyr Arg Pro Tyr Asp Glu Gly
            435                 440                 445

Leu Arg Arg Gly Val Phe Ile Thr Asn Glu Thr Gly Gln Pro Leu Ile
            450                 455                 460

Gly Gln Val Trp Pro Gly Leu Thr Ala Phe Pro Asp Phe Thr Asn Pro
465                 470                 475                 480

Glu Thr Leu Asp Trp Trp Gln Asp Met Val Thr Glu Phe His Ala Gln
            485                 490                 495

Val Pro Phe Asp Gly Met Trp Ile Asp Met Asn Glu Pro Ser Asn Phe
            500                 505                 510

Val Arg Gly Ser Val Asp Gly Cys Pro Asp Asn Ser Leu Glu Asn Pro
            515                 520                 525

Pro Tyr Leu Pro Gly Val Val Gly Gly Thr Leu Arg Ala Ala Thr Ile
            530                 535                 540

Cys Ala Ser Ser His Gln Phe Leu Ser Thr His Tyr Asp Leu His Asn
545                 550                 555                 560

Leu Tyr Gly Leu Thr Glu Ala Leu Ala Ser His Arg Ala Leu Val Lys
            565                 570                 575

Ala Arg Gly Met Arg Pro Phe Val Ile Ser Arg Ser Thr Phe Ala Gly
            580                 585                 590

His Gly Arg Tyr Ser Gly His Trp Thr Gly Asp Val Trp Ser Asn Trp
            595                 600                 605

Glu Gln Leu Ser Tyr Ser Val Pro Glu Ile Leu Leu Phe Asn Leu Leu
            610                 615                 620

Gly Val Pro Leu Val Gly Ala Asp Ile Cys Gly Phe Leu Gly Asn Thr
625                 630                 635                 640

Ser Glu Glu Leu Cys Val Arg Trp Thr Gln Leu Gly Ala Phe Tyr Pro
            645                 650                 655
```

Phe Met Arg Asn His Asn Ala Leu Asn Ser Gln Pro Gln Glu Pro Tyr
            660                 665                 670

Arg Phe Ser Glu Thr Ala Gln Gln Ala Met Arg Lys Ala Phe Thr Leu
        675                 680                 685

Arg Tyr Val Leu Leu Pro Tyr Leu Tyr Thr Leu Phe His Arg Ala His
    690                 695                 700

Val Arg Gly Glu Thr Val Ala Arg Pro Leu Phe Leu Glu Phe Pro Glu
705                 710                 715                 720

Asp Pro Ser Thr Trp Thr Val Asp Arg Gln Leu Leu Trp Gly Glu Ala
                725                 730                 735

Leu Leu Ile Thr Pro Val Leu Glu Ala Glu Lys Val Glu Val Thr Gly
            740                 745                 750

Tyr Phe Pro Gln Gly Thr Trp Tyr Asp Leu Gln Thr Val Pro Met Glu
        755                 760                 765

Ala Phe Gly Ser Leu Pro Pro Pro Ala Pro Leu Thr Ser Val Ile His
    770                 775                 780

Ser Lys Gly Gln Trp Val Thr Leu Ser Ala Pro Leu Asp Thr Ile Asn
785                 790                 795                 800

Val His Leu Arg Ala Gly His Ile Ile Pro Met Gln Gly Pro Ala Leu
                805                 810                 815

Thr Thr Thr Glu Ser Arg Lys Gln His Met Ala Leu Ala Val Ala Leu
            820                 825                 830

Thr Ala Ser Gly Glu Ala Gln Gly Glu Leu Phe Trp Asp Asp Gly Glu
        835                 840                 845

Ser Leu Gly Val Leu Asp Gly Gly Asp Tyr Thr Gln Leu Ile Phe Leu
    850                 855                 860

Ala Lys Asn Asn Thr Phe Val Asn Lys Leu Val His Val Ser Ser Glu
865                 870                 875                 880

Gly Ala Ser Leu Gln Leu Arg Asn Val Thr Val Leu Gly Val Ala Thr
                885                 890                 895

Ala Pro Gln Gln Val Leu Cys Asn Ser Val Pro Val Ser Asn Phe Thr
            900                 905                 910

Phe Ser Pro Asp Thr Glu Thr Leu Ala Ile Pro Val Ser Leu Thr Met
        915                 920                 925

Gly Glu Gln Phe Val Ile Ser Trp Ser
    930                 935

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Phe Glu Arg Gln
1               5

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)

```
<223> OTHER INFORMATION: This sequence may encompass 1-10 repeating "Gly
      Gly Gly Gly Ser" repeating units

<400> SEQUENCE: 34

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser
    50

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ser Ser Leu Asn Ile Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Arg Arg Arg Arg Arg
1               5
```

UNITED STATES PATENT AND TRADEMARK OFFICE
CERTIFICATE OF CORRECTION

PATENT NO. : 10,017,581 B2
APPLICATION NO. : 14/769270
DATED : July 10, 2018
INVENTOR(S) : Dustin D. Armstrong and Jeffrey C. Way It is certified that error appears in the above-identified patent and that said Letters Patent is hereby corrected as shown below:

In the Claims

Column 140, Claim 32, Lines 8-9, the phrase "which CDRs are according to the IMGT stem" should read "which CDRs are according to the IMGT system".

Signed and Sealed this
Twenty-seventh Day of November, 2018

Andrei Iancu
*Director of the United States Patent and Trademark Office*